US011014958B2

(12) United States Patent
Bjornson et al.

(10) Patent No.: US 11,014,958 B2
(45) Date of Patent: *May 25, 2021

(54) FLUORESCENT POLYMERASE ENZYME SUBSTRATES HAVING PROTEIN SHIELDS

(71) Applicant: Pacific Biosciences of California, Inc., Menlo Park, CA (US)

(72) Inventors: Keith Bjornson, Fremont, CA (US); Jeremiah Hanes, Woodside, CA (US); Erik Miller, Berkeley, CA (US); Satwik Kamtekar, Mountain View, CA (US); Lubomir Sebo, Hayward, CA (US); Louis Brogley, Santa Cruz, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 287 days.

This patent is subject to a terminal disclaimer.

(21) Appl. No.: 16/012,428

(22) Filed: Jun. 19, 2018

(65) Prior Publication Data

US 2019/0010183 A1 Jan. 10, 2019

Related U.S. Application Data

(63) Continuation of application No. 14/727,553, filed on Jun. 1, 2015, now Pat. No. 10,023,605, which is a continuation of application No. 13/767,619, filed on Feb. 14, 2013, now Pat. No. 9,062,091.

(60) Provisional application No. 61/599,149, filed on Feb. 15, 2012.

(51) Int. Cl.
| | |
|---|---|
| *C07H 21/04* | (2006.01) |
| *C12Q 1/68* | (2018.01) |
| *G01N 33/58* | (2006.01) |
| *C07K 14/36* | (2006.01) |
| *C07H 19/06* | (2006.01) |
| *C07H 19/16* | (2006.01) |
| *C12Q 1/6874* | (2018.01) |
| *C12N 9/10* | (2006.01) |
| *C09B 23/08* | (2006.01) |
| *C09B 69/10* | (2006.01) |
| *C12Q 1/6869* | (2018.01) |

(52) U.S. Cl.
CPC .............. *C07H 21/04* (2013.01); *C07H 19/06* (2013.01); *C07H 19/16* (2013.01); *C07K 14/36* (2013.01); *C09B 23/083* (2013.01); *C09B 69/105* (2013.01); *C12N 9/10* (2013.01); *C12Q 1/6869* (2013.01); *C12Q 1/6874* (2013.01); *G01N 33/582* (2013.01); *G01N 33/583* (2013.01); *C12Q 2523/313* (2013.01); *C12Q 2535/113* (2013.01); *C12Q 2563/107* (2013.01); *C12Q 2563/131* (2013.01)

(58) Field of Classification Search
CPC ........ C07H 21/04; C07H 19/06; C07H 19/16; C12Q 1/6869
See application file for complete search history.

(56) References Cited

U.S. PATENT DOCUMENTS

| | | |
|---|---|---|
| 4,711,955 A | 12/1987 | Ward et al. |
| 5,648,245 A | 7/1997 | Fire et al. |
| 5,688,648 A | 11/1997 | Mathies et al. |
| 5,714,320 A | 2/1998 | Kool |
| 6,153,442 A | 11/2000 | Pirio et al. |
| 6,255,083 B1 | 7/2001 | Williams |
| 6,261,808 B1 | 7/2001 | Auerbach |
| 6,399,335 B1 | 6/2002 | Kao et al. |
| 6,787,308 B2 | 9/2004 | Balasubramanian et al. |
| 7,013,054 B2 | 3/2006 | Levene et al. |
| 7,041,812 B2 | 5/2006 | Kumar et al. |
| 7,056,661 B2 | 6/2006 | Korlach et al. |
| 7,170,050 B2 | 1/2007 | Turner et al. |
| 7,405,281 B2 | 7/2008 | Xu et al. |
| 7,476,503 B2 | 1/2009 | Turner et al. |
| 7,486,865 B2 | 2/2009 | Foquet et al. |
| 7,777,013 B2 | 8/2010 | Xu et al. |
| 7,842,475 B2 | 11/2010 | Zheng et al. |
| 7,901,889 B2 | 3/2011 | Christians et al. |
| 7,906,284 B2 | 3/2011 | Turner et al. |

(Continued)

FOREIGN PATENT DOCUMENTS

| | | |
|---|---|---|
| WO | 9106678 A1 | 5/1991 |
| WO | 9627025 A1 | 9/1996 |

OTHER PUBLICATIONS

Eid et al., "Real-Time DNA Sequencing From Single Polymerase Molecules," Science (2009) 323:133-138.

(Continued)

*Primary Examiner* — Jezia Riley
(74) *Attorney, Agent, or Firm* — Robert H. Reamey

(57) ABSTRACT

Compositions, methods, and systems are provided for fluorescent polymerase enzyme substrates comprising protein shields for improving enzyme photostability in single molecule real time sequencing. Fluorescent polymerase enzyme substrates of the invention have a protein shield between the fluorescent dye moieties and nucleotide moieties of the polymerase enzyme substrate. The polymerase enzyme substrates have a nucleotide component and a dye component, each attached to a protein. The attachments can be covalent. The protein can, for example, prevent the direct interaction of the fluorescent dye moiety with the enzyme when carrying out nucleotide synthesis, preventing photodamage to the enzyme. The polymerase enzyme substrates of the invention can have multiple dyes and multiple nucleotide moieties.

25 Claims, 37 Drawing Sheets

Specification includes a Sequence Listing.

(56) References Cited

U.S. PATENT DOCUMENTS

| | | |
|---|---|---|
| 7,968,702 B2 | 6/2011 | Wegener et al. |
| 7,973,146 B2 | 7/2011 | Shen et al. |
| 8,058,031 B2 | 11/2011 | Xu et al. |
| 8,133,672 B2 | 3/2012 | Bjornson et al. |
| 8,133,702 B2 | 3/2012 | Shen et al. |
| 9,062,091 B2 | 6/2015 | Bjornson et al. |
| 10,023,605 B2 * | 7/2018 | Bjornson ............... C12N 9/10 |
| 2003/0077610 A1 | 4/2003 | Nelson et al. |
| 2003/0162213 A1 | 8/2003 | Fuller et al. |
| 2004/0241716 A1 | 12/2004 | Kumar et al. |
| 2009/0118129 A1 | 5/2009 | Turner |
| 2009/0208957 A1 | 8/2009 | Korlach et al. |
| 2009/0233302 A1 | 9/2009 | Wegener et al. |
| 2010/0057185 A1 | 3/2010 | Melsheimer et al. |
| 2010/0152424 A1 | 6/2010 | Korlach et al. |
| 2010/0221716 A1 | 9/2010 | Flusberg et al. |
| 2010/0255488 A1 | 10/2010 | Kong et al. |
| 2011/0183320 A1 | 7/2011 | Flusberg et al. |
| 2011/0244447 A1 | 10/2011 | Korlach et al. |
| 2011/0256618 A1 | 10/2011 | Eid et al. |
| 2012/0052506 A1 | 3/2012 | Yue et al. |
| 2012/0052507 A1 | 3/2012 | Shen |
| 2012/0058469 A1 | 3/2012 | Shen |
| 2012/0058473 A1 | 3/2012 | Yue et al. |
| 2012/0058482 A1 | 3/2012 | Shen et al. |
| 2012/0077189 A1 | 3/2012 | Shen et al. |
| 2012/0115736 A1 | 5/2012 | Bjornson et al. |
| 2013/0303385 A1 | 11/2013 | Korlach et al. |
| 2014/0005405 A1 | 1/2014 | Yue et al. |

OTHER PUBLICATIONS

Levene et al., "Zero-mode Waveguides for Single-molecule Analysis at High Concentration" Science (2003) 299:682-686.

Wilbur et al., "Design and Synthesis of Bis-Biotin-Containing Reagents for Applications Utilizing Monoclonal Antibody-Based Pretargeting Systems with Streptavidin Mutants," Bioconjug. Chem. (2010) 21(7):1225-1238.

International Search Report and Written Opinion dated Jun. 3, 2013 for related PCT/US2013/026222.

International Preliminary Report on Patentability dated Aug. 28, 2014 for related PCT/US2013/026222.

EP Search Report dated Sep. 25, 2015 for related EP 13749460.5.

EP Search Report dated Aug. 3, 2017 for related EP 17165469.2.

EP Search Report dated Oct. 30, 2019 for related EP 19182978.7.

* cited by examiner

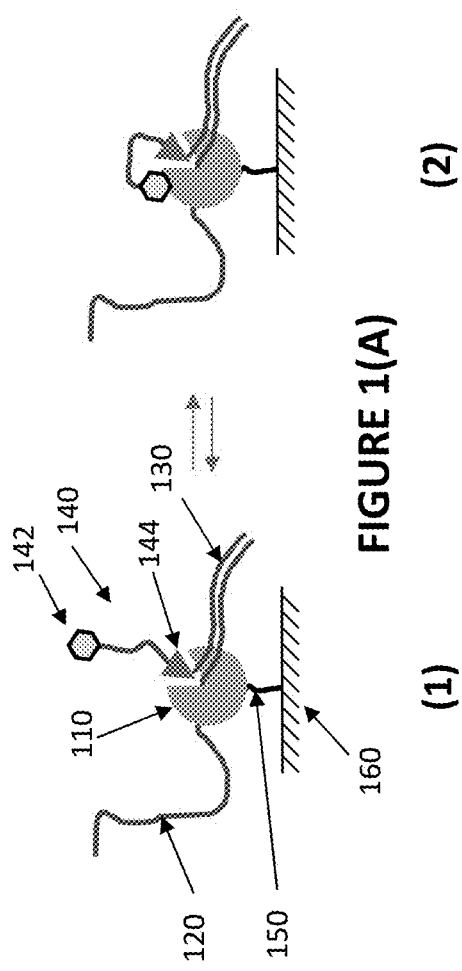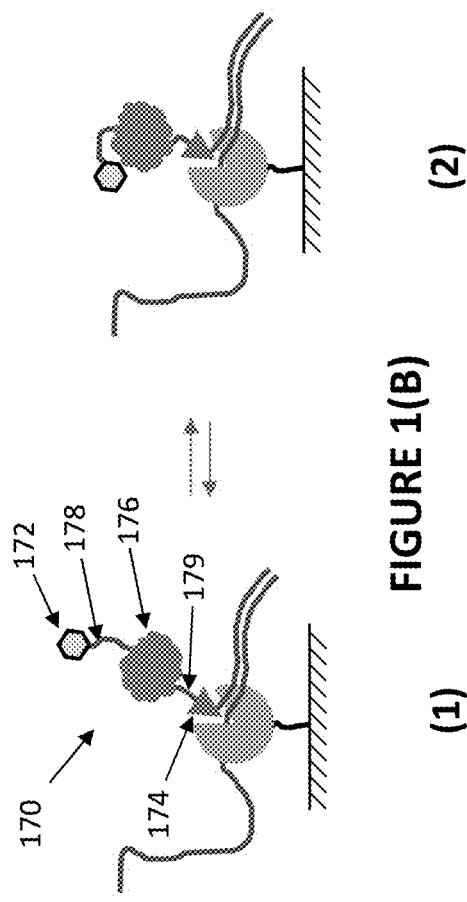

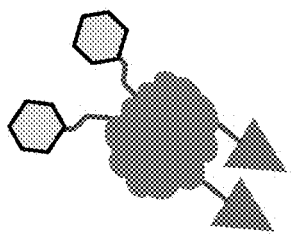
Figure 2(A)
FIGURE 2(B)
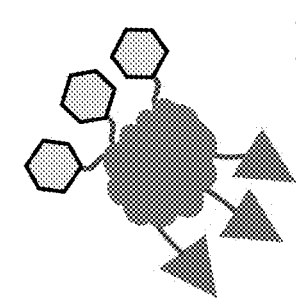
FIGURE 2(C)
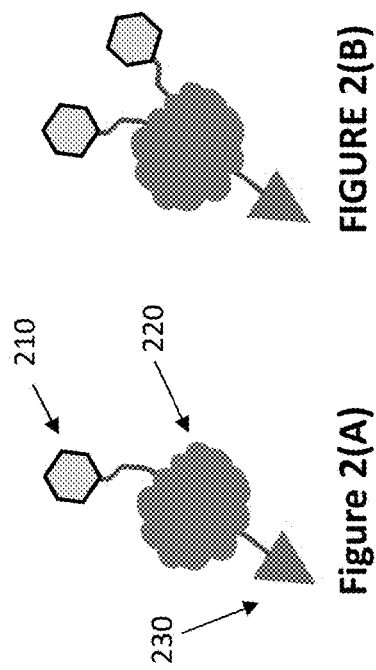
FIGURE 2(D)
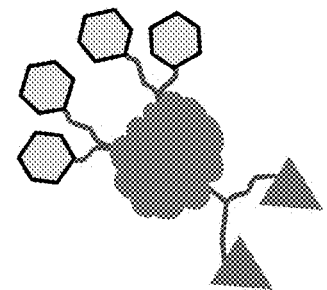
FIGURE 2(E)
FIGURE 2(F)
FIGURE 2(G)
FIGURE 2(H)
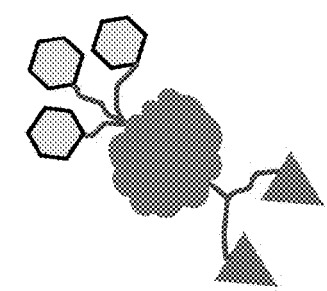
FIGURE 2(I)
FIGURE 2(J)
FIGURE 2(K)
FIGURE 2(L)

TOP7

Tamavidin

Maltose Binding Protein

Bis-biotin Linkers

SEQUENCE LISTING

<160> NUMBER OF SEQ ID NOS: 5

<210> SEQ ID NO 1
<211> LENGTH: 76
<212> TYPE: PRT
<213> ORGANISM: Rattus norvegicus

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu

```
                50                  55                  60
Ser Thr Leu His Leu Val Leu Arg Leu Arg Gly Gly
 65                  70                  75
```

<210> SEQ ID NO 2
<211> LENGTH: 106
<212> TYPE: PRT
<213> ORGANISM: Artificial Sequence
<220> FEATURE:
<223> OTHER INFORMATION: non-natural - human designed

<400> SEQUENCE: 2

```
Met Gly Asp Ile Gln Val Gln Val Asn Ile Asp Asp Asn Gly Lys Asn
 1               5                  10                  15

Phe Asp Tyr Thr Tyr Thr Val Thr Thr Glu Ser Glu Leu Gln Lys Val
                20                  25                  30

Leu Asn Glu Leu Met Asp Tyr Ile Lys Lys Gln Gly Ala Lys Arg Val
            35                  40                  45

Arg Ile Ser Ile Thr Ala Arg Thr Lys Lys Glu Ala Glu Lys Phe Ala
 50                  55                  60

Ala Ile Leu Ile Lys Val Phe Ala Glu Leu Gly Tyr Asn Asp Ile Asn
 65                  70                  75                  80

Val Thr Phe Asp Gly Asp Thr Val Thr Val Glu Gly Gln Leu Glu Gly
                85                  90                  95

Gly Ser Leu Glu His His His His His His
            100                 105
```

<210> SEQ ID NO 3
<211> LENGTH: 143
<212> TYPE: PRT
<213> ORGANISM: Pleurotus cornucopiae

<400> SEQUENCE: 3

```
Met Lys Asp Val Gln Ser Leu Leu Thr Gly Thr Trp Tyr Asn Glu Leu
 1               5                  10                  15

Gly Ser Thr Met Asn Leu Thr Ala Asn Lys Asp Gly Ser Leu Thr Gly
                20                  25                  30

Thr Tyr His Ser Asn Val Gly Glu Val Pro Pro Thr Tyr His Leu Ser
            35                  40                  45

Gly Arg Tyr Asn Leu Gln Pro Pro Ser Gly Gly Val Thr Leu Gly
 50                  55                  60

Trp Ala Val Ser Phe Glu Asn Thr Ser Ala Asn Val His Ser Val Ser
 65                  70                  75                  80

Thr Trp Ser Gly Gln Tyr Phe Ser Glu Pro Ala Glu Val Ile Leu Thr
                85                  90                  95

Gln Trp Leu Leu Ser Arg Ser Ser Glu Arg Glu Asp Leu Trp Gln Ser
            100                 105                 110

Thr His Val Gly His Asp Glu Phe Ser Lys Thr Lys Pro Thr Lys Glu
        115                 120                 125

Lys Ile Ala Gln Ala Gln Leu Leu Arg Arg Gly Leu Lys Phe Glu
 130                 135                 140
```

<210> SEQ ID NO 4
<211> LENGTH: 141
<212> TYPE: PRT
<213> ORGANISM: Pleurotus cornucopiae

<400> SEQUENCE: 4

```
Met Ser Asp Val Gln Ser Ser Leu Thr Gly Thr Trp Tyr Asn Glu Leu
1               5                   10                  15

Asn Ser Lys Met Glu Leu Thr Ala Asn Lys Asp Gly Thr Leu Thr Gly
            20                  25                  30

Lys Tyr Leu Ser Lys Val Gly Asp Val Tyr Val Pro Tyr Pro Leu Ser
        35                  40                  45

Gly Arg Tyr Asn Leu Gln Pro Pro Ala Gly Gln Gly Val Ala Leu Gly
    50                  55                  60

Trp Ala Val Ser Trp Glu Asn Ser Lys Ile His Ser Ala Thr Thr Trp
65              70                  75                      80

Ser Gly Gln Phe Phe Ser Glu Ser Ser Pro Val Ile Leu Thr Gln Trp
                85                  90                  95

Leu Leu Ser Ser Ser Thr Ala Arg Gly Asp Val Trp Glu Ser Thr Leu
            100                 105                 110

Val Gly Asn Asp Ser Phe Thr Lys Thr Ala Pro Thr Glu Gln Gln Ile
            115                 120                 125

Ala His Ala Gln Leu His Cys Arg Ala Pro Arg Leu Lys
            130                 135                 140

<210> SEQ ID NO 5
<211> LENGTH: 127
<212> TYPE: PRT
<213> ORGANISM: Streptomyces avidinii

<400> SEQUENCE: 5

Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65              70                  75                      80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
            115                 120                 125
```

FLUORESCENT POLYMERASE ENZYME SUBSTRATES HAVING PROTEIN SHIELDS

CROSS-REFERENCE TO RELATED APPLICATIONS

This application is a continuation of U.S. patent application Ser. No. 14/727,553 filed Jun. 1, 2015, which is a continuation of U.S. patent application Ser. No. 13/767,619 filed Feb. 14, 2013, which claims the benefit of Provisional U.S. Patent Application No. 61/599,149, filed Feb. 15, 2012, the full disclosure of which is incorporated herein by reference in its entireties for all purposes.

STATEMENT REGARDING FEDERALLY SPONSORED RESEARCH

Not Applicable.

INCORPORATION-BY-REFERENCE OF MATERIAL SUBMITTED BY U.S.P.T.O. EFS-WEB

The instant application contains a Sequence Listing which is being submitted in computer readable form via the United States Patent and Trademark Office eFS-WEB system, and is hereby incorporated by reference in its entirety for all purposes. The txt file submitted herewith contains only 6 KB file (Ser. No. 01/014,603_2018-09-12_SequenceListing.txt).

BACKGROUND OF THE INVENTION

The ability to read the genetic code has opened countless opportunities to benefit humankind. Whether it involves the improvement of food crops and livestock used for food, the identification of the causes of disease, the generation of targeted therapeutic methods and compositions, or simply the better understanding of what makes us who we are, a fundamental understanding of the blueprints of life is an integral and necessary component.

A variety of techniques and processes have been developed to obtain genetic information, including broad genetic profiling or identifying patterns of discrete markers in genetic codes and nucleotide level sequencing of entire genomes. With respect to determination of genetic sequences, while techniques have been developed to read, at the nucleotide level, a genetic sequence, such methods can be time-consuming and extremely costly.

Approaches have been developed to sequence genetic material with improved speed and reduced costs. Many of these methods rely upon the identification of nucleotides being incorporated by a polymerization enzyme during a template sequence-dependent nucleic acid synthesis reaction. In particular, by identifying nucleotides incorporated against a complementary template nucleic acid strand, one can identify the sequence of nucleotides in the template strand. A variety of such methods have been previously described. These methods include iterative processes where individual nucleotides are added one at a time, washed to remove free, unincorporated nucleotides, identified, and washed again to remove any terminator groups and labeling components before an additional nucleotide is added. Still other methods employ the "real-time" detection of incorporation events, where the act of incorporation gives rise to a signaling event that can be detected. In particularly elegant methods, labeling components are coupled to portions of the nucleotides that are removed during the incorporation event, eliminating any need to remove such labeling components before the next nucleotide is added (See, e.g., Eid, J. et al., Science, 323(5910), 133-138 (2009)).

In many of the enzyme mediated template-dependent sequencing methods, the photostability of the system is important. For example, in fluorescent based single molecule, real time sequencing, the enzyme is exposed to excitation radiation while the sequencing reaction is occurring. If the enzyme becomes damaged due to such irradiation, the sequencing reaction can become compromised or end.

The present invention provides methods, systems and compositions that provide for increased performance of such polymerization based sequencing methods, including systems having improved photo stability, among other benefits.

BRIEF SUMMARY OF THE INVENTION

In some aspects, the invention provides a polymerase enzyme substrate comprising: a protein comprising at least 60 amino acids; a nucleotide unit comprising at least one nucleoside polyphosphate attached through its phosphate portion to a first position on the protein; a dye component comprising at least one fluorescent dye moiety attached to a second position on the protein, wherein the first and second attachment points are spaced apart by a distance such that when a nucleoside phosphate attached to the protein is in the active site of the polymerase enzyme, a fluorescent dye moiety attached to the protein is shielded by the protein from coming into contact with the polymerase enzyme.

The substrate can be held together by covalent attachments. The protein can comprise 60 to 1,000 amino acids. The protein can comprise 80 to 600 amino acids.

The nucleotide component and dye component can be covalently attached to the protein.

The nucleotide component can comprise two or more nucleoside phosphates. The substrate can have 2, 3, 4, 5, 6, 7, or 8 nucleotide phosphates. The dye component can comprise two or more fluorescent dye moieties. The substrate has 2, 3, or 4 fluorescent dye moieties.

The covalent attachment can be through a cysteine or lysine residue on the protein.

The protein can have two or more nucleotide components. The protein can have two or more dye components. The protein can have two or more nucleotide components and two or more dye components wherein when any nucleotide phosphate in a nucleotide component is in the active site of the polymerase enzyme, all fluorescent dye moieties in the dye components are shielded by the protein from coming into contact with the polymerase enzyme.

The protein can comprise a first protein and a second protein, the first protein and second protein are associated or connected, the first protein having one or more nucleotide components attached to it, and the second protein having one or more dye components attached to it. The first protein and second protein can be associated. The first protein and second protein can comprise barnase and barstar.

The first protein and second protein can be connected by a covalent linkage. The first protein and second protein can be connected through one or more linkers.

In some aspects, the invention provides a polymerase enzyme substrate comprising: a protein comprising at least 60 amino acids; a nucleotide component comprising at least one nucleoside polyphosphate attached through its phosphate portion to a first position on the protein; a dye component comprising at least one fluorescent dye moiety attached to a second position on the protein, wherein the first and second attachment points are spaced apart by a distance of greater than 2 nm.

The protein can have two or more nucleotide components. The protein can have two or more dye components. The protein can have two or more nucleotide components and two or more dye components wherein when any nucleotide phosphate in a nucleotide component is in the active site of the polymerase enzyme, all fluorescent dye moieties in the dye components are shielded by the protein from coming into contact with the polymerase enzyme.

In some aspects, the invention provides a method for nucleic acid sequencing comprising: providing an array of individually observable enzyme-nucleic acid template complexes on a chip; exposing the chip to the reagents for polymerase mediated nucleic acid synthesis of a growing nucleic acid strand, the reagents comprising a plurality of differently labeled polymerase enzyme substrates including at least one protein shield nucleotide; and optically monitoring the incorporation of the nucleoside monophosphate portions of the differently labeled polymerase enzyme substrates into the growing nucleic acid strand over time, thereby determining the sequence of at least a portion of the nucleic acid template.

In some aspects, the invention provides a polymerase enzyme substrate comprising: a nucleotide component comprising at least one nucleoside polyphosphate attached through its phosphate portion to a protein, wherein the protein has a plurality of labels embedded within it, whereby, when the polymerase enzyme substrate associates with a polymerase enzyme, the labels within the protein do not come into contact with a polymerase enzyme.

In some aspects, the invention provides the use of a protein sequence comprising at least 60 amino acids attached to and positioned between a nucleotide component and a dye component for inhibiting contact between said label and a polymerase enzyme during a polymerase catalysed nucleic acid synthesis reaction incorporating a nucleotide moiety of said nucleotide component.

In some aspects, the invention provides a method of shielding a polymerase enzyme when used in nucleic acid synthesis from labeled nucleotides, comprising providing a protein of at least 60 amino acids, having at least 20 amino acids in the primary sequence between the attachment point of each nucleotide and its respective label.

In some aspects, the invention provides a labeled nucleotide analog comprising: an avidin protein having four subunits, each subunit comprising one biotin binding site; one or two nucleotide components each comprising one or more phospholinked nucleotide moieties; and one or two dye components each comprising one or more dye moieties; wherein each component is bound to the avidin protein through a biotin moiety attached to a binding site on the avidin protein; and wherein at least one of the nucleotide or dye components comprise a bis-biotin moiety bound to two of the biotin binding sites on the avidin protein.

The nucleotide component can comprise a bis-biotin moiety, and the labeled nucleotide analog has two dye components each bound to the avidin through a single biotin moiety. The dye component can comprise a bis-biotin moiety, and the labeled nucleotide analog has two nucleotide components each bound to the avidin through a single biotin moiety. The labeled nucleotide analog can have one dye component and one nucleotide component and each of the dye component and the nucleotide component can comprise a bis-biotin moiety.

The number of dye moieties can be between 1 and 18 and the number of nucleotide moieties can be between 1 and 18. The number of dye moieties can be 1, 2, or 3 and the number of nucleotide moieties can be 6, 7, or 8. The number of bonds between biotins on the bis-biotin moiety can be between 15 and 50. The avidin protein can comprise either streptavidin or tamavidin. The dye moieties can comprise fluorescent labels.

In some aspects, the invention provides a reaction mixture for sequencing a nucleic acid template comprising: a polymerase enzyme complex comprising a polymerase enzyme, a template nucleic acid, and optionally a primer hybridized to the template nucleic acid, wherein the polymerase enzyme complex is immobilized on a surface; and sequencing reagents in contact with the surface comprising reagents for carrying out nucleic acid synthesis including 2 or more types of labeled nucleotide analogs, wherein one or more of the types of nucleotide analog is a protein-shielded nucleotide analog comprising an avidin protein having four subunits, each subunit comprising one biotin binding site; one or two nucleotide components each comprising one or more phospholinked nucleotide moieties; and one or two dye components each comprising one or more dye moieties; wherein each component is bound to the avidin through a biotin moiety attached to a binding site on the avidin protein; and wherein at least one of the nucleotide or dye components comprise a bis-biotin moiety bound to two of the biotin binding sites on the avidin protein.

The nucleotide component can comprise a bis-biotin moiety, and a labeled nucleotide analog has two dye components each bound to the avidin through a single biotin moiety. The dye component can comprise a bis-biotin moiety, and a labeled nucleotide analog has two nucleotide components each bound to the avidin through a single biotin moiety.

A labeled nucleotide analog can have one dye component and one nucleotide component and each of the dye component and the nucleotide component can comprise a bis-biotin moiety. The number of dye moieties can be between 1 and 18 and the number of nucleotide moieties can be between 1 and 18 for each nucleotide analog. The number of dye moieties can be 1, 2, or 3 and the number of nucleotide moieties can be 6, 7, or 8 for each nucleotide analog. The number of bonds between biotins on a bis-biotin moiety can be between 15 and 50. The avidin protein can comprise either streptavidin or tamavidin. The dye moieties can comprise fluorescent labels.

In some aspects, the invention provides a method for sequencing a nucleic acid template comprising: providing a polymerase enzyme complex comprising a polymerase enzyme, a template nucleic acid, and optionally a primer hybridized to the template nucleic acid, wherein the polymerase enzyme complex is immobilized on a surface; adding sequencing reagents in contact with the surface comprising reagents for carrying out nucleic acid synthesis including 2 or more types of labeled nucleotide analogs, wherein one or more of the types of nucleotide analog is a protein-shielded nucleotide analog comprising; an avidin protein having four subunits, each subunit comprising one biotin binding site; one or two nucleotide components each comprising one or more phospholinked nucleotide moieties; and one or two dye components each comprising one or more dye moieties; wherein each component is bound to the avidin through a biotin moiety attached to a binding site on the avidin protein; and wherein at least one of the nucleotide or dye components comprise a bis-biotin moiety bound to two of the biotin binding sites on the avidin protein; and determining the sequential addition of nucleotides to a nucleic acid strand complementary to a strand of the template nucleic acid by observing the interaction of the labeled nucleotide analogs with the polymerase enzyme complex.

The nucleotide component can comprise a bis-biotin moiety, and a labeled nucleotide analog can have two dye components each bound to the avidin through a single biotin moiety. The dye component can comprise a bis-biotin moiety, and a labeled nucleotide analog can have two nucleotide components each bound to the avidin through a single biotin moiety. A labeled nucleotide analog can have one dye component and one nucleotide component and each of the dye component and the nucleotide component can comprise a bis-biotin moiety.

The number of dye moieties can be between 1 and 18 and the number of nucleotide moieties can be between 1 and 18 in each nucleotide analog. The number of dye moieties can be 1, 2, or 3 and the number of nucleotide moieties can be 6, 7, or 8 in each nucleotide analog. The number of bonds between biotins on a bis-biotin moiety can be between 15 and 50. The avidin protein in an analog can comprise either streptavidin or tamavidin. The dye moieties can comprise fluorescent labels.

In some aspects, the invention provides a system for sequencing nucleic acids comprising: a chip comprising a plurality of polymerase enzyme complexes bound thereto, each polymerase enzyme complex individually optically resolvable, each polymerase enzyme complex comprising a polymerase enzyme, a template nucleic acid, and optionally a primer hybridized to the template nucleic acid, sequencing reagents in contact with the surface comprising reagents for carrying out nucleic acid synthesis including 2 or more types of fluorescently labeled nucleotide analogs, wherein one or more of the types of nucleotide analog is a protein-shielded nucleotide analog comprising; an avidin protein having four subunits, each subunit comprising one biotin binding site; one or two nucleotide components each comprising one or more phospholinked nucleotide moieties; and one or two dye components each comprising one or more dye moieties; wherein each component is bound to the avidin through a biotin moiety attached to a binding site on the avidin protein; and wherein at least one of the nucleotide or dye components comprise a bis-biotin moiety bound to two of the biotin binding sites on the avidin protein; and an illumination system for illuminating the polymerase enzyme complexes; and an optical detection system for detecting fluorescence from the labeled nucleotide analogs while they are interacting with the polymerase enzyme complexes; and a computer for analyzing the signals detected by the detection system to determine the sequential addition of nucleotides to a nucleic acid strand complementary to a strand of the template nucleic acid.

The nucleotide component can comprise a bis-biotin moiety, and a labeled nucleotide analog has two dye components each bound to the avidin through a single biotin moiety. The dye component can comprise a bis-biotin moiety, and a labeled nucleotide analog has two nucleotide components each bound to the avidin through a single biotin moiety. The labeled nucleotide analog can have one dye component and one nucleotide component and each of the dye component and the nucleotide component can comprise a bis-biotin moiety.

The number of dye moieties in the nucleotide analogs can be between 1 and 18 and the number of nucleotide moieties can be between 1 and 18 in each nucleotide analog. The number of dye moieties can be 1, 2, or 3 and the number of nucleotide moieties can be 6, 7, or 8 in each nucleotide analog. The number of bonds between biotins on a bis-biotin moiety can be between 15 and 50. The avidin protein in a nucleotide analog can comprise either streptavidin or tamavidin. The dye moieties can comprise fluorescent labels.

In some aspects, the invention provides a labeled nucleotide analog comprising: two avidin proteins connected to each other through a compound comprising two bis-biotin moieties and comprising a dye component having one or more dye moieties, wherein one of the avidins is attached to a bis-biotin moiety comprising a first nucleotide component having one or more phospholinked nucleotides, and wherein the other avidin is attached to a bis-biotin moiety comprising a second nucleotide component having one or more phospholinked nucleotides.

The first nucleotide component and second nucleotide component can be the same.

The number of dye moieties can be between 1 and 18 and the number of nucleotide moieties can be between 1 and 18.

The number of dye moieties can be 1, 2, or 3 and the number of nucleotide moieties can be between 8 and 24. The number of bonds between biotins on the bis-biotin moiety can be between 15 and 50. The avidin proteins can comprise either streptavidin or tamavidin. The dye moieties can comprise fluorescent labels.

BRIEF DESCRIPTION OF THE DRAWINGS

FIG. 1(A) illustrates single molecule real time sequencing with a conventional nucleotide analog, FIG. 1(B) illustrates single molecule real time sequencing with a nucleotide analog comprising a protein shield.

FIGS. 2(A)-2(L) show various constructs for nucleotide analogs of the invention having a protein shield. FIG. 2(A) shows a nucleotide analog having one nucleotide moiety and one fluorescent moiety. FIG. 2(B) shows a nucleotide analog having on nucleotide moiety and two fluorescent moieties. FIG. 2(C) shows a nucleotide analog having two nucleotide moieties and one dye moiety. FIG. 2(D) shows a nucleotide analog of the invention having two fluorescent moieties and two nucleotide moieties, each moiety attached at a different place on the protein. FIG. 2(E) shows a nucleotide analog of the invention having two fluorescent moieties and three nucleotide moieties, each moiety attached at a different place on the protein. FIG. 2(F) shows a nucleotide analog of the invention having three fluorescent moieties and two nucleotide moieties, each moiety attached at a different place on the protein. FIG. 2(G) shows a nucleotide analog of the invention having three fluorescent moieties and three nucleotide moieties, each moiety attached at a different place on the protein. FIG. 2(H) shows a nucleotide analog of the invention having two fluorescent moieties and one nucleotide moieties, the two fluorescent moieties connected to the same attachment point on the protein. FIG. 2(I) shows a nucleotide analog of the invention having two fluorescent moieties and two nucleotide moieties, the two fluorescent moieties connected to the same attachment point on the protein, and the two nucleotide moieties connected to a second attachment point on the protein. FIG. 2(J) shows a nucleotide analog of the invention having two fluorescent moieties and two nucleotide moieties, the two fluorescent moieties connected to the same attachment point on the protein, and the two nucleotide moieties are each connected to a different attachment point on the protein. FIG. 2(K) shows a nucleotide analog of the invention having three fluorescent moieties and two nucleotide moieties, the three fluorescent moieties connected to the same attachment point on the protein, and the two nucleotide moieties connected to a second attachment point on the protein. FIG. 2(L) shows a nucleotide analog of the invention having four fluorescent moieties and two nucleotide moieties, two of the fluorescent moieties are connected to one attachment point on the protein, the other two fluorescent moieties are connected to a second attachment point, and the two nucleotide moieties connected to a third attachment point on the protein.

FIG. 15 also includes two exemplary trifunctional linkers T1 and T7 that can be used to produce the bis-biotin dye component and biotin nucleotide components.

FIG. 27(B) also illustrates that this compound can be formed from a two streptavidins, a tetra-biotin dye component, and two bis-biotin hexanucleotide components.

FIG. 31(B) illustrates a pulse train with similar overall kinetics to that in FIG. 31(A), but with the use of multi-level dyes.

DETAILED DESCRIPTION OF THE INVENTION

Figure 3:
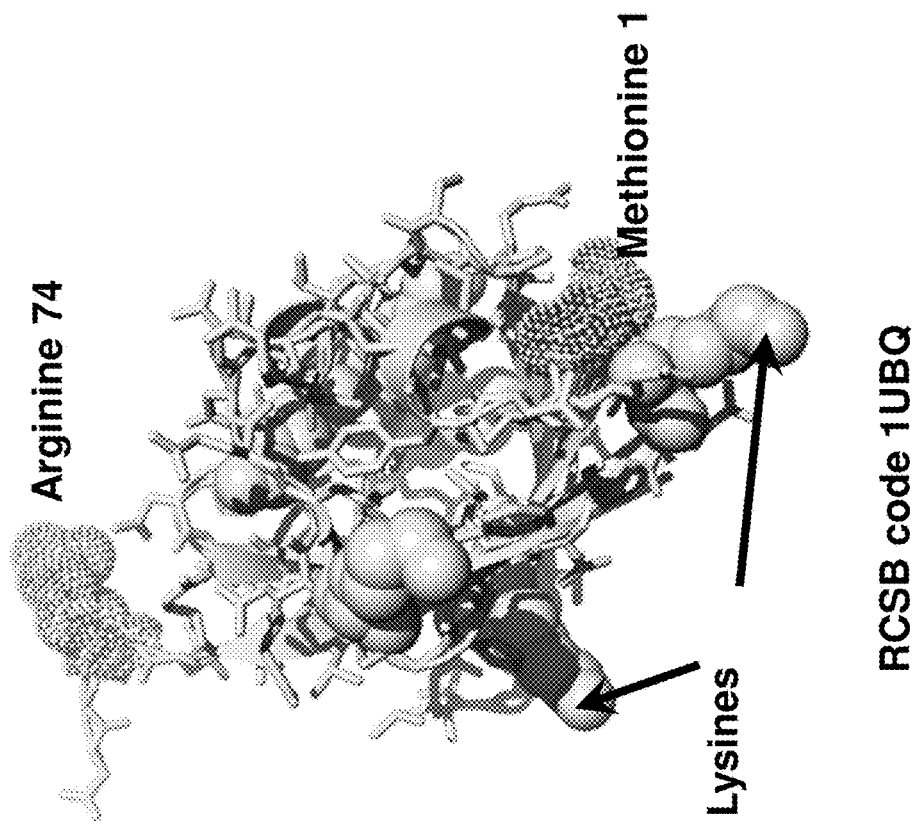
FIG. 3 shows a three dimensional representation of a Ubiquitin protein for use as a protein shield.

When described, in what follows, are certain features of the invention where a list of potential choices can and have been set out below, see for example the number of dyes moieties and nucleotide moieties in a nucleotide analog, the reader is instructed to understand that this is purely in the interests of conciseness and that any one of the exemplary features in any one of said paragraphs can be combined with any other of the exemplary features in any other of said paragraphs in any combination the skilled person chooses. This specification is to be construed accordingly.

In single-molecule real-time sequencing using fluorescence detection, the enzyme is illuminated with excitation light while a sequencing reaction is taking place. In some cases, the illumination results in photodamage which damages or kills the polymerase enzyme. This damage can cause the sequencing reaction to end, resulting in shorter read lengths than desired. The inventors have performed experiments which demonstrate that significantly longer read lengths can in some cases be obtained in the dark than can be obtained for the same sequencing reaction under illumination. The inventors have also performed experiments which indicate that damage to the enzyme under illumination can be accompanied by the formation of a covalent bond between a fluorescent dye moiety on a nucleotide analog and the polymerase enzyme. Thus, it is believed that the stability of the enzyme can be compromised when there is contact between the enzyme and a fluorescent moiety on a nucleotide analog which is in the active site of the enzyme. In some cases, it appears that this mechanism constitutes the dominant mode of degradation.

The inventors have found that photodamage can be mitigated and sequencing readlengths improved by incorporation of a shielding protein into a nucleotide analog. The nucleotide analog is constructed such that the shielding protein is disposed between the nucleotide phosphate portion and the fluorescent dye portion of the nucleotide analog. The size and position of the protein are chosen such that the fluorescent dye portion of the analog does not come into contact with the polymerase enzyme when the nucleotide portion is held within the active site of the polymerase. Preventing contact between the fluorescent dye and the polymerase prevents the formation of a covalent bond to the polymerase. By shielding the enzyme from contact with the fluorescent dye, the protein blocks a significant photodamage pathway, resulting in longer enzyme life under illumination.

The nucleotide (nucleoside phosphate) portion of the analog is attached to the shielding protein through the polyphosphate portion of the nucleotide. With this type of attachment, when the nucleotide monophosphate portion of the nucleotide analog is incorporated into the growing nucleic acid strand, the portion of the nucleotide analog having the shielding protein and the fluorescent dye is cleaved from the portion of the nucleotide that gets cleaved, and it diffuses away to allow for incorporation of the next nucleotide into the chain without interference with these moieties.

FIG. 1 shows a schematic illustration of the incorporation of a shielding protein into a nucleotide analog. FIG. 1A illustrates real time single molecule sequencing with a conventional nucleotide analog. The polymerase enzyme 110 is bound to the surface of a substrate, such as a chip, 160, for example with a linker 150. The polymerase enzyme 110 is complexed with a template nucleic acid having a template strand 120 and a primer/growing strand 130. Sequencing is performed by observing the enzyme while it is incorporating nucleotides into the growing strand. The nucleotide analog that gets incorporated into the growing strand generally spends more time in the active site than a nucleotide analog that does not get incorporated, allowing for the identification of the incorporated nucleotide. When an incorporation takes place, the nucleoside monophosphate portion of the nucleotide analog is incorporated into the growing chain, and the remainder of the nucleotide analog including the fluorescent label is cleaved away and the enzyme is ready for the next incorporation. By watching the incorporation of bases over time, the sequence of the template nucleic acid 120 can be determined by determining the series of nucleotides that are incorporate into the growing strand 130. In the embodiment described here, the polymerase enzyme complex is tethered to a substrate. It can be advantageous for the polymerase enzyme complex to remain in one discrete region of space over the sequencing reaction to assist in optically observing the complex over time. While here, the complex is described as attached to a substrate surface, there are other ways to provide restricting the movement of the polymerase complex such as the use of gels, or the use of discrete volumes.

FIG. 1(A) shows a conventional nucleotide analog 140, held in the enzyme prior to incorporation. The nucleotide portion of the analog 144 is held in the active site of the enzyme in position for incorporation. FIG. 1(A)(2) illustrates that while the nucleotide analog is associated with the enzyme, the fluorescent moiety 142 can come into contact with the enzyme. During this process, the enzyme is illuminated with excitation light to allow for observation of the fluorescent moiety. When the fluorescent moiety absorbs the excitation light, it enters into an excited state. It is believed that having the excited fluorescent moiety in the vicinity of the enzyme, and in particular in when the fluorescent moiety comes into contact with the enzyme, damage to the enzyme can result, adversely affecting the sequencing reaction. The damage to the enzyme can result in slowing the enzyme, altering its effectiveness, or in completely halting the polymerase reaction. Applicants note that in some cases the term substrate is used to refer to an "enzyme substrate" such as a nucleotide analog, and that in some cases, the term substrate is used to refer to a solid support. Which type of "substrate" is being referred to will be clear from the context of the use of the term and should be understood by one of ordinary skill in the art.

FIG. 1(B) shows a nucleotide analog or polymerase enzyme substrate of the invention 170 having a shielding protein 176. Sequencing can be carried out with analogs having shielding proteins by the same processes described above for conventional nucleotide analogs. As with a conventional enzyme substrate, the nucleotide portion 174 of the analog is held in the active site of the enzyme prior to incorporation. The nucleotide analog of the invention has a nucleotide portion 174 connected to the shielding protein through the phosphate portion of the nucleotide. In some cases, the nucleotide is attached to the protein through a linker group 179. A fluorescent moiety is attached to the shielding protein, in some cases through a linking group 178. FIG. 1(B)(2) illustrates that the shielding protein 176 prevents contact between the polymerase enzyme and the fluorescent dye moiety 172. By shielding the enzyme from contact with the fluorescent dye moiety while the nucleotide portion of the analog is in the active site of the enzyme, the enzyme is protected from photodamage due to contact with the fluorescent moiety's excited state. While the usefulness of the nucleotide analogs of the invention is illustrated with the description above of SMRT sequencing, it is to be understood that these analogs can be used with any suitable sequencing method.

There are several structural features that can be used to inhibit or prevent the florescent dye from coming into contact with the polymerase enzyme when the nucleotide portion of the nucleic acid analog is in the active site. One feature is the size of the shielding protein. The shielding protein generally has greater than about 60 amino acids. The shielding protein can be greater than about 80 amino acids. The shielding protein can be greater than about 200 amino acids. In some cases the shielding protein has from about 60 amino acids to about 2,000 amino acids. In some cases it has from about 60 amino acids to about 1,000 amino acids. In some cases it has from about 80 amino acids to about 600 amino acids.

Another feature that can be used to prevent contact between the fluorescent moiety and the polymerase enzyme is the distance between the points of attachment of the nucleotide portion and the fluorescent dye portion of the nucleotide analog. The attachment point for the fluorescent moiety and the nucleotide are generally distal from each other on the enzyme. In some cases, the attachment points are 2 nm apart or greater. In some cases the attachment point is 4 nm apart or greater. The distance between the attachment points can be either through space, or can be the distance across the surface of the protein. The distance through space can be determined by modeling the three dimensional structure of the protein. Current modeling software can accurately describe the 3 dimensional structure of proteins. In some cases, these models can be informed by X-ray crystal structure and/or X-ray or neutron scattering to improve the accuracy. In some cases, the distance between the attachment point of the nucleotide and the attachment point of the fluorescent moiety is greater than one quarter of a distance around the protein. In some cases, the distance between the attachment points is greater than a third of a distance around the protein. A distance around the protein can be determined, for example by obtaining a structure of the protein, treating the structure of the protein as an ellipsoid, and tracing an ellipse around the ellipsoid including the points of attachment.

In accordance with the shielding aspects of the invention, it is desirable to have the attachment points of a nucleotide component and a dye component on the protein be spaced apart. This spacing can be described by a three-dimensional (through space) distance between attachment points, or by a distance over the surface of a protein between attachment points. Another way of characterizing the distance between the attachment points is in terms of linear distance between attachment points on the primary sequence of the protein. We have found, for example, that it is typically desirable that the linkages be at least about 20 amino acid units apart for a protein of at least 60 amino acids. In some cases it is desirable that the linkages be at least about 30 amino acids apart in the primary sequence.

Another feature that can be used to prevent contact between the fluorescent moiety and the polymerase enzyme is the length and the flexibility of a linker between the fluorescent moiety and the protein and a linker between the nucleotide and the protein. Such linkers are not required but can be used to attach the various portions of the nucleotide analog. FIG. 1(B) shows linker 178 between the fluorescent moiety 172 and the shielding protein, and optional linker 179 between the nucleotide and the shielding protein. The linkers can comprise any suitable subunits. Examples of linkers are provided in more detail herein. The length of the linker is chosen such that, taking into account the shortest distance between attachment points on the shielding protein, that the dye will be prevented from contacting the polymerase enzyme when the nucleotide moiety is in the active site of the enzyme.

One of skill in the art is able to determine that a particular structure will prevent contact of the fluorescent dye with the polymerase enzyme. For example, computer based or physical molecular models can be constructed that describe the extent of movement of a particular moiety within an ensemble of molecules. In some cases, knowledge of a protein structure, for example from x-ray crystallography combined with a knowledge of molecular dimensions of sub-structures can be combined to determine whether contact between the fluorescent dye and the polymerase enzyme will occur. As used in this context, preventing contact between the fluorescent dye and the polymerase enzyme means that under the conditions of the sequencing reaction, contact will occur, if at all, only very rarely, to the extent that such contact would not lead to discernable photodamage events.

We have found that in some cases it is advantageous to provide nucleotide analog constructs having more than one fluorescent moiety and/or more than one nucleotide moiety. For example, having multiple dye moieties. In some cases the polymerase enzyme substrate or nucleotide analog has 1 to 10 fluorescent dye moieties. In some cases the analog has 1 to 4 fluorescent dye moieties. In some cases the analog has 1, 2, 3, 4, 5, 6, 7, or 8 fluorescent dye moieties. In some cases the analog has at least 1, 2, 3, 4, 5, 6, 7, or 8 fluorescent dye moieties. In some cases the polymerase enzyme substrate or nucleotide analog has 1 to 10 fluorescent nucleotide moieties, in some cases the analog has 1 to 4 nucleotide moieties. In some cases the analog has 1, 2, 3, 4, 5, 6, 7, or 8 nucleotide moieties. The nucleotide analog of the invention can have any suitable combination of 1 to 10 fluorescent dye moieties and 1 to 10 nucleotide moieties.

In some cases, each of the moieties is attached to a different attachment point on the protein. In some cases, an attachment point on the shielding protein branches out to have multiple dyes or multiple nucleotides. In some cases, a single dye or single nucleotide can have multiple attachment points. Any suitable combination of dyes and attachment points, or nucleotides and attachment points can be used.

FIG. 2 shows various exemplary nucleotide analogs of the invention. In each case, the nucleotide moieties 230 are represented by triangles, and the fluorescent dye moieties 210 are represented by hexagons. In each case the moieties are attached to a shielding protein 220. The moieties can be attached using linkers or they can be attached directly to the proteins. Generally, covalent attachment of the moieties is preferred, but in some cases, the affinity binding of a protein can be used for attachment of one or more of the moieties. For example, in some cases, a protein such as avidin or streptavidin can be used, and the protein's affinity for biotin can be used to attach a moiety to the protein. FIG. 2(A) shows a nucleotide analog having one nucleotide moiety and one fluorescent moiety. FIG. 2(B) shows a nucleotide analog having on nucleotide moiety and two fluorescent moieties. Multiple dyes can result a brighter analog. In addition, different dyes can be used to provide different color combinations. In addition dyes which have FRET interactions can be used to provide higher brightness, and a larger Stokes shift (wavelength difference between excitation and emission). FIG. 2(C) shows a nucleotide analog having two nucleotide moieties and one dye moiety. Having multiple nucleotide analogs can be used to raise the effective concentration of nucleotide. For instance having a higher number of nucleotide moieties can result in a faster reaction rate at a given concentration of analog, or can be used to produce the same reaction rate at a lower concentration of analog. FIGS. 2 (D) through 2(L) provide various combinations of nucleotide moieties and fluorescent dye moieties that allow for optimizing the levels of brightness and effective concentration. In some cases each of the moieties is attached directly to the shielding protein. In some cases, an attachment point will be linked to multiple moieties. FIG. 2(D) shows a nucleotide analog of the invention having two fluorescent moieties and two nucleotide moieties, each moiety attached at a different place on the protein. FIG. 2(E) shows a nucleotide analog of the invention having two fluorescent moieties and three nucleotide moieties, each moiety attached at a different place on the protein. FIG. 2(F) shows a nucleotide analog of the invention having three fluorescent moieties and two nucleotide moieties, each moiety attached at a different place on the protein. FIG. 2(G) shows a nucleotide analog of the invention having three fluorescent moieties and three nucleotide moieties, each moiety attached at a different place on the protein. FIG. 2(H) shows a nucleotide analog of the invention having two fluorescent moieties and one nucleotide moieties, the two fluorescent moieties connected to the same attachment point on the protein. FIG. 2(I) shows a nucleotide analog of the invention having two fluorescent moieties and two nucleotide moieties, the two fluorescent moieties connected to the same attachment point on the protein, and the two nucleotide moieties connected to a second attachment point on the protein. FIG. 2(J) shows a nucleotide analog of the invention having two fluorescent moieties and two nucleotide moieties, the two fluorescent moieties connected to the same attachment point on the protein, and the two nucleotide moieties are each connected to a different attachment point on the protein. FIG. 2(K) shows a nucleotide analog of the invention having three fluorescent moieties and two nucleotide moieties, the three fluorescent moieties connected to the same attachment point on the protein, and the two nucleotide moieties connected to a second attachment point on the protein. FIG. 2(L) shows a nucleotide analog of the invention having four fluorescent moieties and two nucleotide moieties, two of the fluorescent moieties are connected to one attachment point on the protein, the other two fluorescent moieties are connected to a second attachment point, and the two nucleotide moieties connected to a third attachment point on the protein. It will be understood from the description and the drawings that there are many other combinations of multiple fluorescent moieties and nucleotide moieties that can be used with the instant invention. In addition to compounds of the invention having multiple moieties attached to a single attachment point on a shielding protein, in some cases, a single moiety can be attached to the protein shield through multiple attachment points.

The attachment of the nucleotide and fluorescent moieties to the shielding proteins can be by any suitable means. In preferred embodiments, the moieties are covalently linked to the proteins. While in some cases affinity pair linkages can be useful in the invention, we have found that covalent linkages are often preferred due to their stability and consistency. In sequencing systems, there will often be four different nucleotide analogs, each having one of four bases (e.g. A, G, C, T, or A, G, C, U). For consistent sequencing results, it is desired to have a set of nucleotide analogs that can be readily purified, for which quality control experiments can be readily performed, and which will be stable over time without dissociation or rearrangement. Covalently linked structures can meet these criteria.

Covalent linkage of moieties to proteins is well known in the art. The reactive groups on various amino acids can be used to provide specific sites of attachment. Reactive groups for the attachment of moieties to the protein include amine groups on lysine or arginine, the thiol group on cysteine, the acid group on aspartic acid or glutamic acid, and the hydroxyl group on serene or threonine. In some cases, an available protein will have appropriate residues for connection of the moieties. In other cases, the appropriate residues can be engineered into the protein. Using genetic engineering to produce a desired protein having various amino acids removed or added is a common and well understood practice.

The different reactivity of different groups on the protein can be used to direct specific moieties to different attachment points on the protein. For example, a nucleotide moiety can be connected to a specific cysteine at one desired attachment point, and a fluorescent moiety can be attached to a lysine at a second attachment point. In some cases, the same type of residue will have different reactivity due to where it resides on the protein, allowing selective attachment. For example, a protein may have three lysine moieties where each has a different reactivity. Attachment can be carried out such that only the most reactive lysine is modified, or alternatively, attachment can be carried out by protecting the two most reactive lysines, then reacting the moiety of interest with the third, least reactive lysine.

There are many types of chemical reactions that can be used to react with specific amino acid residues on proteins. For example, coupling through the cysteine thiol can be accomplished using a reaction with maleimide. Cysteine groups can also be coupled with allylic halides, phenylmethyl halides, alkyl halides, or alpha-halo carbonyl groups. Amine groups can be coupled to activated carboxylates or activated sulfonic acids. Amine or carboxylate functionality on the protein can be used to produce amide linkages. Linkages containing nitrogen double bonds such as oxime or hydrazones can be used. Highly selective linkages can be formed using cycloaddition chemistry such as the Huisgen 1,3-dipolar azide-alkyne cycloaddition. See e.g. Advances in Bioconjugation, Kalia, J, Raines, R. T., Curr Org Chem. 2010 January; 14(2): 138-147, Besanceney-Webler et al., "Increasing the Efficacy of Bioorthogonal Click Reactions for Bioconjugation" Angew. Chem. Int. Ed. 2011, 50, 8051-8056, and DiMarco et al. International Journal of Nanomedicine, December 2009, 37-49.

The moieties can be attached to the shielding protein through unnatural amino acids that are introduced into the protein, allowing for specific attachment chemistry. See, for example, the work of Peter Schultz, e.g. Noren et al., "A general method for site-specific incorporation of unnatural amino acids into proteins", Science, 244:182-188, 1989, and Ellman et al. "Biosynthetic method for introducing unnatural amino acids site-specifically into proteins", Methods in Enzymology, Volume 202, 1991, Pages 301-336.

Many other methods of chemically modifying proteins are known in the art. See e.g. "Chemical modification of proteins at cysteine: opportunities in chemistry and biology" Chalker J M, Bernardes G J, Lin Y A, Davis B G, Chem Asian J. 2009 May 4; 4(5):630-40, "Chemoselective ligation and modification strategies for peptides and proteins" Hackenberger C P, Schwarzer D. Angew Chem Int Ed Engl. 2008; 47(52):10030-74, "Chemoselective modification of proteins: hitting the target", Carrico I S, Chem Soc Rev. 2008 July; 37(7):1423-31, "Modification of tryptophan and tryptophan residues in proteins by reactive nitrogen species", Yamakura F, Ikeda K, Nitric Oxide. 2006 March; 14(2):152-61, Chemical modification of proteins, Cane A F, Methods Mol Biol. 1994; 32:311-20, Selective chemical modification of proteins, Shaw E, Physiol Rev. 1970 April; 50(2):244-96, and "Chemical reagents for protein modification" By Roger L. Lundblad, CRC Press, 2004.

Reactive functional groups can be used to attach the moieties to the shielding proteins and to attach moieties to linkers and linkers to proteins. Reactions for this purpose and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
(a) carboxyl groups and derivatives thereof including, but not limited to activated esters, e.g., N-hydroxysuccinimide esters, N-hydroxyphthalimide, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;
(b) hydroxyl groups, which can be converted to esters, sulfonates, phosphoramidates, ethers, aldehydes, etc.
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, allowing derivatization via formation of carbonyl derivatives, e.g., imines, hydrazones, semicarbazones or oximes, or via such mechanisms as Grignard addition or alkyllithium addition;
(f) sulfonyl halide groups for reaction with amines, for example, to form sulfonamides;
(g) thiol groups, which can be converted to disulfides or reacted with acyl halides, for example;
(h) amine or sulfhydryl groups, which can be, for example, acylated, alkylated or oxidized;
(i) alkenes, which can undergo, for example, cycloadditions, acylation, Michael addition, etc;
(j) epoxides, which can react with, for example, amines and hydroxyl compounds; and
(k) phosphoramidites and other standard functional groups useful in nucleic acid synthesis.

The reactive functional groups can be chosen such that they do not participate in, or interfere with, the reactions necessary to assemble or utilize the nucleotide analogue. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

The shielding proteins can be modified, for example at the C-terminal and/or N-terminal region of the protein. For example, the one or more modifications can be a polyhistidine tag, a HIS-10 tag, a HIS-6 tag, an alanine tag, an Ala10 tag, an Ala 16 tag, a biotin tag, a GST tag, a BiTag, an S Tag, a SNAP-tag, an HA tag, a DSB (Sso7D) tag, a lysine tag, a NanoTag, a Cmyc tag, a tag or linker comprising the amino acids glycine and serine, a tag or linker comprising the amino acids glycine, serine, alanine and histidine, a tag or linker comprising the amino acids glycine, arginine, lysine, glutamine and proline, a plurality of polyhistidine tags, a plurality of HIS-10 tags, a plurality of HIS-6 tags, a plurality of alanine tags, a plurality of Ala10 tags, a plurality of Ala16 tags, a plurality of biotin tags, a plurality of GST tags, a plurality of BiTags, a plurality of S Tags, a plurality of SNAP-tags, a plurality of HA tags, a plurality of DSB (Sso7D) tags, a plurality of lysine tags, a plurality of NanoTags, a plurality of Cmyc tags, a plurality of tags or linkers comprising the amino acids glycine and serine, a plurality of tags or linkers comprising the amino acids glycine, serine, alanine and histidine, a plurality of tags or linkers comprising the amino acids glycine, arginine, lysine, glutamine and proline, biotin, avidin, one or more Factor Xa sites, one or more enterokinase sites, thrombin sites, antibodies or antibody domains, antibody fragments, antigens, receptors, receptor domains, receptor fragments, ligands, or combinations thereof.

The protein can include one or more modifications at both the C-terminal and N-terminal regions of the polymerase, where such features at the C-terminal and N-terminal regions are optionally the same, e.g., a polyhistidine tag (e.g., a His10 tag) at both the C-terminal and N-terminal regions. Polymerases that include exogenous or heterologous features at both the C-terminal and N-terminal regions optionally include a B-Tag and a polyhistidine tag (e.g., a B-Tag at the N-terminal region and a polyhistidine tag (e.g., a His-10 tag) at the C-terminal region). Polymerases that include a B-Tag and a polyhistidine tag can further include a Factor Xa recognition site. Any of these modifications can be used as sites for attachment of one or more moieties.

The shield protein can comprise the protein ubiquitin. Ubiquitin is a small regulatory protein that has been found in almost all tissues of eukaryotic organisms. A variety of different modifications can occur. The ubiquitin protein has about 76 amino acids and has a molecular mass of about 8.5 kDa. It is highly conserved among eukaryotic species: Human and yeast ubiquitin share 96% sequence identity. Any suitable ubiquitin protein can be used as the shield protein or as part of a shield protein. For example the human ubiquitin 1 UBQ can be used as a shield protein by coupling nucleotides to reactive groups on the protein as described herein. The tertiary structure of ubiquitin has well separated termini, allowing for attachment of one or more nucleotides at one terminus, and one or more dyes at the other terminus to provide separation and shielding. For example, mutation of the native lysines to arginines results in a unique reactive amine at the N-terminus, and addition of a cysteine residue near the C-terminus provides a unique reactive thiol. See, e.g. Vijay-Kumar, S., Bugg, C. E., Cook, W. J., (1987) J. Mol. Biol. 194: 531-544 incorporated herein by reference in its entirety for all purposes. In some cases the ubiquitin will have a his tag such as a hexa-his tag at its N or its C terminus.

FIG. 3 shows an image representing the three dimensional structure of ubiquitin 1 UBQ. An arginine close to the C-terminus and the N-terminal methionine are indicated as dotted spheres. The locations of the lysines are shown as spheres. All other amino acids are shown as sticks, and the backbone is represented as a ribbon.

A sequence for ubiquitin is provided in SEQ ID NO: 1 below:

SEQ ID NO: 1
MQIFVKTLTGKTITLEVEPSDTIENVKAKIQDKEGIPPDQQRLIFAGKQL

EDGRTLSDYNIQKESTLHLVLRLRGG

One useful construct to segregate dye and nucleotide involves mutating all the lysines to arginines, and mutating the arginine at position 74 to a cysteine (R74C). This would leave a unique primary amine at the N-terminal Met1, and a unique thiol at position 74. Table 1 shows some ubiquitin mutants useful as protein shields.

Figure 4:
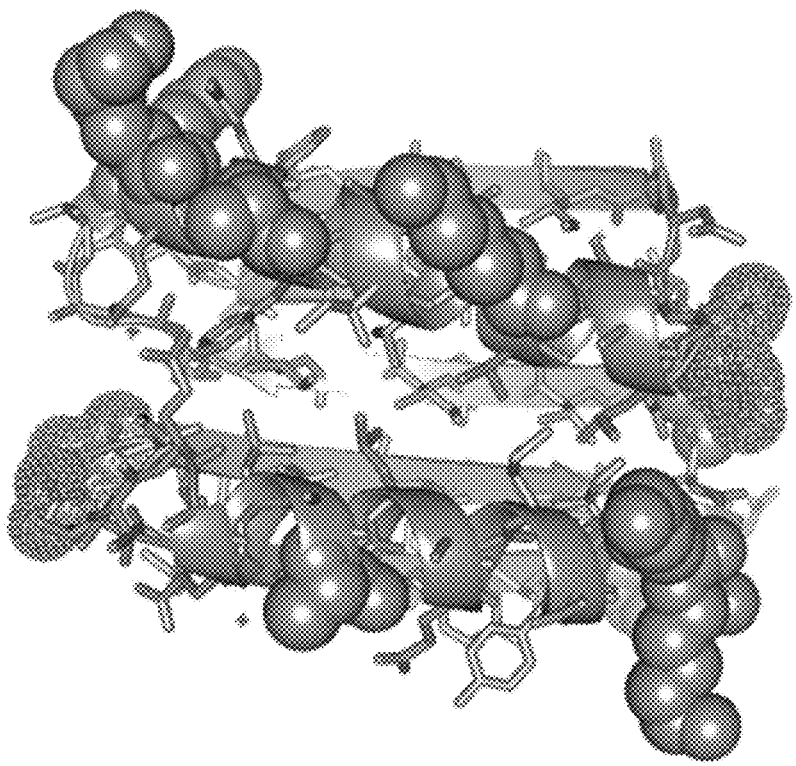
FIG. 4 shows a three dimensional representation of a TOP7 protein for use as a protein shield.

TABLE 1 pET11a.His6co.Ubiquitin.co
pET11.His6co.ENLYFQS.Ubiquitin.K6R_K11R_K27R_K29R_K33R_K48R_K63R_R74C.co
pET11.His6co.ENLYFQSG.Ubiquitin.K6R_K11R_K27R_K29R_K33R_K48R_K63R_R74C.co
pET11a.His6co.Ubiquitin.K29R_K48C_K63R_77D.co
pET11a.His6co.Ubiquitin.K29C_K48C_K63C.co
pET11.His6co.Ubiquitin.K6E_K11R_K27R_K29R_K33R_K48R_K63R_R74C.co
pET11.His6co.Ubiquitin.K6R_K11R_K27R_K29R_K33R_R42E_K48R_K63R_R74C.co
pET11.His6co.Ubiquitin.K6E_K11R_K27R_K29R_K33R_R42E_K48R_K63R_R74C.co
pET11.His6co.Ubiquitin.K6R_K11R_K27R_K29R_K33R_K48R_K63R_R74C.co
pET11.His6co.Ubiquitin.R74C.co The protein TOP7 can also be used as a protein shield or a portion of a protein shield. Top7 is an artificial 93-residue protein, which was designed to have a unique fold not found in nature. See Kuhlman et. al., (2003 Nov. 21). "Design of a novel globular protein fold with atomic-level accuracy". Science 302 (5649): 1364-1368, U.S. patent application Ser. No. 12/429,930, and U.S. Pat. No. 7,574,306, each incorporated herein by reference in their entirety for all purposes. FIG. 4 shows a three dimensional representation of TOP7 protein. Lysines are shown as spheres; the N- and C-terminal residues that are visible in the structure are shown as dotted spheres. As described above, the various residues can be mutated to allow for specific attachment of one or more dyes or one or more nucleotides to the protein.

A sequence for TOP7 is provided in SEQ ID NO:2 below:

SEQ ID NO: 2
MGDIQVQVNIDDNGKNFDYTYTVTTESELQKVLNELMDYIKKQGAKRVRI

SITARTKKEAEKFAAILIKVFAELGYNDINVTFDGDTVTVEGQLEGGSLE

HHHHHH

Representative TOP7 mutants are shown below in Table 2.

thermostable Seryl tRNA synthetase from *Pyrococcus horikoshii* (PKSERRS) as shown in its crystal structures (for example, Protein Data B ank database ID 2ZR2). The coiled-coil domain of Seryl tRNA synthetases can be transplanted into different protein scaffolds, as shown by the crystal structure of dynein-SeryltRNA synthetase (Protein Data Bank ID 3ERR). A stable helix in solution can be generated by using a repeat of the sequence EAAAR (Huyghes-Despointes, et al. 1993).

Particularly useful proteins protein shields for the invention include avidin protein including avidin, streptavidin, tamavidin, traptavidin, xenavidin, bradavidin, AVR2, AVR4, and homologs thereof. In some cases the monomeric, dimeric, or tetrameric forms can be used. In particular, the tetrameric form of the avidin protein in combination with bis-biotin linked dye components and/or nucleotide components are useful in protein shielded nucleotide analogs. In some cases, glycosylation variants of the avidin proteins are used.

Figure 5:
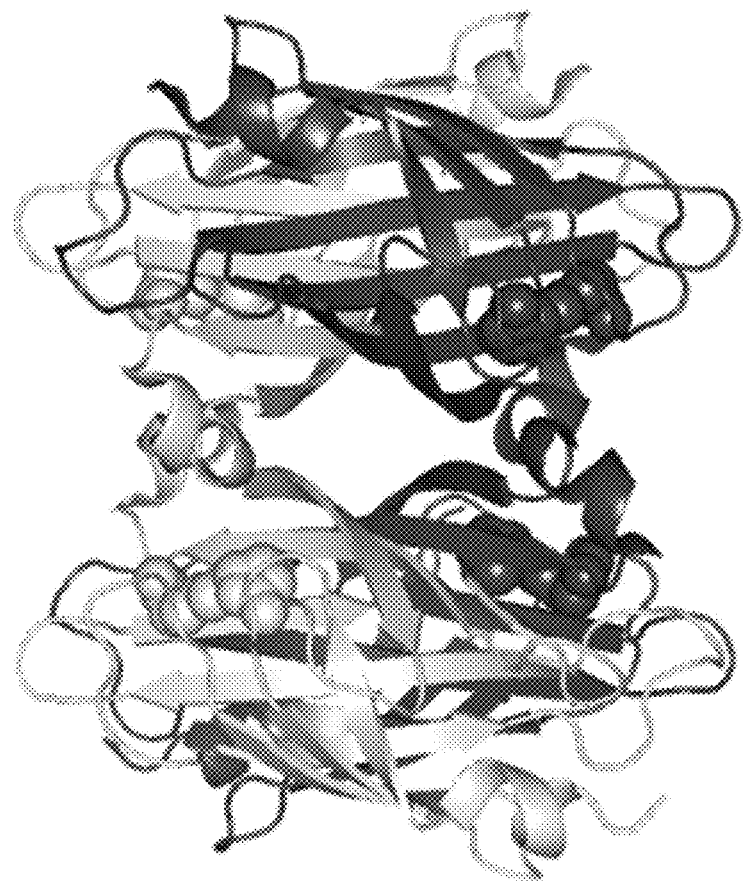
FIG. 5 shows a three dimensional representation of a Tamavidin protein for use as a protein shield.

The protein shield of the invention can be based on or include the protein tamavidin and its homologs. Tamavidin is a fungal avidin-like protein that binds biotin with high affinity. FIG. 5 shows a crystal structure of the tetrameric form of tamavidin, with two subunits shown in dark, and two in light, gray. The biotins are shown in sphere representation. See e.g. RCSB Protein Data Bank protein code 2ZSC and Takakura, et al., Journal: (2009) 276: 1383-1397, incor-

TABLE 2 pET11a.TOP7.co.His6co
pET11a.TOP7.K15R_K31R_K41R_K42R_K46R_K57R_K58R_K62R_K69R_100.1C.co.His6co
pET11a.BtagV07co.TOP7.100.1C.co.His6co
pET11a.TOP7.K15R_K41R_K42R_K46R_K62R_K69R_110.1C.co.His6co
pET11a.TOP7.K15R_K46R_R49C.co.His6co
pET11a.TOP7.100.1C.co.His6co
pET11.TOP7(1-100).AAAR.(EAAAR)8.TOP7_2(1-
100).K15R_K31R_K41R_K42R_K46R_K57R_K58R_K62R_K69R_100.1C.His6co
pET11.TOP7(1-100).AAAR.(EAAAR)8.C.His6co
pET11.TOP7(1-
100).K15R_K31R_K41R_K42R_K46R_K57R_K58R_K62R_K69R.AAAR.(EAAAR)8.TOP7_2(1-
100).K15R_K31R_K41R_K42R_K46R_K57R_K58R_K62R_K69R_100.1C.His6co
pET11.TOP7(1-
100).K15R_K31R_K41R_K42R_K46R_K57R_K58R_K62R_K69R.AAAR.(EAAAR)8.C.His6co
pET11.TOP7(1-100).PKSERRS(32-
100).K35R_K43R_K45R_K56R_K63R_K66R_K67C_K83R_K96R_K97R_K98R.His6co
pET11.TOP7(1-100).K15R_K31R_K41R_K42R_K46R_K57R_K58R_K62R_K69R.PKSERRS(32-
100).K35R_K43R_K45R_K56R_K63R_K66R_K67C_K83R_K96R_K97R_K98R.His6co
pET11.TOP7(1-13).GG.PKSERRS(32-
100).K35R_K43R_K45R_K56R_K63R_K66R_K67C_K83R_K96R_K97R_K98R.K15R_K31R_K41R_
K42R_K46R_K57R_K58R_K62R_K69R.GG.TOP7(14-104).His6co Coiled-coils of alpha helices, or single, stable alpha helices, provide particularly efficient means by which to generate two widely separated points of attachment in a protein scaffold. An example of a coiled-coil is provided by porated herein by reference in its entirety. Tamavidin may be mutated for example the C135 can be mutated in case the cysteine would have some unwanted reactivity. In some cases tamavidin will be constructed to have his tag at its N or C terminus. Tamavidin can be advantageous in that it can be more stable than streptavidin and can be more soluble in *E. coli* expression.

Sequences of the monomeric protein that makes up the tetrameric tamavidin proteins (Tam1 SEQ ID NO:3 and Tam2 SEQ ID NO:4) are listed below.

```
                                         SEQ ID NO: 3
MKDVQSLLTGTWYNELGSTMNLTANKDGSLTGTYHSNVGEVPPTYHLSGR

YNLQPPSGQGVTLGWAVSFENTSANVHSVSTWSGQYFSEPAEVILTQWLL

SRSSEREDLWQSTHVGHDEFSKTKPTKEKIAQAQLLRRGLKFE
                                         SEQ ID NO: 4
MSDVQSSLTGTWYNELNSKMELTANKDGTLTGKYLSKVGDVYVPYPLSGR

YNLQPPAGQGVALGWAVSWENSKIHSATTWSGQFFSESSPVILTQWLLSS

STARGDVWESTLVGNDSFTKTAPTEQQIAHAQLHCRAPRLK
```

One useful particularly avidin protein is streptavidin, and in particular in the tetrameric form. A sequence of the monomer that associates to form the tetrameric form of streptavidin is provided in SEQ ID NO:5 below:

```
                                         SEQ ID NO: 5
MEAGITGTWYNQLGSTFIVTAGADGALTGTYESAVGNAESRYVLTGRYDS

APATDGSGTALGWTVAWKNNYRNAHSATTWSGQYVGGAEARINTQWLLTS

GTTEANAWKSTLVGHDTFTKVKPSAAS
```

Figure 6:
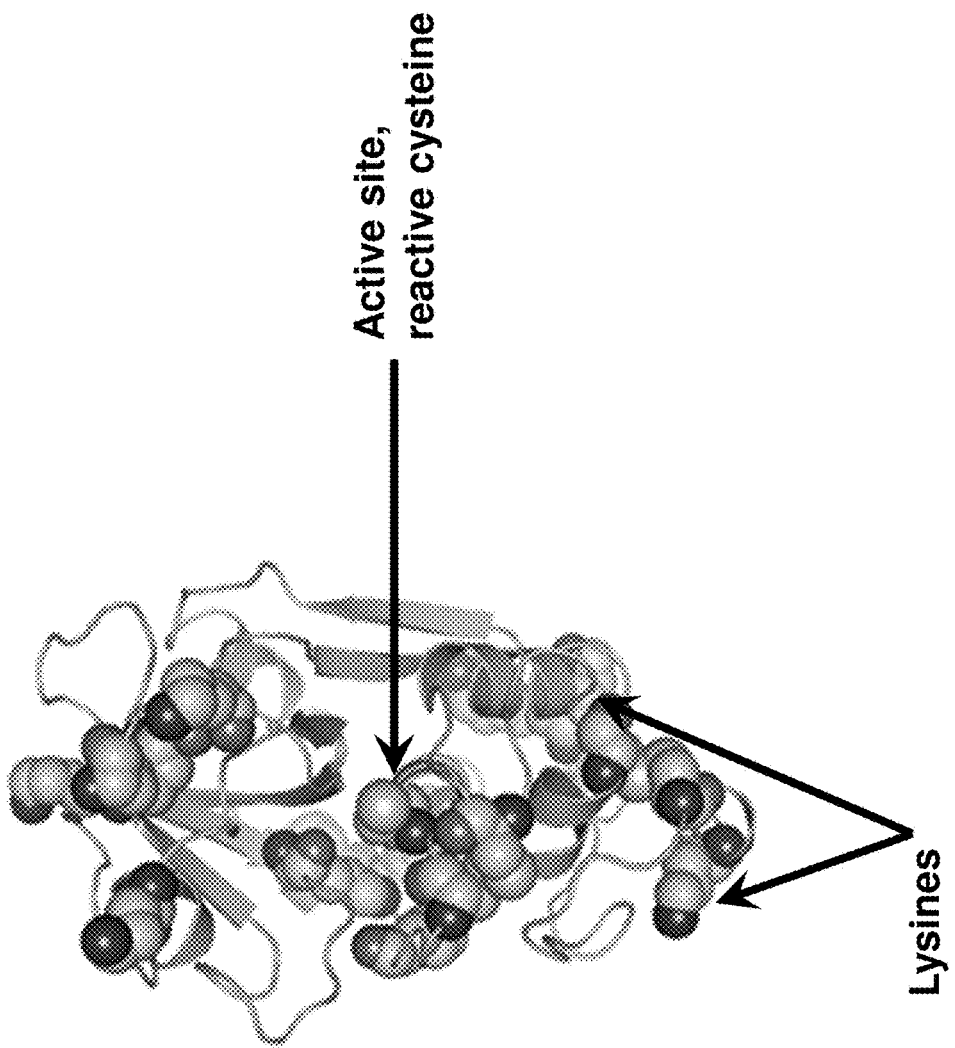
FIG. 6 shows a three dimensional representation of a Papain protein for use as a protein shield.

Papain also provides a protein structure for use as a protein shield or as part of a protein shield. Papain, also known as papaya proteinase I, is a cysteine protease enzyme present in papaya. Proteins in the papain family, which are present in many species can also be used as protein shields. FIG. 6 shows a representation of papain indicating the position of lysines and of a reactive cysteine in the active site. As described above, amino acid sites can be mutated to provide the appropriate sites for attachment of dye and nucleotide components.

Figure 7:
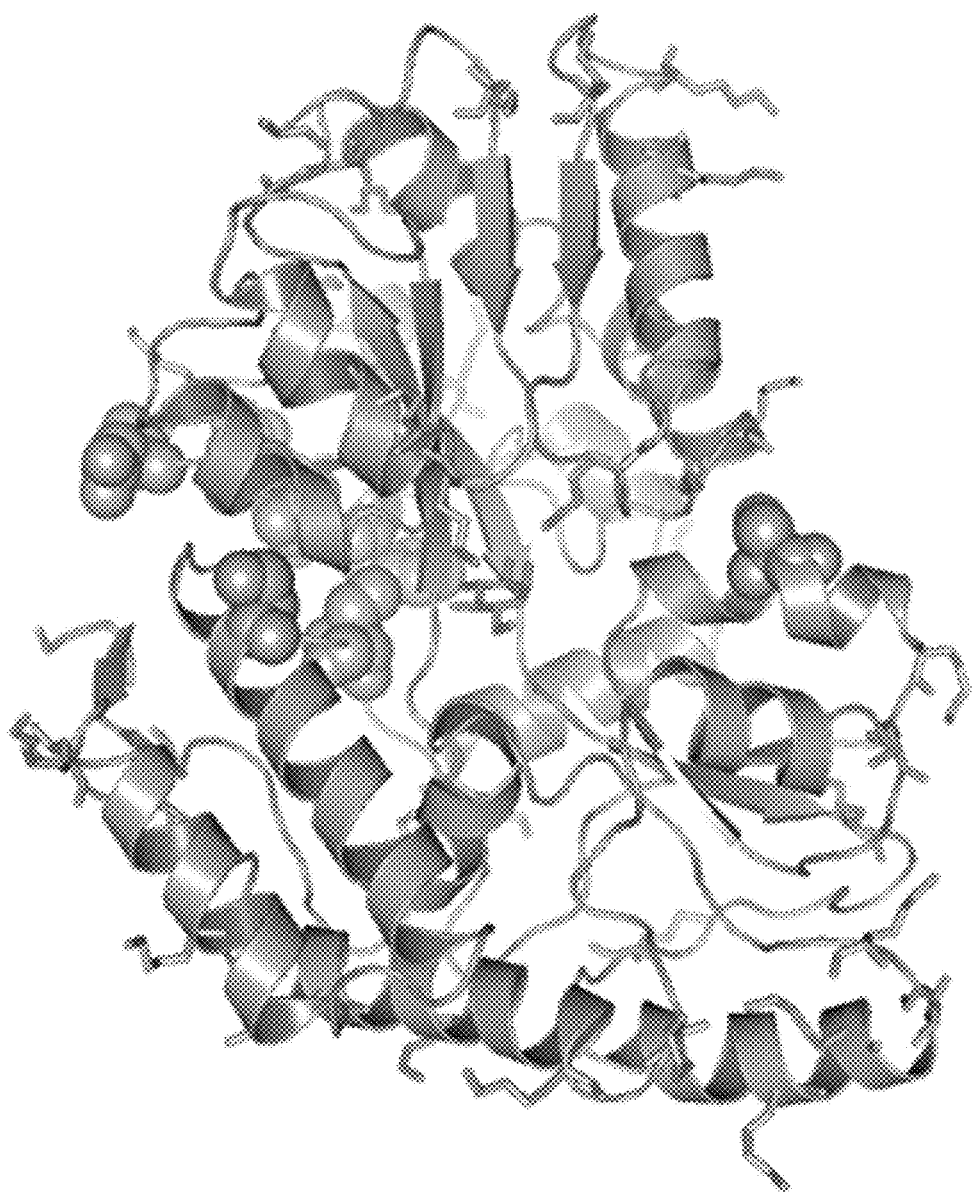
FIG. 7 shows a three dimensional representation of a Maltose Binding Protein for use as a protein shield.

Another suitable protein for use as a protein shield is maltose binding protein. Maltose binding protein is a part of the maltose/maltodextrin system of *Escherichia coli*, which is responsible for the uptake and efficient catabolism of maltodextrins. Maltose binding protein has an approximate molecular mass of 42.5 kilodaltons. FIG. 7 shows a three dimensional representation of maltose binding protein with lysines shown in stick figures. Wild type maltose binding protein has no cysteines; some residues that have been mutated in the literature to generate cysteines are shown as spheres. Table 3 shows some suitable constructs for maltose binding protein. These constructs without the his-tag can also be useful. These constructs contain multiple naturally occurring lysines along with literature based unique engineered cysteines.

TABLE 3 pET11.His10co.MBP.co
pET11.His10co.MBP.S337C.co
pET11.His10co.MBP.N100C.co
pET11.His10co.MBP.S233C.co

Figure 8:
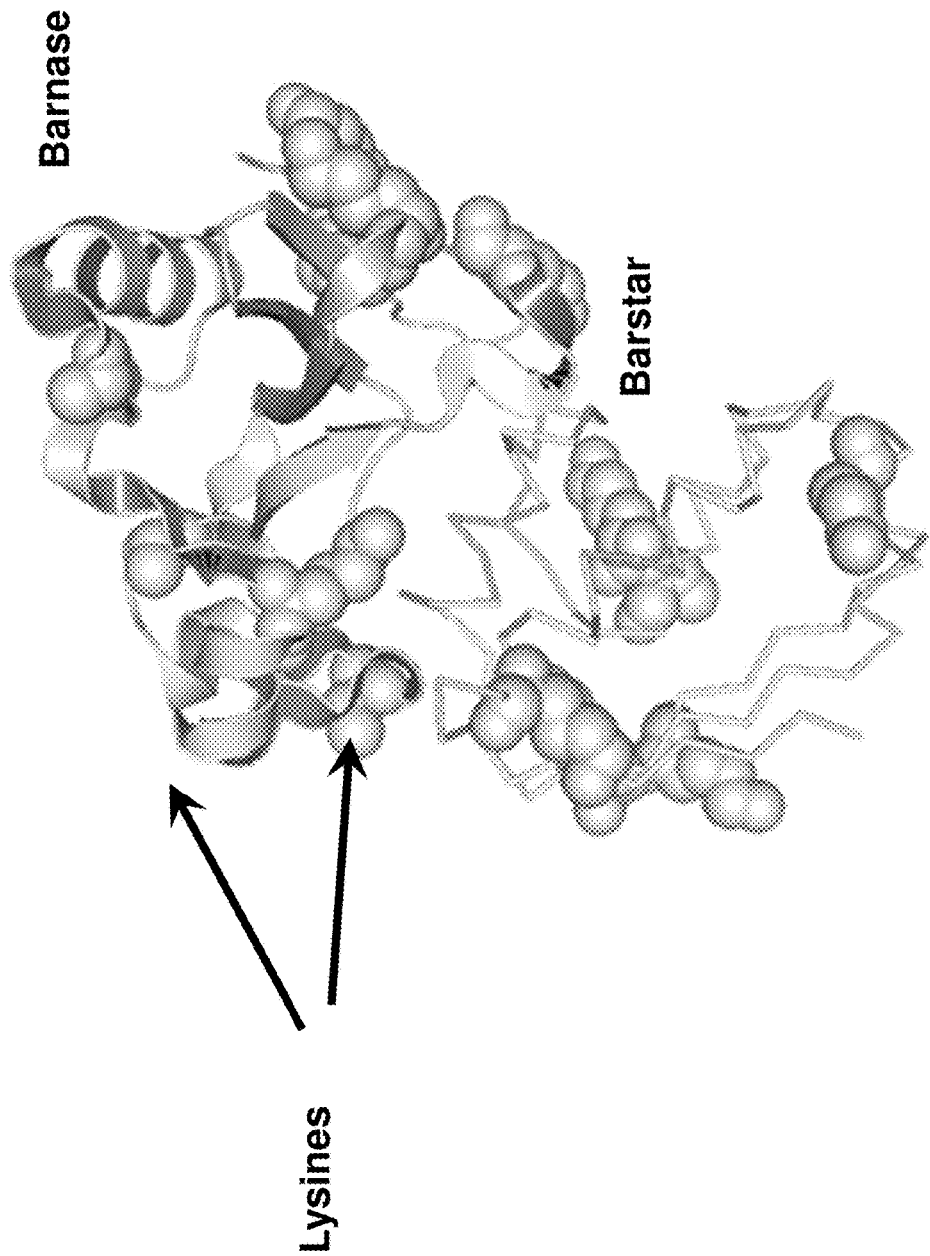
FIG. 8 shows a three dimensional representation of Barnase/Barstar for use as a protein shield.

Barnase/barnstar proteins can also be used as protein shields in the invention. Barnase is a bacterial protein that has about 110 amino acids and has ribonuclease activity. It is synthesized and secreted by the bacterium *Bacillus amyloliquefaciens*, and is lethal to the cell when expressed without its inhibitor barstar. Barstar binds to and occludes the ribonuclease active site, preventing barnase from damaging the cell's RNA after it has been synthesized but before it has been secreted. The barnase/barstar complex has an extraordinarily tight protein-protein binding. Either barnase, barstar, or the barnase/barstar complex can be used as a protein shield. In some embodiments, one or more nucleotides are attached to barnase, and one or more dyes are attached to barstar, then the proteins are combined to form the barnase barnstar with the nucleotides and dye substituents separated such that contact between the dye and the polymerase associated with the nucleotide component does not occur. The opposite approach with one or more dyes on barnase and one or more nucleotides on barstar can also be used. FIG. 8 shows a three dimensional representation of the barnase/barstar complex. Barstar is shown as a ribbon with lysines indicated as spheres.

Figure 9:
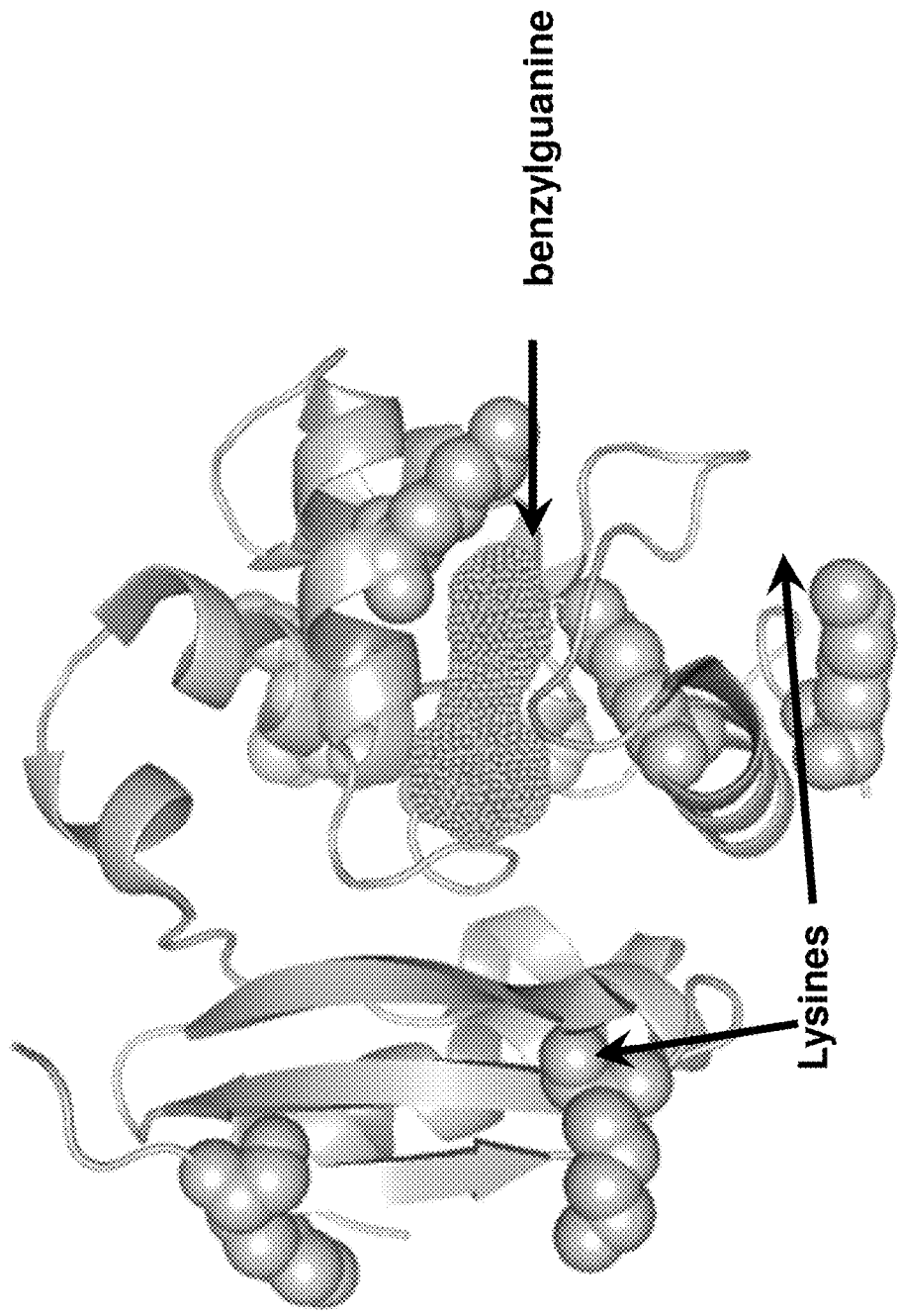
FIG. 9 shows a three dimensional representation of SNAP tag protein for use as a protein shield.

SNAP-tag protein can be used as a shield protein in the invention. SNAP-tag is a 20 kDa mutant of the DNA repair protein O6-alkylguanine-DNA alkyltransferase that reacts specifically and rapidly with benzylguanine (BG) derivatives, leading to irreversible labeling of the SNAP-tag with a synthetic probe. SNAP-tag protein has about 184 residues. In some cases one or more nucleotides are attached to the SNAP tag protein, and one or more dyes are attached to a benzylguanine derivate. In some cases, each of these can be made separately, then combined to form the nucleotide analog having the shielding protein. A similar approach can be take in which the one or more dyes are attached to the SNAP-tag, and the one or more nucleotides are attached to the benzylguanine derivative. FIG. 9 shows a three dimensional version of a SNAP tag protein associated with benzylguanine having lysines shown as spheres. See, for example, RCSB Protein Data Bank code 3KZZ.

Figure 10:
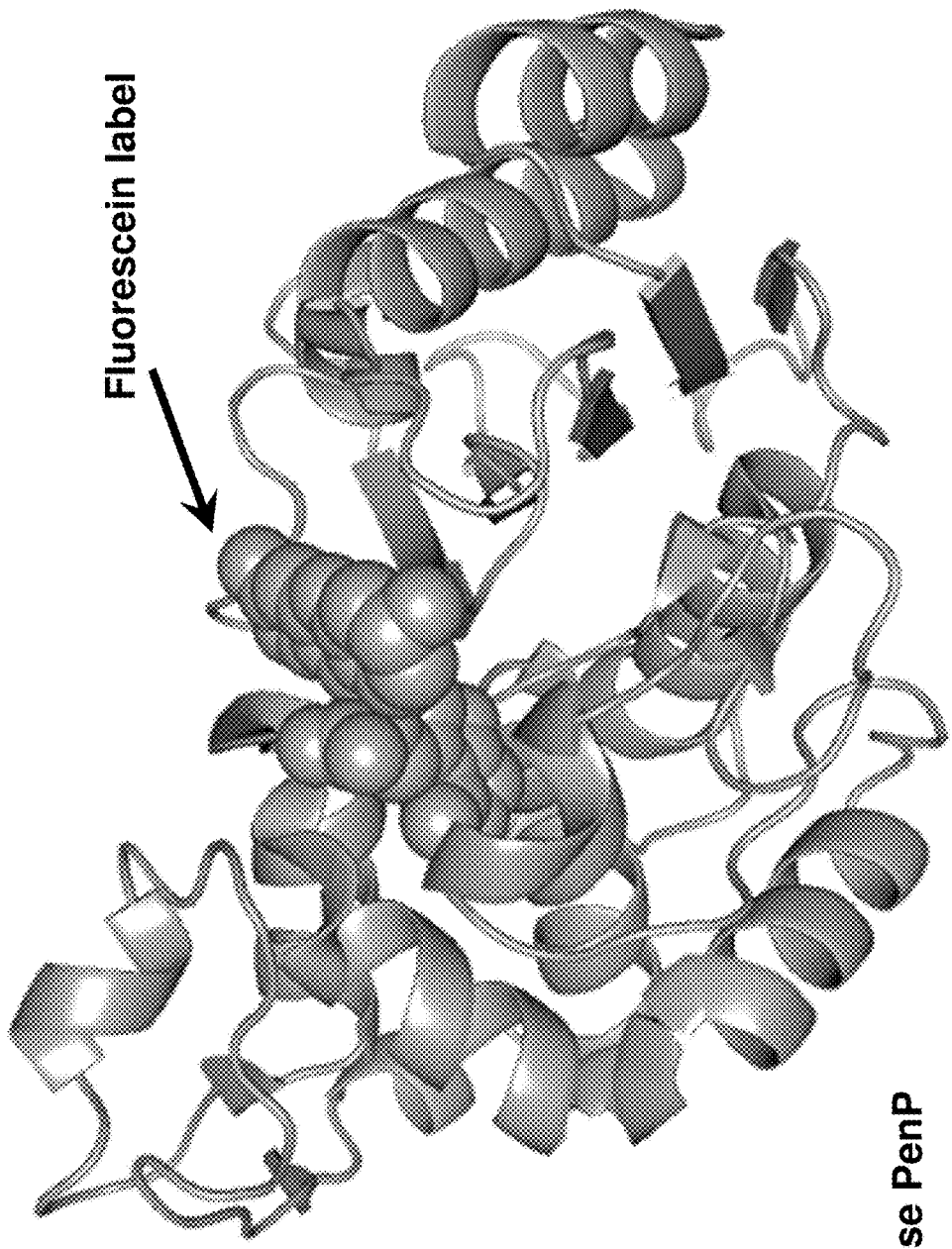
FIG. 10 shows a three dimensional representation of Beta lactamase for use as a protein shield.

Another type of protein that can be a protein shield or component thereof is a beta lactamase. Beta lactamases are enzymes produced by some bacteria that confer resistance to beta-lactam antibiotics. The beta lactamases react by opening up the beta lactam ring in the antibiotic. In some embodiments, a beta lactamase suicide inhibitor is used to connect one or more dye components or one or more nucleotide components to the beta lactamase, where the beta lactamase carries the other component. For example, the beta lactamase inhibitor clavulanic acid attached to one or more dyes can be reacted with a beta lactamase attached to one or more nucleotides. The clavulanic acid forms a covalent bond with the enzyme attaching the nucleotide components. The attachments to the protein are arranged in order to prevent contact between the dyes and a polymerase enzyme associated with one of the nucleotide substituents. FIG. 10 shows a three dimensional representation of a beta lactamase enzyme associated with an inhibitor attached to a fluorescein label. Suitable beta lactamases include cephalosporinases, penicillinases, carbenicillinases, and carbapenamases.

Figure 11:
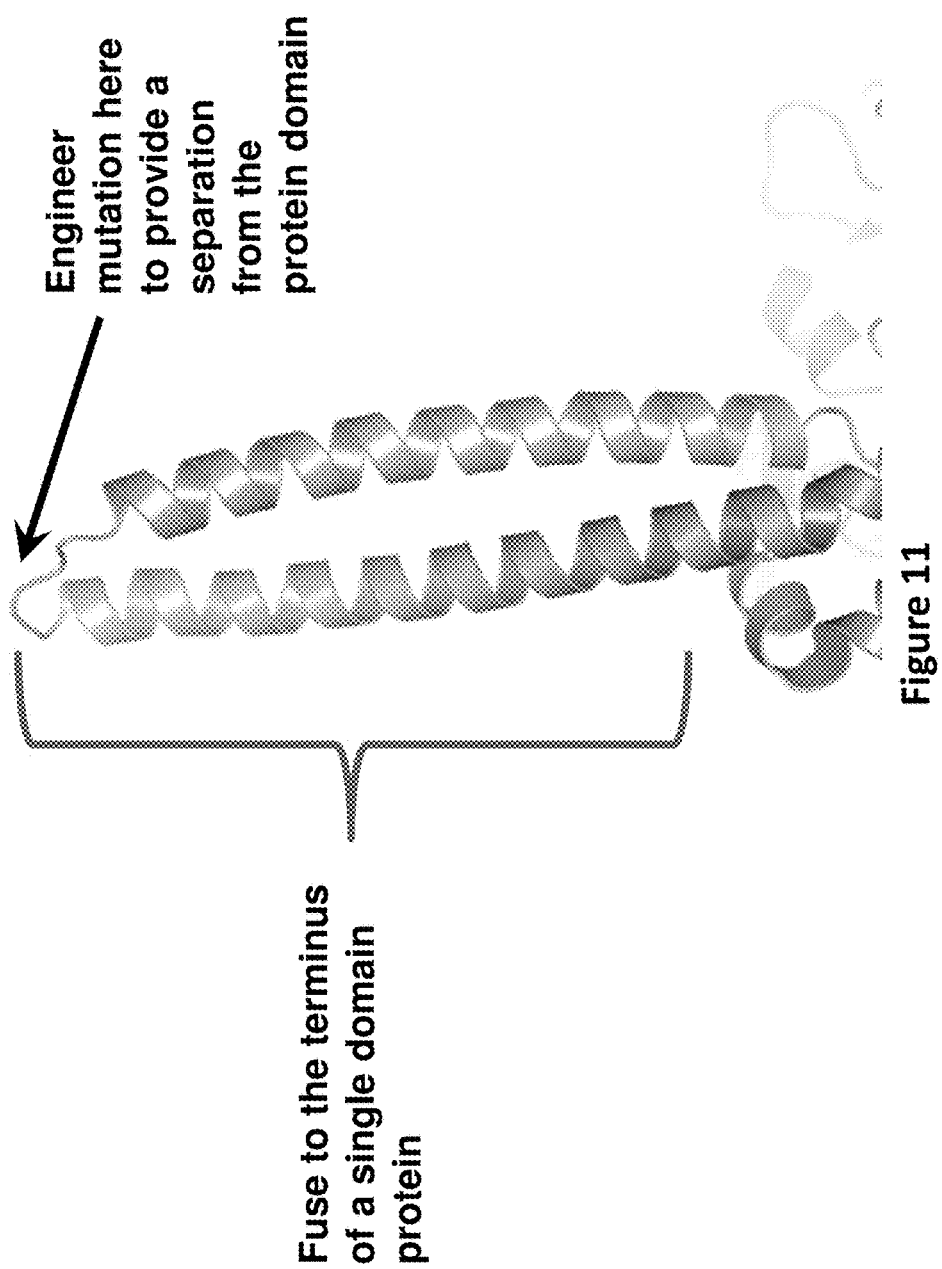
FIG. 11 shows a three dimensional representation of a Coiled-Coil Domain for use as a protein shield.

The coiled-coil domain of a serine tRNA synthetase can be used as a protein shield or component of a protein shield. This domain has a rigid structure that can provide separation between the dye and nucleotide components. FIG. 11 shows a three dimensional representation of a coiled coil domain of a serine tRNA synthetase. The coil structure can be fused to the terminus of a single domain protein. A mutation such as a cysteine can be incorporated into the tip of the coiled coil domain, which can be attached to one or more nucleotides. One or more dyes are attached to more distant portion of the coil coiled domain or to the protein to which the domain is fused. Alternatively, the one or more nucleotides can be attached to the mutation at the tip of the domain, and the one or more dyes can be attached to a more distant portion of the domain or to the protein to which it is fused.

Other suitable shield proteins include proteins engineered to include Leucine Rich Repeats such as Ankyrin repeats, Cyanoverin, and Protein G.

One suitable approach which is embodied in some of the examples provided is the use of tandem domains—protein domains that are associated, one of which has the nucleotide moieties, and one of which has the dye moieties. In some cases, the tandem domains can have an affinity for one another, in some cases the tandem domains can be connected using covalent or binding pair chemistry, in other cases, the tandem domains can be fused and expressed together in cloning. Tandem domains that are connected subsequent to attachment of the nucleotide and dye moieties, e.g. by affinity, covalent or binding pair chemistry are useful because this allows for selective chemistry for attachment of each of the types of moieties. It also allows for a cassette type approach where different nucleotide types can be combined with different dye types in a relatively simple synthetic scheme.

Chemical linking of domains can be carried out in a variety of ways including the chemical methods described herein. One example is to use a TOP7 construct with a unique cysteine thiol. Two batches of such a construct are prepared: one in which the thiol is labeled with a terminal alkyne (using, e.g. a maleimide linked alkyne); the other where it is labeled with an azide. The amines in one batch can then be labeled with bases, and the other with dyes. Subsequently, the specificity of a Click reaction can be exploited to generate covalently linked heterodimers. The linked proteins can be the same or a different protein. As will be clear to one of skill in the art similar schemes can be applied to proteins or protein domains including those described herein including for ubiquitin, or ubiquitin/top7, etc.

One approach is to use a his-tagged protein as one of the elements of the pair, and maltose binding protein as the other element. A nickel column (selective for binding poly-histidine) followed by an amylose column (which would retain maltose binding protein) results in the purification of heterodimers from any contaminating homodimeric fractions.

Pairs of tightly binding proteins that can be used for the production of tandem-protein protein shields are well known in the art. There are many strong protein-protein interactions including many protein-protein inhibitor interactions. Suitable systems include barnase/barstar, colicin immunity proteins, leucine rich repeat containing proteins, ribonuclease inhibitors, or coiled-coil proteins.

The connection of proteins to produce tandem-protein protein shields can be done with small molecules. For example, dihydrofolate reductase (DHFR) binds to the drug methotrexate. Crabtree et al. have demonstrated that a dimeric methotrexate can induce dimerization of DHFR. This approach can be used to generate heterodimers of base and dye labeled DHFR.

The tandem domains can be formed by fusing of the domains with cloning. Suitable fused tandem domains include TOP7-TOP7, TOP7-Ubiquitin, or coiled-coil fused to TOP7 or ubiquitin.

The phrase "substantially identical," in the context of two nucleic acids or polypeptides (e.g., DNAs encoding a polymerase), or the amino acid sequence of a polymerase) refers to two or more sequences or subsequences that have at least about 60%, about 80%, about 90%, about 95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 75%, 80%, 90%, 95%, 97%, 98%, or 99% or more identity, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2012).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra).

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Nucleotide Analogs Comprising Avidin Proteins and Bis-Biotin Linkages

Avidin proteins are useful proteins in nucleotide analogs of the invention. Avidin proteins are biotin-binding proteins, generally having four biotin binding sites. Avidin proteins include, for example, avidin, streptavidin, tamavidin, traptavidin, xenavidin, bradavidin, AVR2, AVR4, and homologs thereof. The biotin binding sites provide attachment points for moieties having one or more nucleotides or one or more fluorescent dyes. Unless otherwise specified, the term avidin protein as used in the application refers to the tetrameric form of the protein. In some cases glycosylation variants are used. We have found that compounds having two biotin sites attached to the tetrameric protein are very useful for producing nucleotide analogs in which the nucleotide portion is kept away from the dye portion such that the dye is prevented from directly interacting with the enzyme.

Figure 14A:
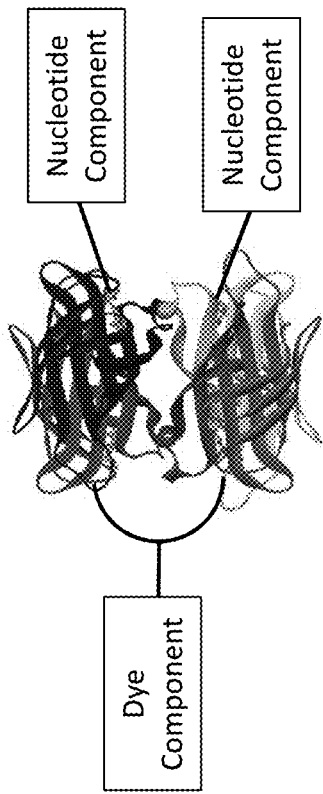
FIGS. 14(A)-14(C) show nucleotide analogs of the invention comprising a bis-biotin moiety in FIG. 14(A) the dye component, FIG. 14(B) the nucleotide component, or FIG. 14(C) both the dye component and nucleotide component.
Figure 14C:
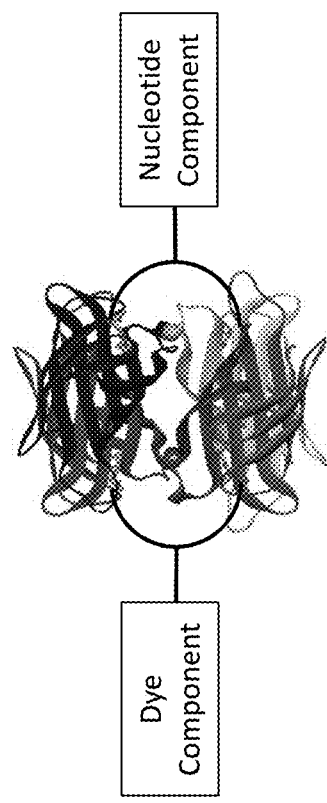
Figure 14B:
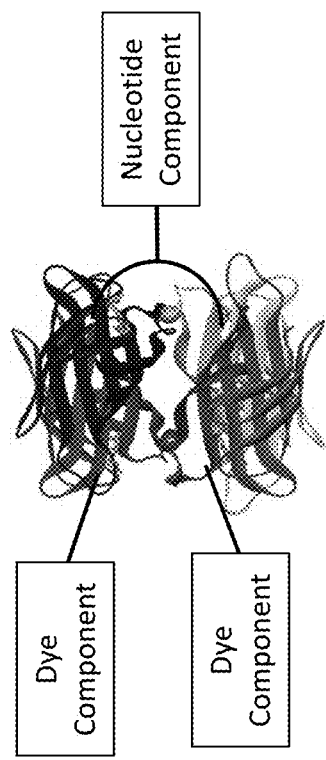

FIG. 14 illustrates the way that bis-biotin compounds can be used to produce protein-shield nucleotide analogs. In FIG. 14(A) a bis-biotin moiety is attached to a dye component. The bis-biotin is attached to two of the four streptavidin biding sites such that the dye component is held onto one side of the avidin protein. In FIG. 14(B) the nucleotide component is attached through the bis-biotin linkage. In FIG. 14(C), both the dye component and the nucleotide component are attached to the streptavidin via a bis-biotin moiety. Although the avidin protein-biotin bond is very strong, we have found that with a single attachment site, there can be some exchange over time. While in many applications, a small amount of exchange is not problematic, we have found that where these connections are used to produce nucleotide analogs for single molecule sequencing, such an exchange can cause a degradation in performance. Where the nucleotide analog is prepared using bis-biotin linkages, we have found that the shelf-life of the nucleotide analogs is significantly improved. The compounds of 14(C) thus provide an improved ability to separate the dye component from the enzyme in order to improve the photostability of the sequencing system, and these compounds also show unexpected improvements in shelf-life.

For the compounds shown in FIGS. 14(A) and 14(B), typically, the compounds are made by first reacting the bis-biotin moiety with the avidin protein. With the appropriate bis-biotin moiety, the reaction of the second biotin is rapid, as the first biotin reaction holds the second biotin in proximity the reaction site on that avidin protein. Once the bis-biotin portion is reacted with the avidin protein, the compound can be readily separated from other reaction components including unreacted avidin protein. This compound can then be reacted with the single biotin component to form the structure shown in FIGS. 14(A) and 14(B). Typically the identity of the single-biotin component (the nucleotide component in 14(A) and the dye component in 14(B) is the same. In some cases, different components can be present in each of the other two binding sites on the avidin protein. This can be accomplished, for example, with a stepwise process including an intermediate purification of the compound in which only one of the two remaining sites have reacted.

In the case of 14(C) the preparation of the compound can proceed by adding either of the bis-biotin moieties to the avidin protein in a first step followed by a second step of adding the nucleotide component. This can be done with or without an intermediate purification step. The finished product 14(C) can be readily purified from other components including unreacted starting materials, e.g. by chromatography.

The dye component can have one or more dye moiety. For example, the nucleotide analog can have from about 1 to about 100 dye moieties, about 1 to 50 dye moieties, about 1 to about 18 dyes moieties, or 1, 2, 3, 4, 5, 6, 7, 8, 9, 10, 11, 12, 13, 14, 15, 16, 17, or 18 dye moieties. In some cases, the nucleotide analog has at least about 1 to about 18 dyes moieties, or at least about 1, 2, 3, 4, 5, 6, 7, 8, 9, 10, 11, 12, 13, 14, 15, 16, 17, or 18 dye moieties. In some cases the dye component includes FRET dyes, for example having one donor and one acceptor, two donors and one acceptor, two donors and two acceptors, etc. The number of dyes can be selected and readily tested for performance. In general, having more than one dye can be used to obtain higher brightness, but as is known in the art, the addition of one more dye does not always increase the brightness commensurate with the number of dyes. Those of skill in the art will understand how to attach the dyes and chose the number of dyes with the best performance for a given system. The type of linkers used to attach the dyes including the length of the linker and its chemical functionality can also be used to engineer the appropriate label performance. Typically the dye moieties are fluorescent dyes. In some cases, the dye moieties comprise fluorescent particles, or other luminescent species.

The nucleotide component can have one or more phospholinked nucleotide. In some cases, the invention may refer to a nucleotide, and in other cases to a nucleoside. Typically a nucleoside has no phosphates where a nucleotide has at least one phosphate linkage. Thus a nucleoside phosphate may be seen as a nucleotide as it has at least one phosphate.

Those of ordinary skill in the art will understand the meanings of the terms as used herein by the context. It is important for many real-time single molecule systems that the nucleotide moiety be phospholinked. In this way, the cleavage of the alpha-beta phosphodiester bond in the nucleotide analog releases the labeled component. For example, the nucleotide analog can have from about 1 to about 100 phospholinked nucleotide moieties, about 1 to 50 phospholinked nucleotide moieties, about 1 to about 18 phospholinked nucleotide moieties, or 1, 2, 3, 4, 5, 6, 7, 8, 9, 10, 11, 12, 13, 14, 15, 16, 17, or 18 phospholinked nucleotide moieties. In some cases, the nucleotide analog has at least about 1 to about 18 phospholinked nucleotide moieties, or at least about 1, 2, 3, 4, 5, 6, 7, 8, 9, 10, 11, 12, 13, 14, 15, 16, 17, or 18 phospholinked nucleotide moieties. Raising the number of phospholinked nucleotide moieties tends to raise the effective concentration of the nucleotide at the enzyme. As is well known in the art, the concentration of nucleotide can be varied in order to control the polymerase kinetics, and that depending on the system and the desired performance, the concentration of the nucleotide can be varied both by controlling the amount of nucleotide analog per volume and by controlling the number of phospholinked nucleotides per nucleotide analog. Those of skill in the art will understand how to use the compounds of the invention to optimize system performance. The lists of potential choices described herein for the numbers and types of phospholinked moieties can be combined with any of the described numbers and types of dye moieties described.

Figure 15:
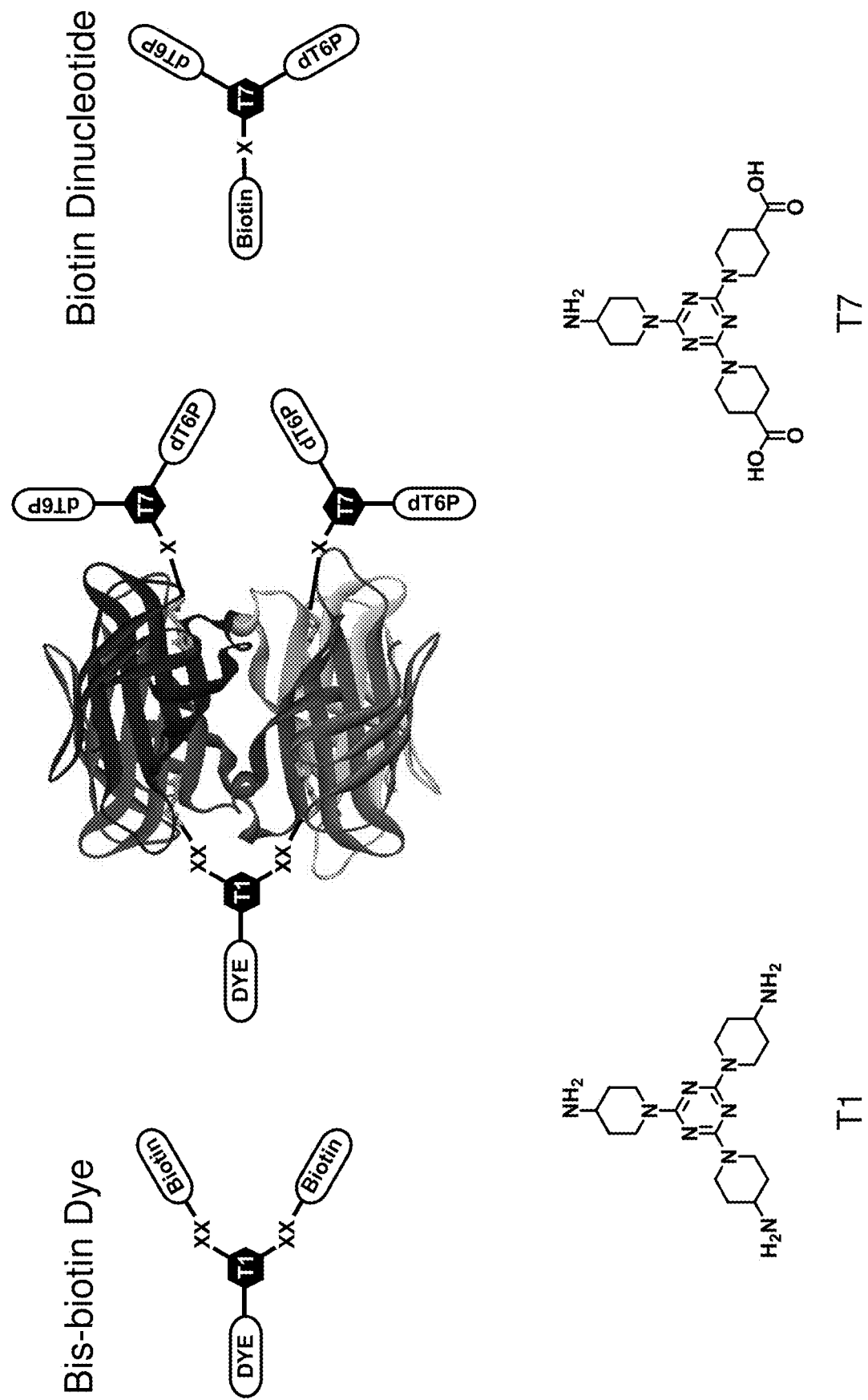
FIG. 15 shows a protein shield nucleotide analog of the invention having an avidin protein connected to a bis-biotin dye component and to two biotin dinucleotide components. Also shown in FIG. 15 are the bis-biotin dye component and biotin dinucleotide component.

FIG. 15 shows an exemplary compound of the type shown in 14(A) in which a dye moiety is attached to an avidin protein, such as streptavidin, through a bis-biotin moiety, and nucleotide moieties are attached to the avidin protein through single biotin binding moieties. The figure shows a representative bis-biotin dye having a central tri-functional linker T1 connecting one dye moiety to two biotins. The trifunctional linker is connected to the biotin moieties through spacers or linkers designated by an X. A typical spacer or linker could have, for example three to six methylene units (CH$_2$) connected through amide linkages. The bis-biotin with the dye component is attached to two of the streptavidin binding sites. The other two streptavidin binding sites are attached, each to a single biotin of a biotin dinucleotide that is made up of a trifunctional linker T7 attached to the biotin through a linker or spacer, and to two phospholinked nucleotides. Here, the phospholinked nucleotides are dT6P, a deoxy T nucleoside connected to the linker through a hexaphosphate. We have found that relatively rigid, aromatic trifunctional linkers such as T1 and T7 can be useful in the construction of the nucleotide analogs of the invention. The figure shows a representative structure to illustrate how such a nucleotide analog of the invention is made.

Figures 16A, 16B:
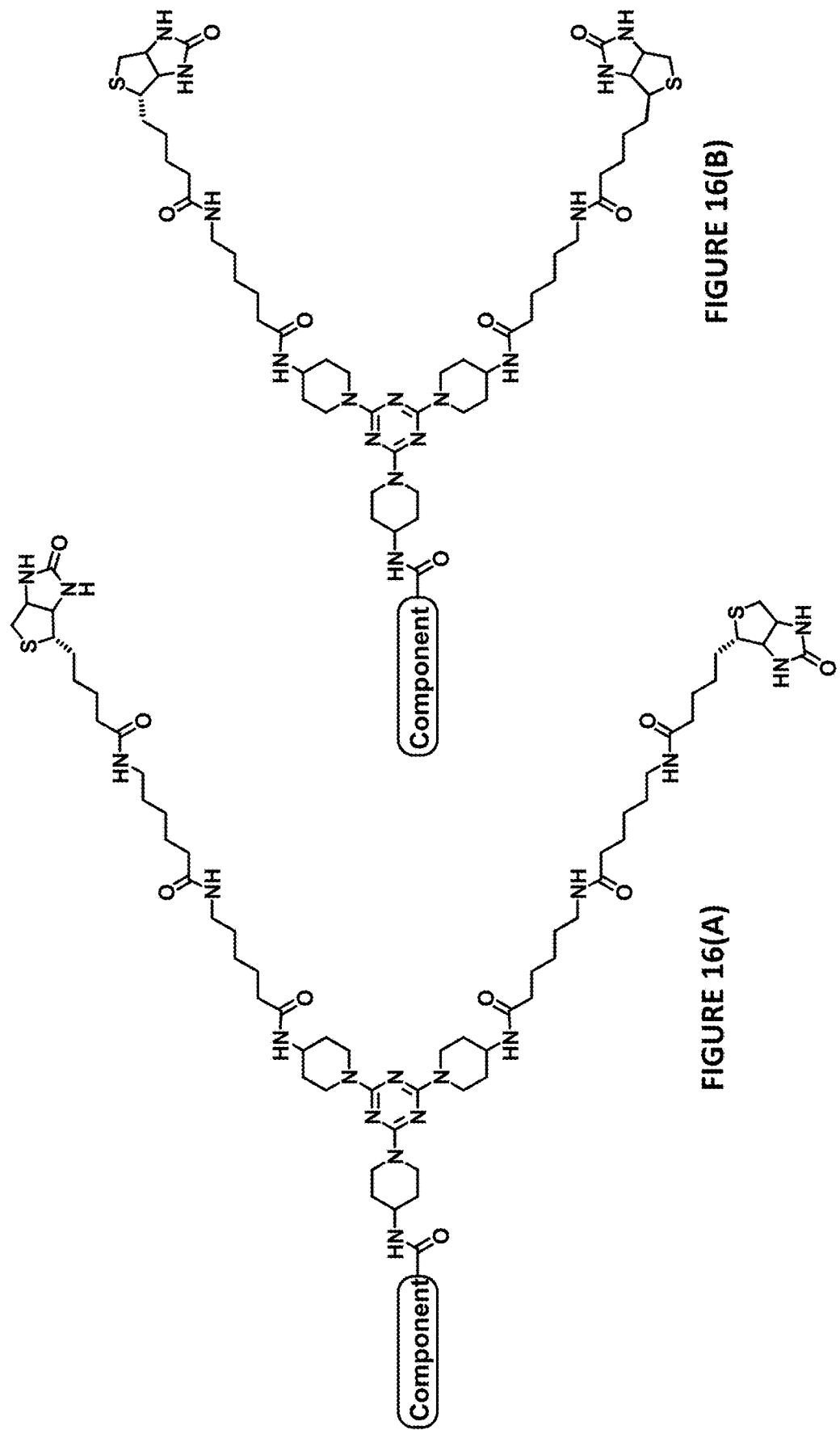
FIG. 16(A) and FIG. 16(B) each show exemplary bis-biotin moieties.

FIG. 16 shows two representative bis-biotin linkers that can be used in the instant invention. We have found that the length of both of these bis-biotin linkers is useful for the invention. The linker shown in FIG. 16(A) has 40 bonds between the biotin linkages. The linker shown in FIG. 16(B) has 26 bonds between the biotin linkages. As will be understood, if the linkage between the biotins is too short, then the two biotins will not readily connect to two binding sites on the same avidin tetrameric protein. Also, if the linkage between the biotins is too long, then the second biotin may be slower to contact and bind to the second binding site on the avidin protein. In some cases, a bis-biotin linker having between about 15 and about 50 bonds between biotin linkages is useful. The bis-biotin linkers of FIG. 16 are shown as linked to a component. This component can be either dye component or a nucleotide component, and as consistent with the application, the dye component can have one or multiple dye moieties, and the nucleotide component can have one or multiple phospholinked nucleotide moieties.

Figure 17:
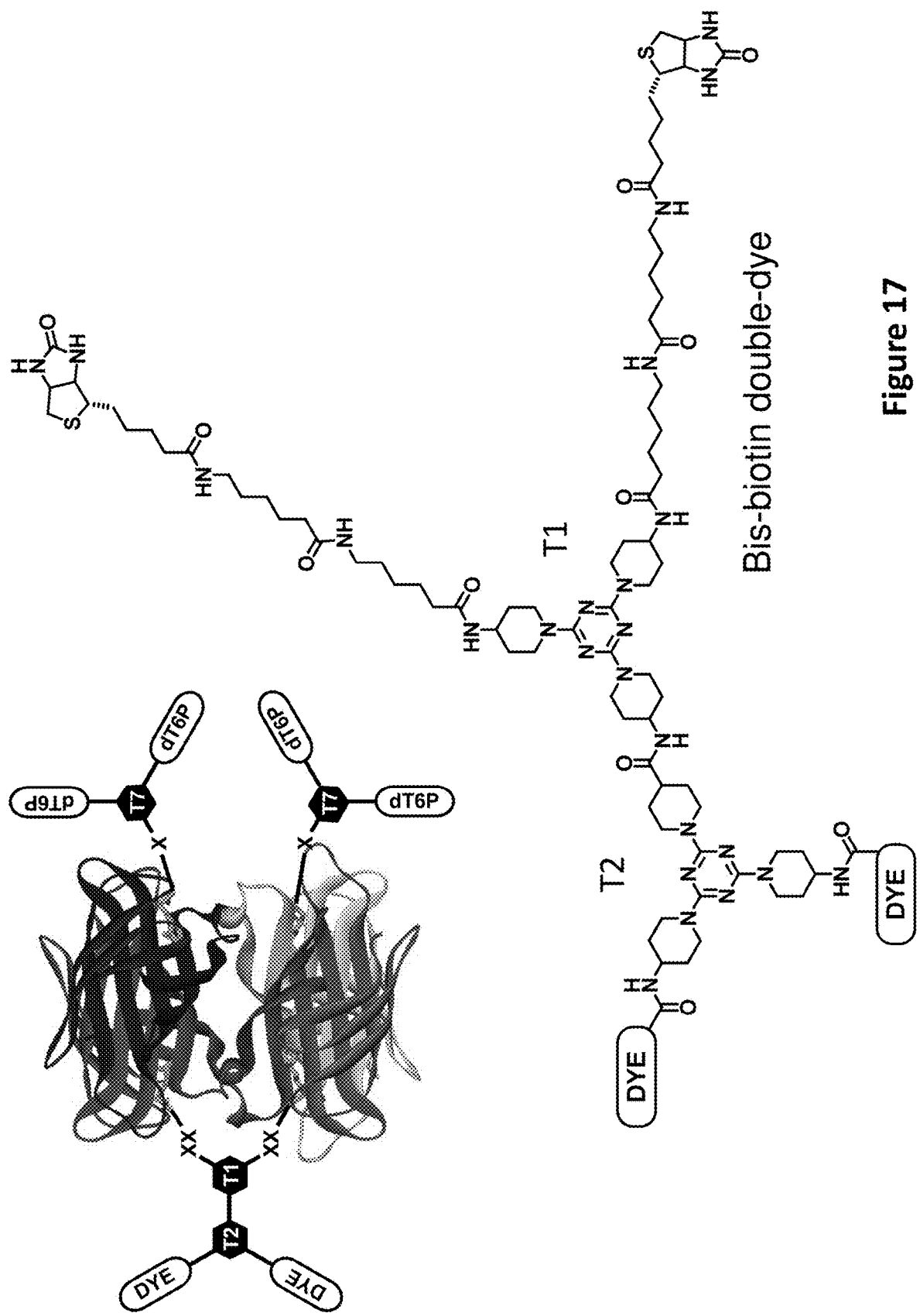
FIG. 17 shows a protein shield nucleotide analog of the invention with an avidin attached to a bis-biotin dye component having two dyes. Also shown is an exemplary bis-biotin double-dye component.

FIG. 17 shows a nucleotide analog of the invention having two dye moieties attached to an avidin protein shield through a bis-biotin moiety, and having four phospholinked nucleotide moieties. FIG. 17 shows the structure of a bis-biotin double dye compound that can be used to produce such a nucleotide analog. Here, the bis-biotin double-dye analog is produced using two trifunctional linkers T2 and T1. Each of the two biotins is attached to the trifunctional linker through two amino hexanamide spacers X through amide linkages. This structure illustrates one approach that can be expanded to incorporate even more dye moieties or phospholinked nucleotide moieties. In the nucleotide analog of FIG. 17, the two dyes can be dyes of the same type, or can be of two different types. The two dyes can comprise a FRET donor and a FRET acceptor. FRET pairs can be used, for example in order to produce labels that are bright, and that have a relatively high Stokes shift, where the Stokes shift is the difference in wavelength between the absorption maximum and emission maximum for the label. Here, two phospholinked nucleotides are connected to a trifunctional linker, T7, which is connected through a linker or spacer X to a single biotin. As described above the preparation of the nucleotide analog typically involves a first reaction between the avidin protein such as streptavidin and the bis-biotin double dye, followed by treatment with the compound with a single biotin moiety and two phospholinked nucleotides.

Figure 18:
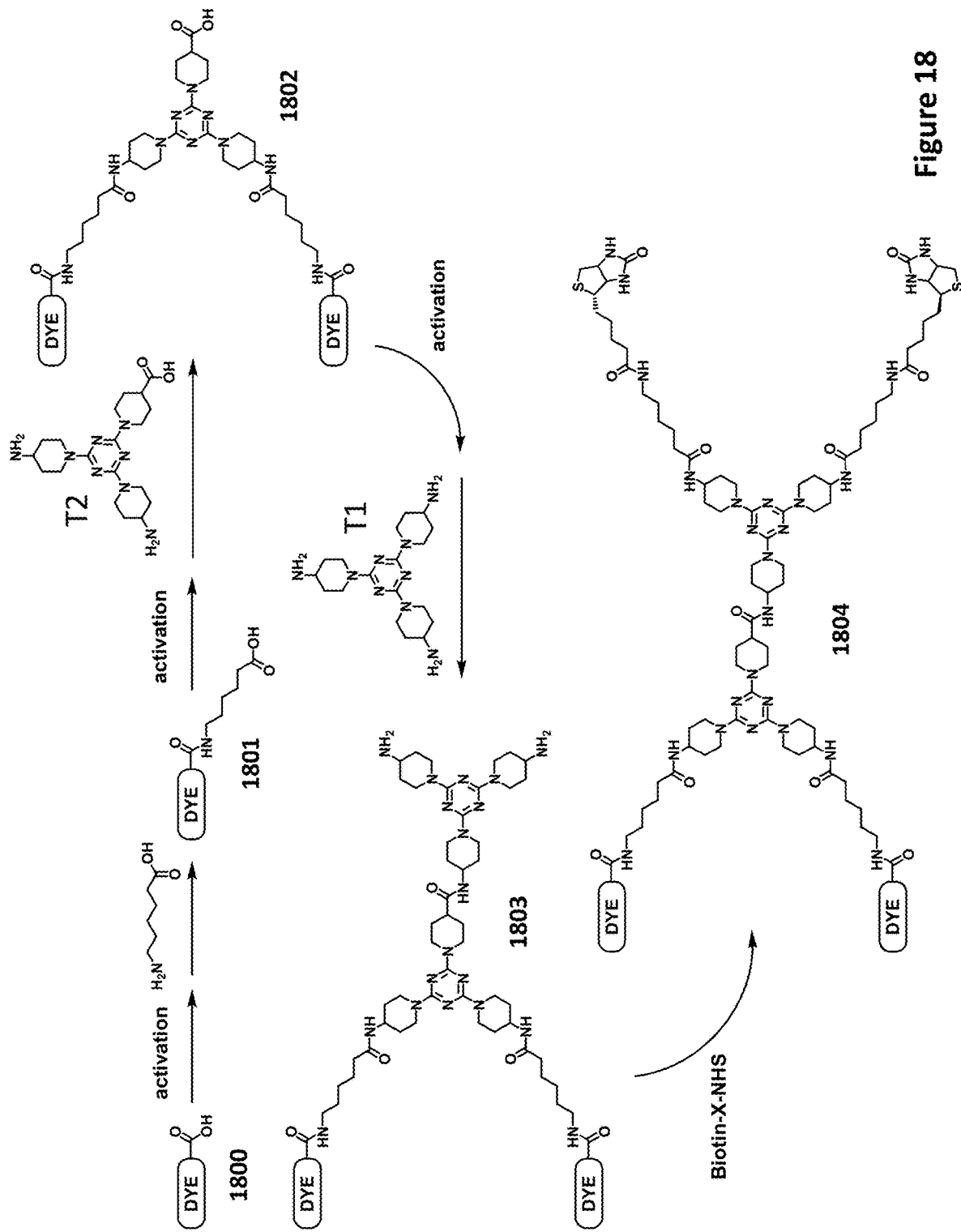
FIG. 18 shows an exemplary synthesis of a bis-biotin double-dye.

FIG. 18 provides an example of a how a bis-biotin double dye compound can be formed using standard organic chemistry methods. The dye moiety for the present synthesis 1800 has a single activatable carboxylic acid which is coupled to the amine group of 6-amino-hexanoic acid. This acid group on the compound formed, 1801, is activated and reacted with trifunctional linker T2 to form a double dye species 1802. The carboxylic acid on 1802 is activated and reacted with trifunctional linker T1 to form compound 1803. Compound 1803 is reacted with the N-hydroxy succinimide ester biotin-X-NHS where X is a 6-amino-hexanamide. This condensation forms the bis-biotin double dye compound 1804.

Figure 19:
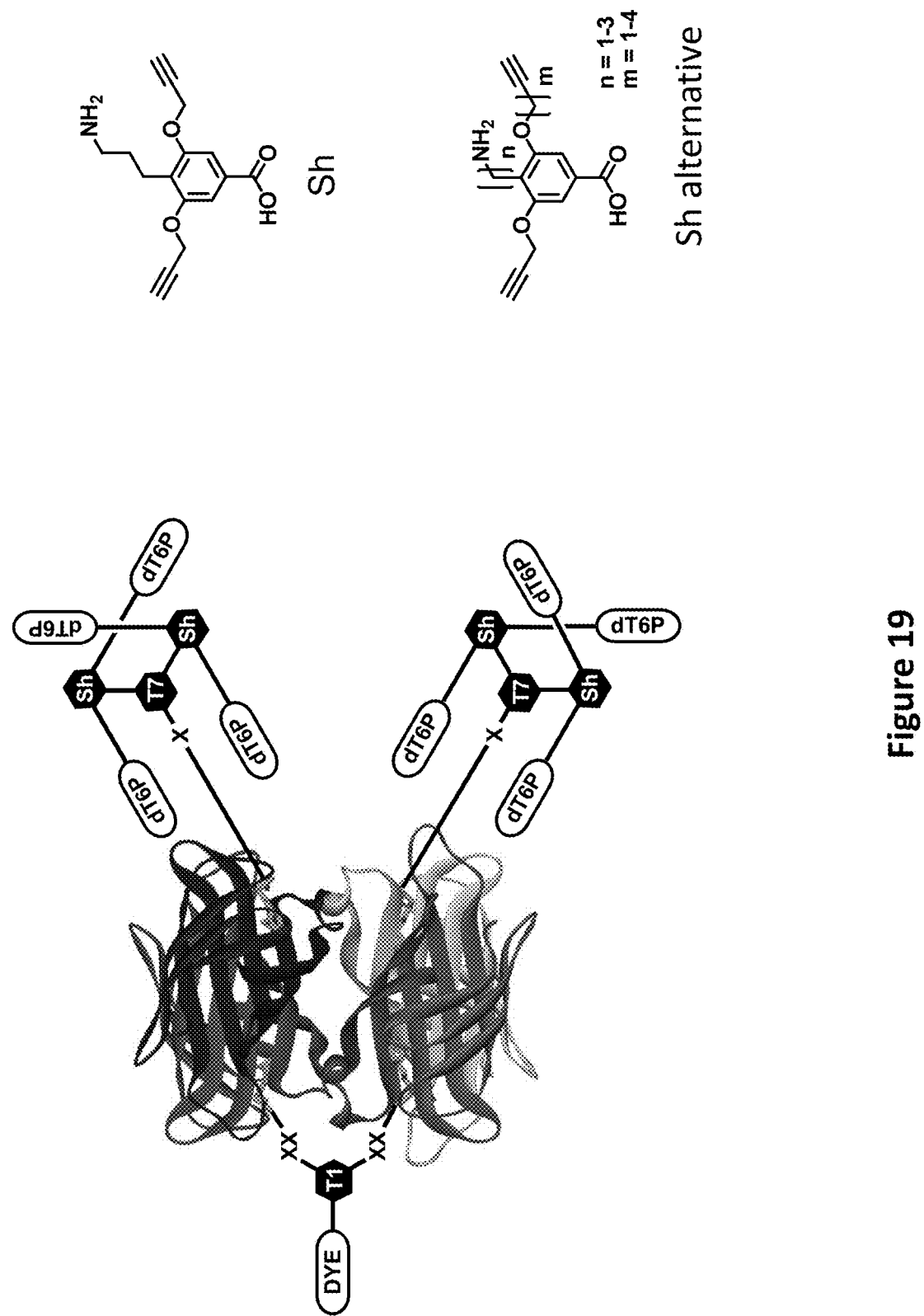
FIG. 19 shows a protein shield nucleotide analog of the invention having two nucleotide components and eight phospholinked nucleotides. Also shown is the trifunctional linker Sh and an Sh alternative.

FIG. 19 shows a nucleotide analog of the invention having 8 phospholinked nucleotides. For this compound, there is a bis-biotin moiety attached to a single dye moiety that is attached to two of the four avidin protein, e.g. streptavidin, biotin binding sites. The phospholinked nucleotides are connected through a compound having one biotin and three trifunctional linkers (e.g. one T7 trifunctional linker and two Sh trifunctional linkers). The phospholinked nucleotide moieties can each be, for example a hexaphosphate connected to nucleoside dT (dT-6-P). FIG. 19 also shows the structure of Sh, a trifunctional linker that can be used to produce the nucleotide analog shown. For the compound of interest, the amine group and two acetylene groups of the Sh are used to link the Sh, and the carboxylic acid group is left unreacted. As discussed in other parts of the application, in some case, having a charged groups on the nucleotide analog such as carboxylate and sulfate groups can assist in assuring the aqueous solubility of the nucleotide analogs. The trifunctional linker Sh is only one possible trifunctional linker that can be used in the instant application. In some cases it is desirable to control the length of the set of bonds connecting the linking groups. FIG. 19 also shows an Sh alternative where the lengths of these sets of bonds can be varied to improve performance of the nucleotide analog.

Figure 20:
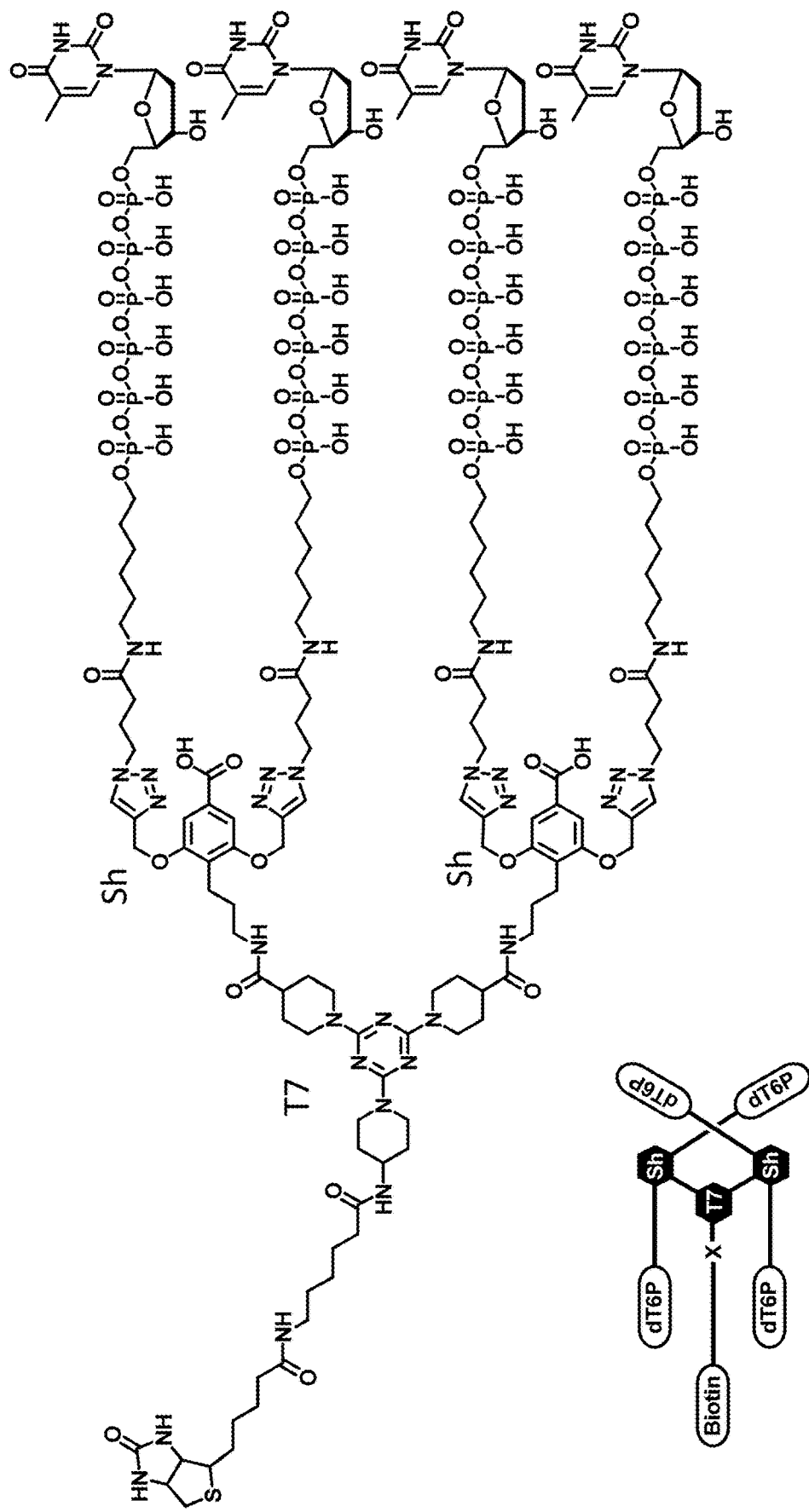
FIG. 20 shows an exemplary nucleotide component having four phospholinked nucleotides attached to one biotin.

FIG. 20 shows an example of a compound having a single biotin and four phospholinked nucleotides that can be used to produce nucleotide analogs of the invention. Here the biotin is attached to a T7 trifunctional linker through an amino hexanoic acid spacer. The trifunctional liner T7 is connected to two Sh trifunctional linkers, and each of the Sh trifunctional linkers is attached to two phospholinked nucleotide moieties through a linker. The phospholinked nucleotide moieties are attached to the Sh through triazole linkages that can be formed, for example using Click chemistry.

Figure 21:
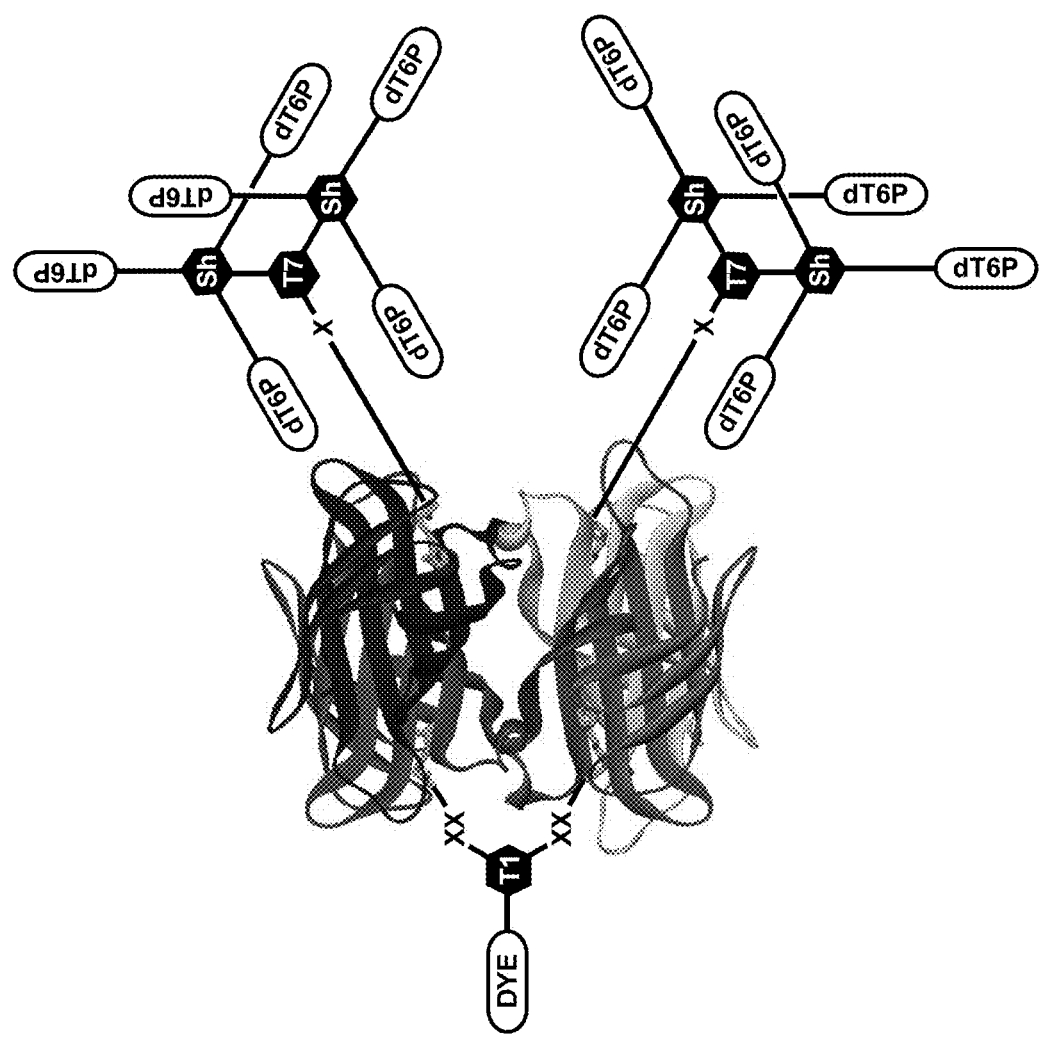
FIG. 21 shows a protein shield nucleotide analog of the invention having two nucleotide components and 12 phospholinked nucleotides.

FIG. 21 shows a nucleotide analog of the invention of the invention having 12 phospholinked nucleotide moieties. For this compound, there is a bis-biotin moiety attached to a single dye moiety that is attached to two of the four avidin protein, e.g. streptavidin, biotin binding sites. In some cases, this bis-biotin portion can have multiple dye moieties as described herein. The phospholinked nucleotides are connected through a compound having one biotin, one trifunctional linker T7 and two tetra-functional linkers (e.g. Sh tetra-functional linkers). The Sh linker in this example differs from the Sh linker referred to above and shown in FIG. 19 and FIG. 20 in that it has an additional linkage through the carboxylic acid shown in the Sh structure on FIG. 19. The phospholinked nucleotide moieties can each be, for example a hexaphosphate connected to nucleoside dT (dT-6-P).

Figure 22:
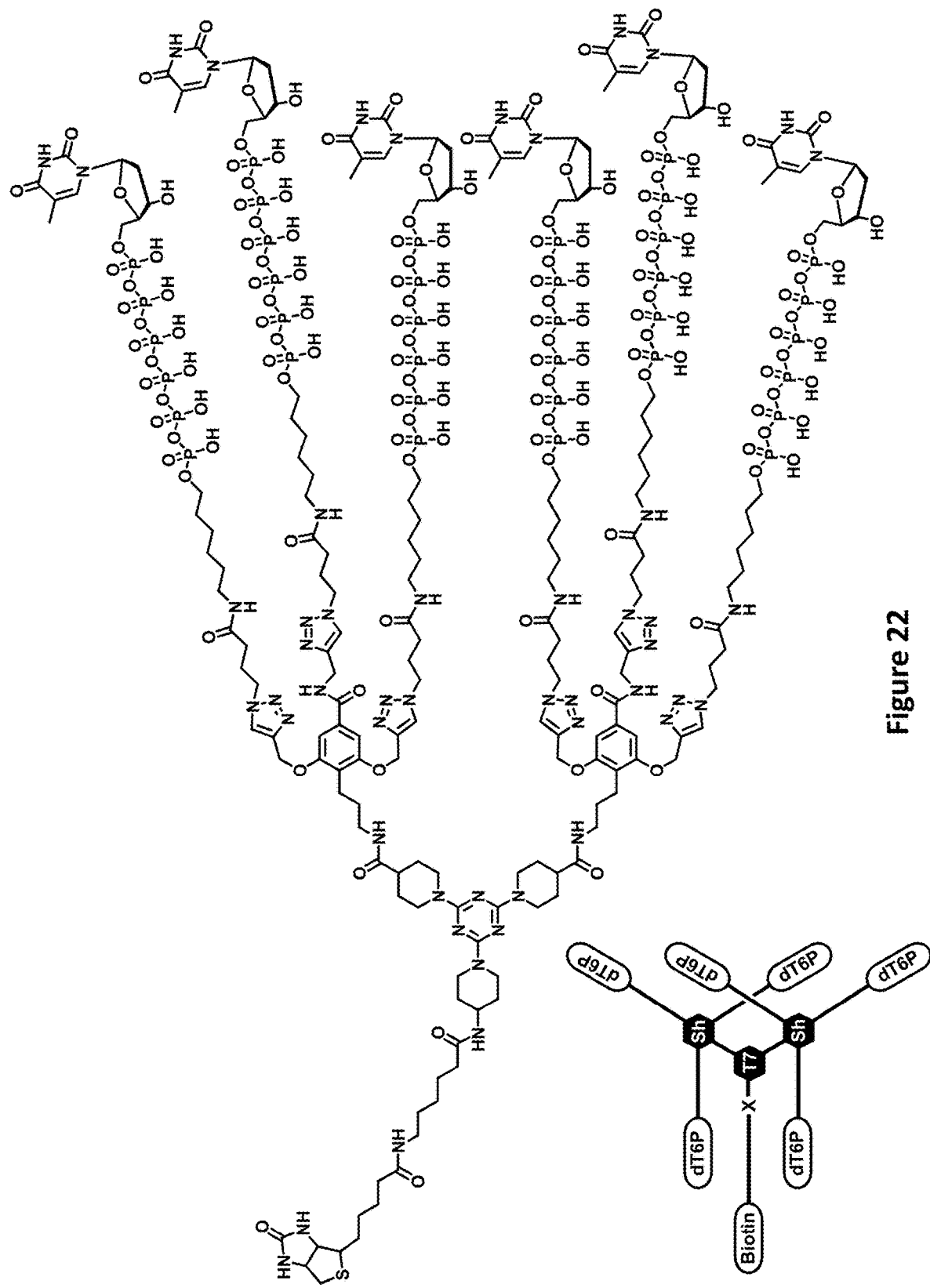
FIG. 22 shows an exemplary nucleotide component with one biotin and six phospholinked nucleotides.

FIG. 22 shows an example of a compound having a single biotin and six phospholinked nucleotides that can be used to produce nucleotide analogs of the invention. Here the biotin is attached to a T7 trifunctional linker through an amino hexanoic acid spacer. The trifunctional liner T7 is connected to two Sh tetra-functional linkers, and each of the Sh tetrafunctional linkers is attached to three phospholinked nucleotide moieties through a spacer. The phospholinked nucleotide moieties are attached to the Sh through triazole linkages that can be formed, for example using Click chemistry.

Figure 23:
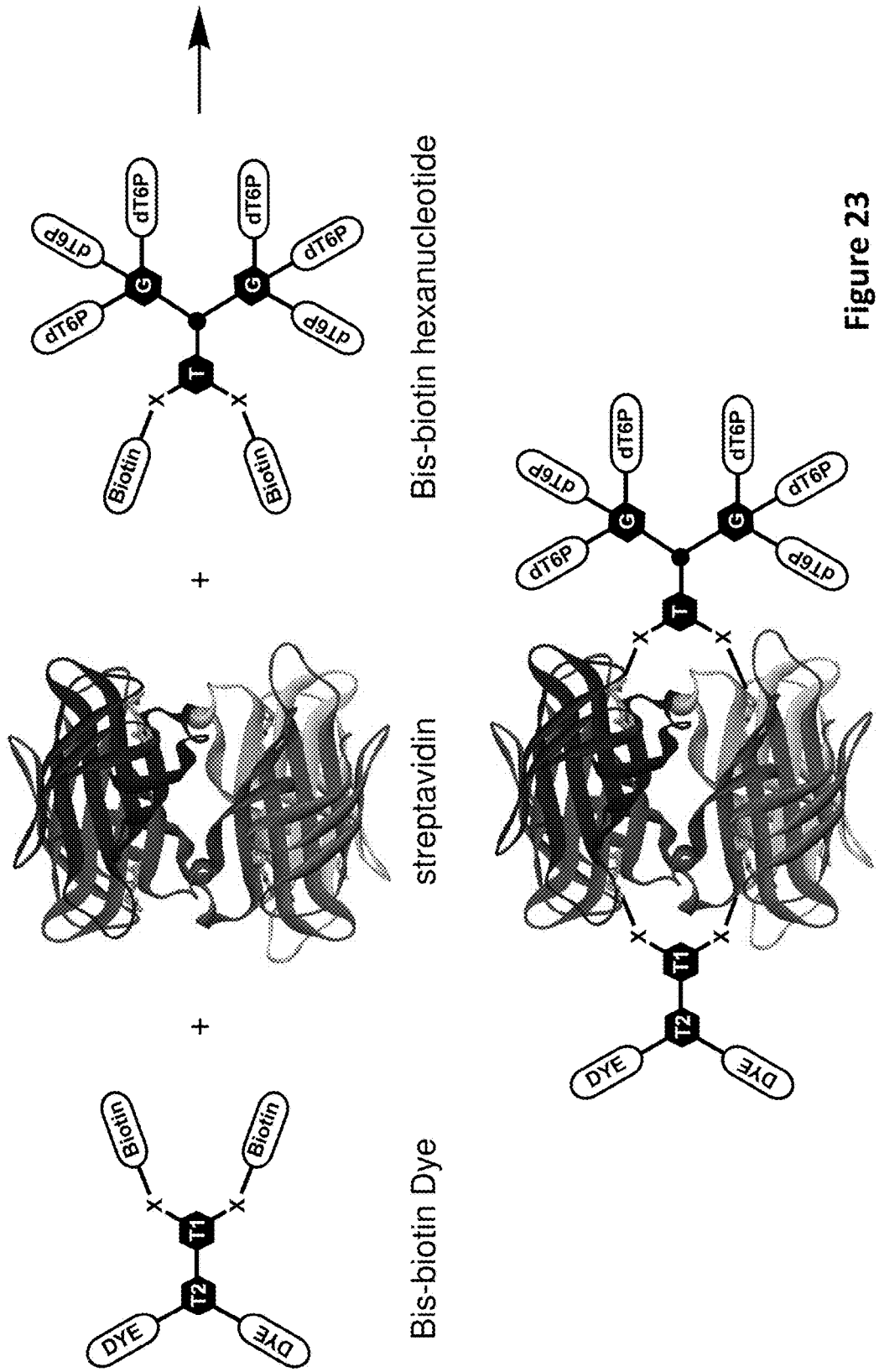
FIG. 23 shows an exemplary protein shield nucleotide analog of the invention having a bis-biotin dye component with two dyes and a bis-biotin component having six phospholinked nucleotides. The figure also shows how this protein shield nucleotide analog can be made using streptavidin, a bis-biotin dye component, and a bis-biotin hexanucleotide component.

FIG. 23 shows a structure for a nucleotide analog of the invention in which both the phospholinked nucleotide moieties and the dye moieties are attached to the avidin protein through bis-biotin moieties. Here, two dye moieties are attached to a bis-biotin moiety through a trifunctional linker T2. The biotin moieties are connected through a spacer X and a trifunctional moiety T1. There are 6 phospholinked nucleotide moieties attached to the bis-biotin moiety in two groups of three phospholinked nucleotides each attached through a tetrafunctional linker G to a trifunctional linker. FIG. 23 illustrates that the nucleotide analog of the invention can be prepared by reacting an avidin protein such as a streptavidin with a bis-biotin dye component and a bis-biotin hexanucleotide component. These reactions are typically carried out in series, optionally with a purification step between the reactions. This figure shows an analog with two dye moieties and six phospholinked nucleotide moieties, but it will be clear to those of ordinary skill in the art that the methods provided allow for the preparation of nucleotide analogs with a wide variety of numbers and types of substituents.

Figure 24:
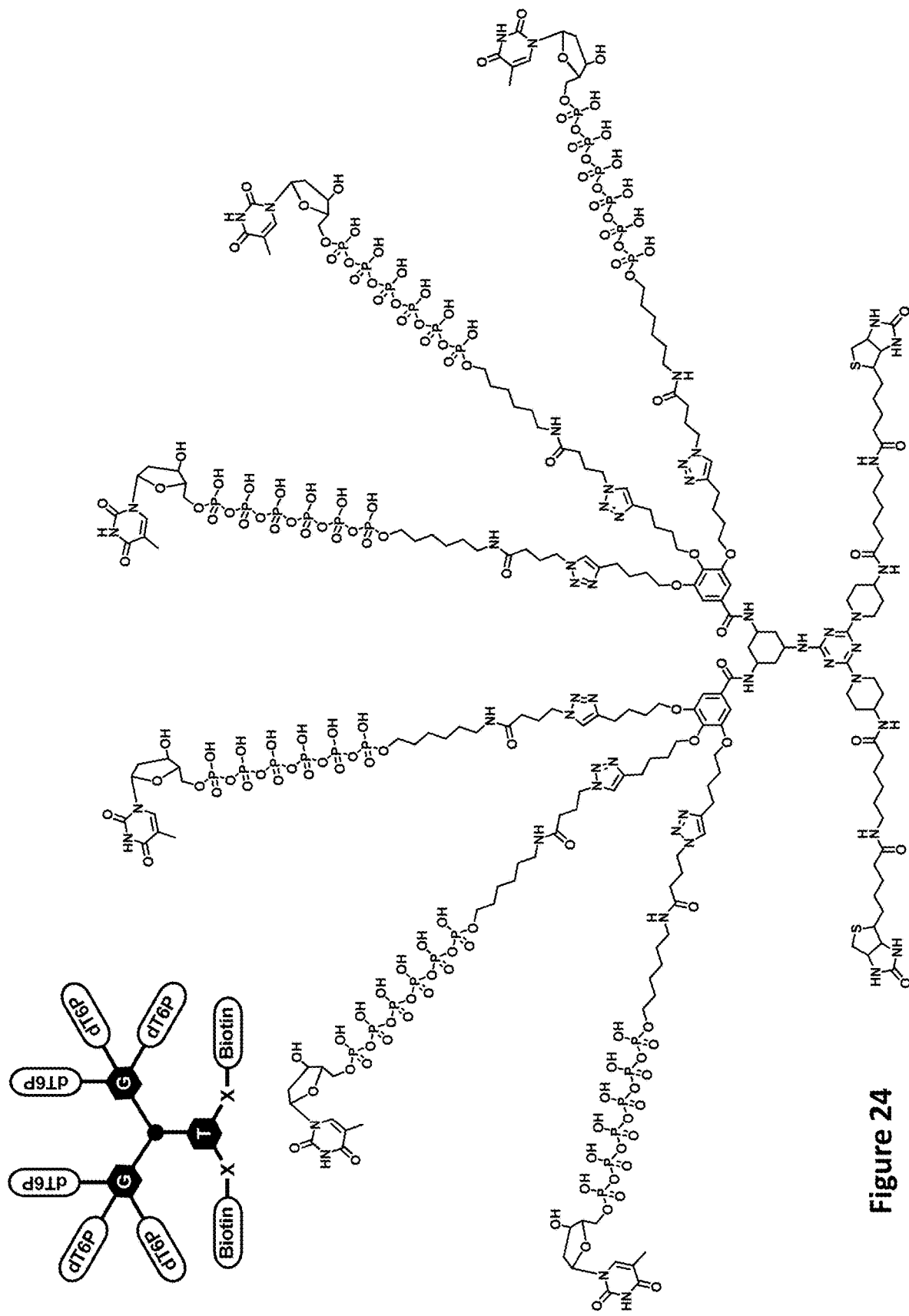
FIG. 24 shows an exemplary bis-biotin hexanucleotide component.

FIG. 24 shows an example of a bis-biotin hexanucleotide compound for preparing a nucleotide analog of the invention. This nucleotide analog has two biotins, each connected through an amino hexanamide spacer to a trifunctional linker T. The trifunctional linker T is connected to a 1, 3, 5-triamino cyclohexane linker, which is in turn connected to two tetrafunctional G linkers which are each connected to three phospholinked nucleotide moieties. The phospholinked nucleotide moieties are attached to the tetrafunctional linkers G through triazole linkages that can be formed, for example using Click chemistry.

Figure 25:
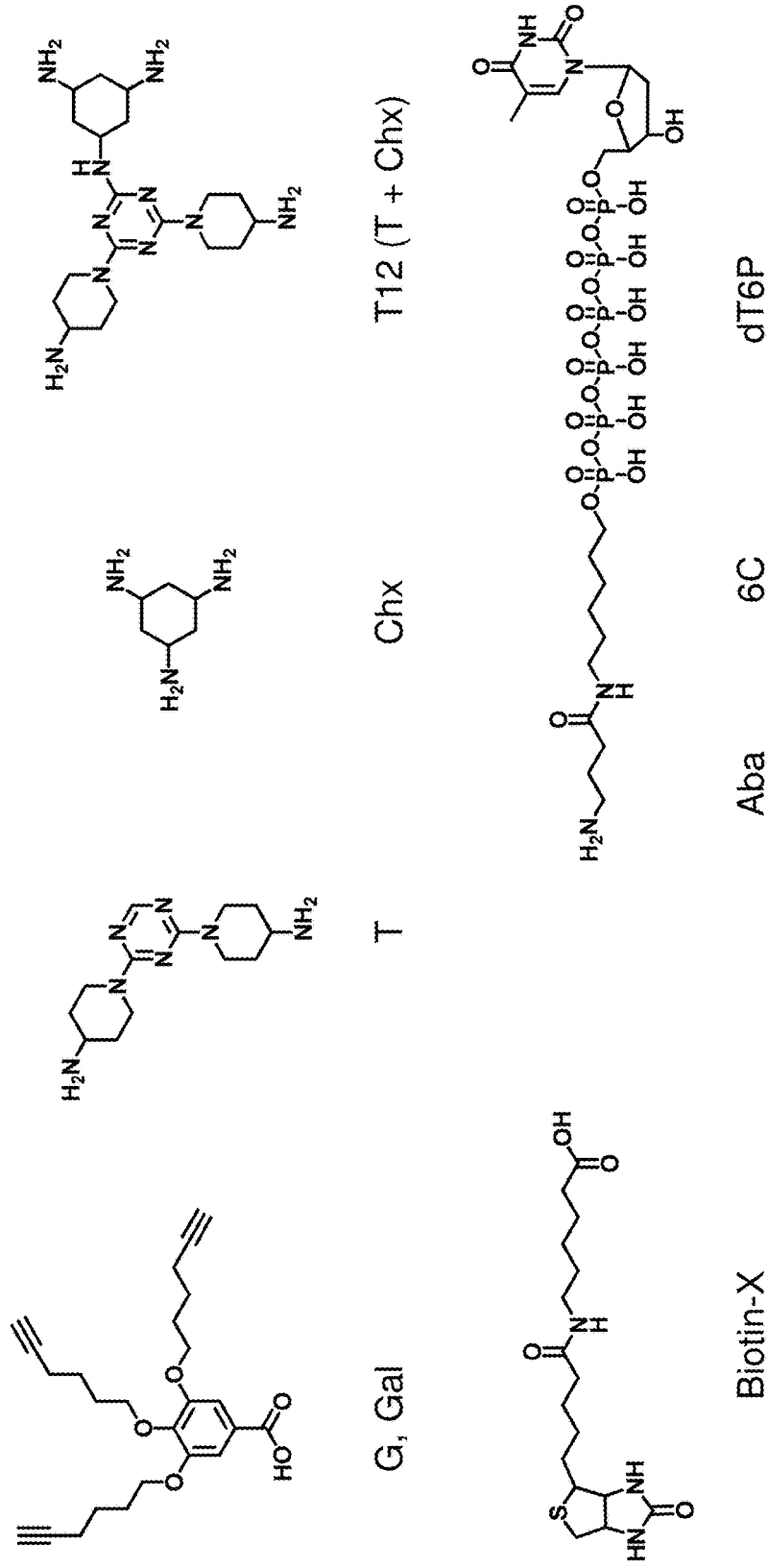
FIG. 25 shows components G (Gal), T, Chx, T12, Biotin-X, Aba, 6C, and dT6P that can be used to prepare a bis-biotin hexanucleotide component.

FIG. 25 shows components that are used in the preparation of the bis-biotin hexanucleotide shown in FIG. 24 using standard organic chemical techniques.

Figure 26:
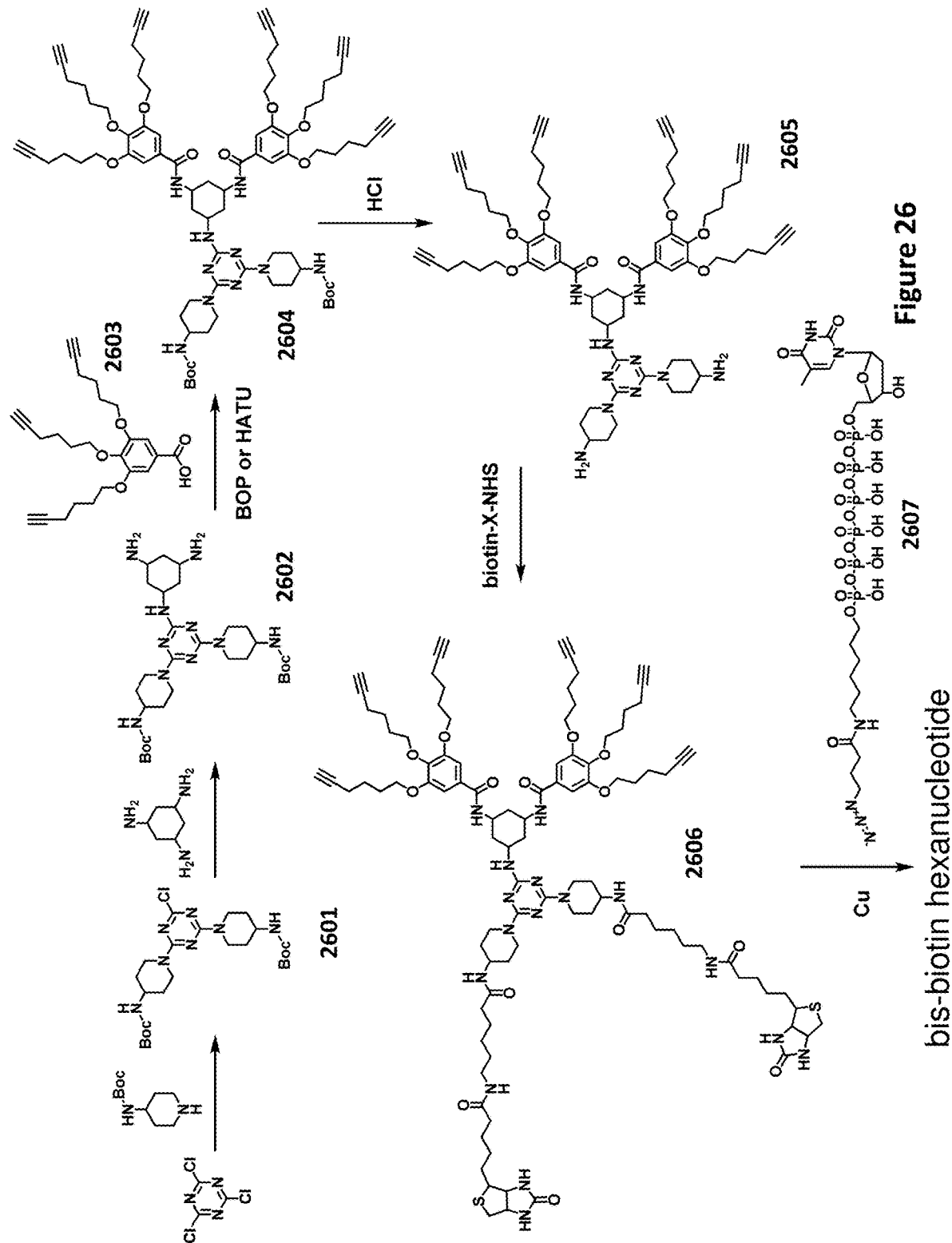
FIG. 26 shows an exemplary synthesis of a bis-biotin hexanucleotide component.

FIG. 26 shows a representative synthesis of a bis-biotin hexanucleotide for preparing a nucleotide analog of the invention. Two equivalents of Boc-protected 4-aminopiperidine is added to 2, 4, 6-trichloro-1,3,5-triazine to form intermediate 2601, to which is added 1,3,5-triaminocyclohexane to form intermediate 2602. To intermediate 2602 is added two equivalents of the substituted gallic acid 2603 form amide bonds using either Benzotriazole-1-yl-oxy-tris-(dimethylamino)-phosphonium hexafluorophosphate (BOP) or O-(7-azabenzotriazole-1-yl)-N,N,N,N'-tetramethyluronium hexafluorophosphate (HATU), producing intermediate 2604. Removal of the Boc protecting groups with acid yields intermediate 2605 which is reacted with two equivalents of biotin-X-NHS (the N-hydroxysuccinimide ester of biotin-X shown in FIG. 25) to yield intermediate 2606. Click chemistry (Copper catalysed Huisgen addition) is then used to attach six equivalents of phospholinked nucleotide intermediate 2607 to form the bis-biotin hexanucleotide shown in FIG. 24.

Figure 27A:
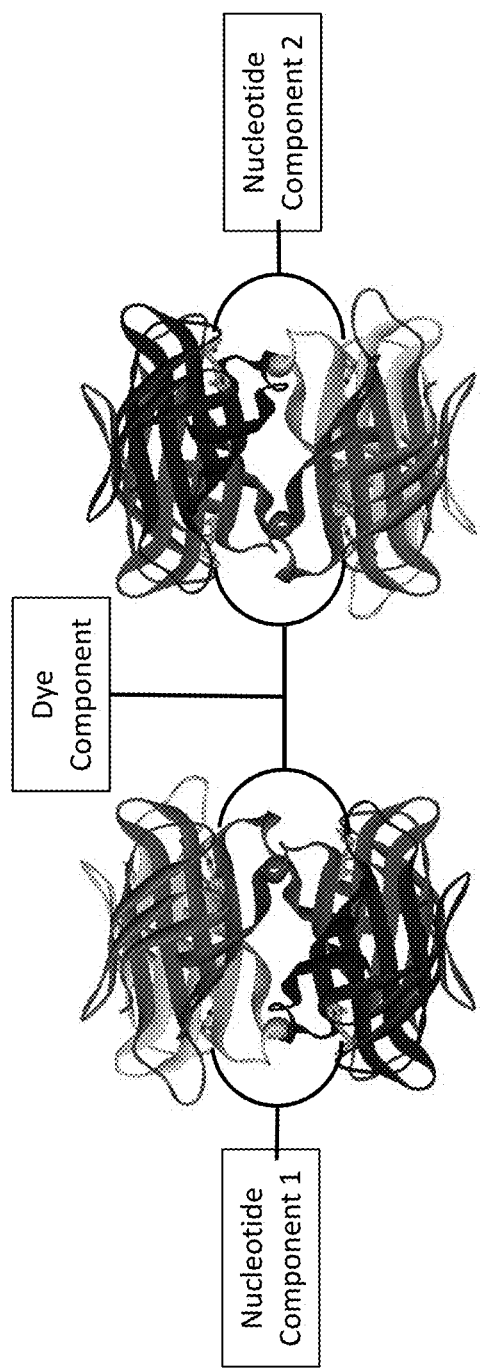
FIG. 27(A) shows a protein shield protein shield nucleotide analog of the invention having two avidins held together through a tetra-biotin moiety made of two bis-biotins and having a dye component. Each avidin protein has a nucleotide component connected through a bis-biotin moiety.

FIG. 27(A) shows a protein shield nucleotide analog of the invention comprising two avidin proteins. The analogs have a dye component that is part of a central tetra-biotin compound having two bis-biotin moieties and having two nucleotide components, each attached to one of the avidin proteins through a bis-biotin moiety. The dye components, nucleotide components, bis-biotin moieties, and avidin proteins can comprise any of those referred to or described herein. The dye component can comprise any suitable number and type of dye moiety, and the nucleotide component can comprise any suitable number and type of phospholinked nucleotide moiety. As described herein, these types of protein shielded nucleotides can be made to prevent the dye component from directly interacting with the polymerase, thereby improving the photostability of a real-time single molecule sequencing system. The nucleotide components attached to each of the two avidin proteins can be the same or different components. In some cases, the two nucleotide components are the same.

The dye component can have one or more dye moiety. For example, the nucleotide analog can have from about 1 to about 100 dye moieties, about 1 to 50 dye moieties, about 1 to about 18 dyes moieties, or 1, 2, 3, 4, 5, 6, 7, 8, 9, 10, 11, 12, 13, 14, 15, 16, 17, or 18 dye moieties. In some cases, the nucleotide analog has at least about 1 to about 18 dyes moieties, or at least about 1, 2, 3, 4, 5, 6, 7, 8, 9, 10, 11, 12, 13, 14, 15, 16, 17, or 18 dye moieties. In some cases the dye component includes FRET dyes, for example having one donor and one acceptor, two donors and one acceptor, two donors and two acceptors, etc. The number of dyes can be selected and readily tested for performance. In general, having more than one dye can be used to obtain higher brightness, but as is known in the art, the addition of one more dye does not always increase the brightness commensurate with the number of dyes. Those of skill in the art will understand how to attach the dyes and chose the number of dyes with the best performance for a given system. The type of linkers used to attach the dyes including the length of the linker and its chemical functionality can also be used to engineer the appropriate label performance. Typically the dye moieties are fluorescent dyes. In some cases, the dye moieties comprise fluorescent particles, or other luminescent species.

The nucleotide component can have one or more phospholinked nucleotide. It is important for many real-time single molecule systems that the nucleotide moiety be phospholinked. In this way, the cleavage of the alpha-beta phosphodiester bond in the nucleotide analog releases the labeled component. For example, the nucleotide analog can have from about 1 to about 100 phospholinked nucleotide moieties, about 1 to 50 phospholinked nucleotide moieties, about 1 to about 18 phospholinked nucleotide moieties, or 1, 2, 3, 4, 5, 6, 7, 8, 9, 10, 11, 12, 13, 14, 15, 16, 17, or 18 phospholinked nucleotide moieties. In some cases, the nucleotide analog has at least about 1 to about 18 phospholinked nucleotide moieties, or at least about 1, 2, 3, 4, 5, 6, 7, 8, 9, 10, 11, 12, 13, 14, 15, 16, 17, or 18 phospholinked nucleotide moieties.

Typically, the nucleotide analogs of FIG. 27(A) are formed by a first reaction of the dye component having two bis-biotin moieties to form an intermediate in which each of the two avidin proteins (e.g. streptavidin) have two open binding sites. This reaction can be carried out, for example, by using an excess of avidin protein, then purifying the desired compound from the unreacted avidin protein. The nucleotide components comprising bis-biotin moieties are then connected to form the nucleotide analog. Where the two nucleotide analogs are the same, this can be accomplished in one step, typically followed by purification.

While it is typically preferred to have the dye component between the two avidin proteins, and have the nucleotide components on the outside of the two avidin proteins, in some cases the reverse configuration is used where then nucleotide component is connected to the central tetra-biotin comprising two bis-biotins, and dye components are on the outside of the avidin proteins connected through bis-biotin moieties. For these constructs the dye components on each of the avidin proteins can be the same or can be different.

Figure 27B:
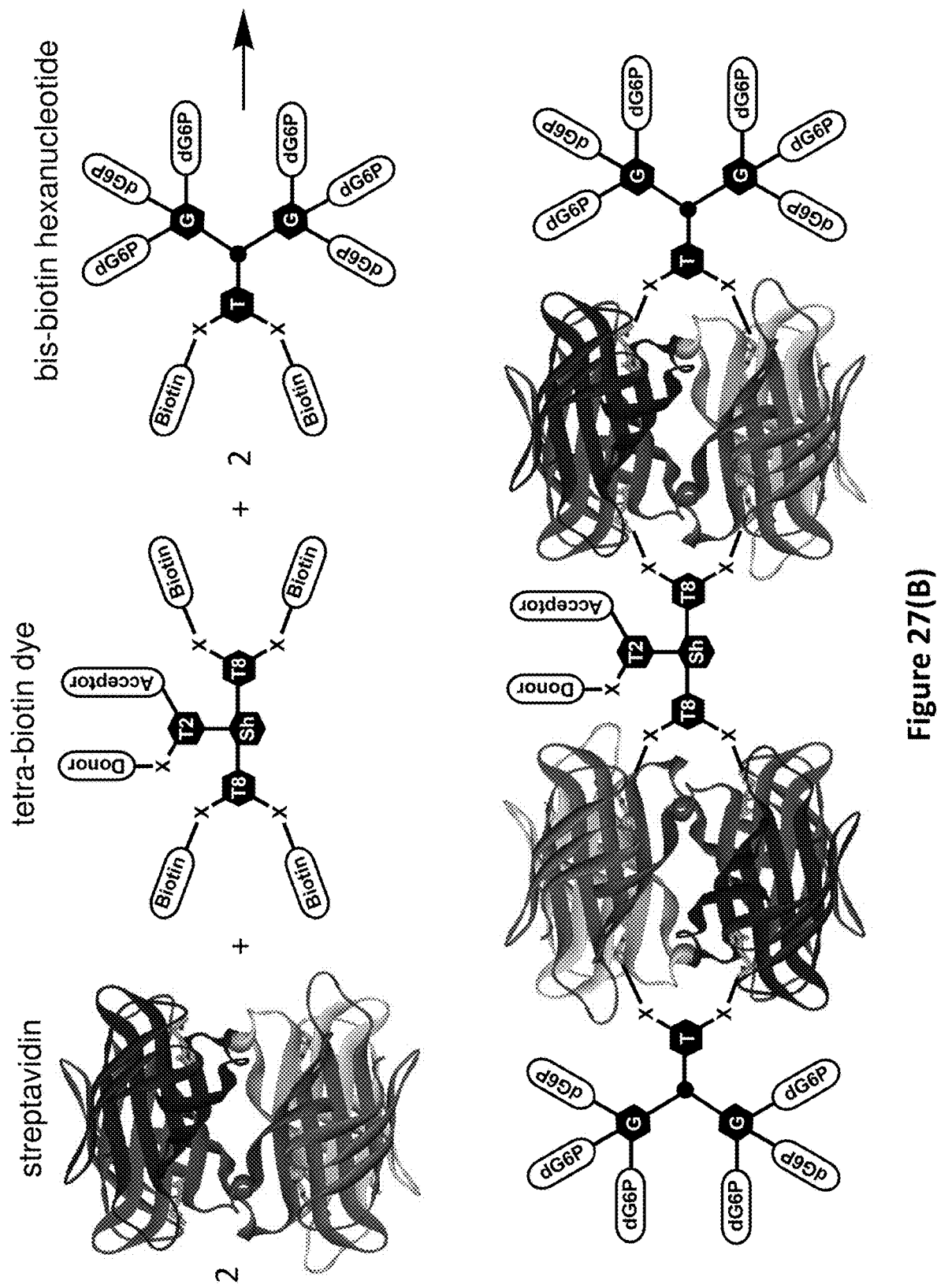
FIG. 27(B) shows an exemplary protein shield nucleotide of the invention where the central tetra-biotin moiety has a dye component with two dyes, and each streptavidin has a nucleotide component with six phospholinked nucleotide moieties attached through a bis-biotin moiety.

FIG. 27(B) shows an exemplary nucleotide analog of the invention comprising two avidin proteins. The two avidin proteins, e.g. streptavidin, are connected with a tetra-biotin compound having two bis-biotin moieties connected to one another through a trifunctional linker Sh. The trifunctional linker Sh is also connected to trifunctional linker T2 which has two dye moieties connected to it in which one dye moiety is a FRET donor connected through a linker X, and the other dye moiety is a FRET acceptor. The nucleotide analog has 12 phospholinked nucleotides with 6 phospholinked nucleotides attached to each avidin protein. The phospholinked nucleotides are for example dG connected through a hexaphosphate (dG6P). These are connected in groups of three to a tetrafunctional linker G, which is connected to the bis-biotin moiety through a trifunctional linker.

FIG. 27(B) also illustrates that the nucleotide analog having two avidin proteins can be formed from streptavidin, a tetra-biotin having a dye component, and a bis-biotin hexanucleotide. Typically the preparation would be carried out in two steps, first coupling the tetra-biotin dye, then subsequently coupling the bis-biotin hexanucleotide.

Figure 28:
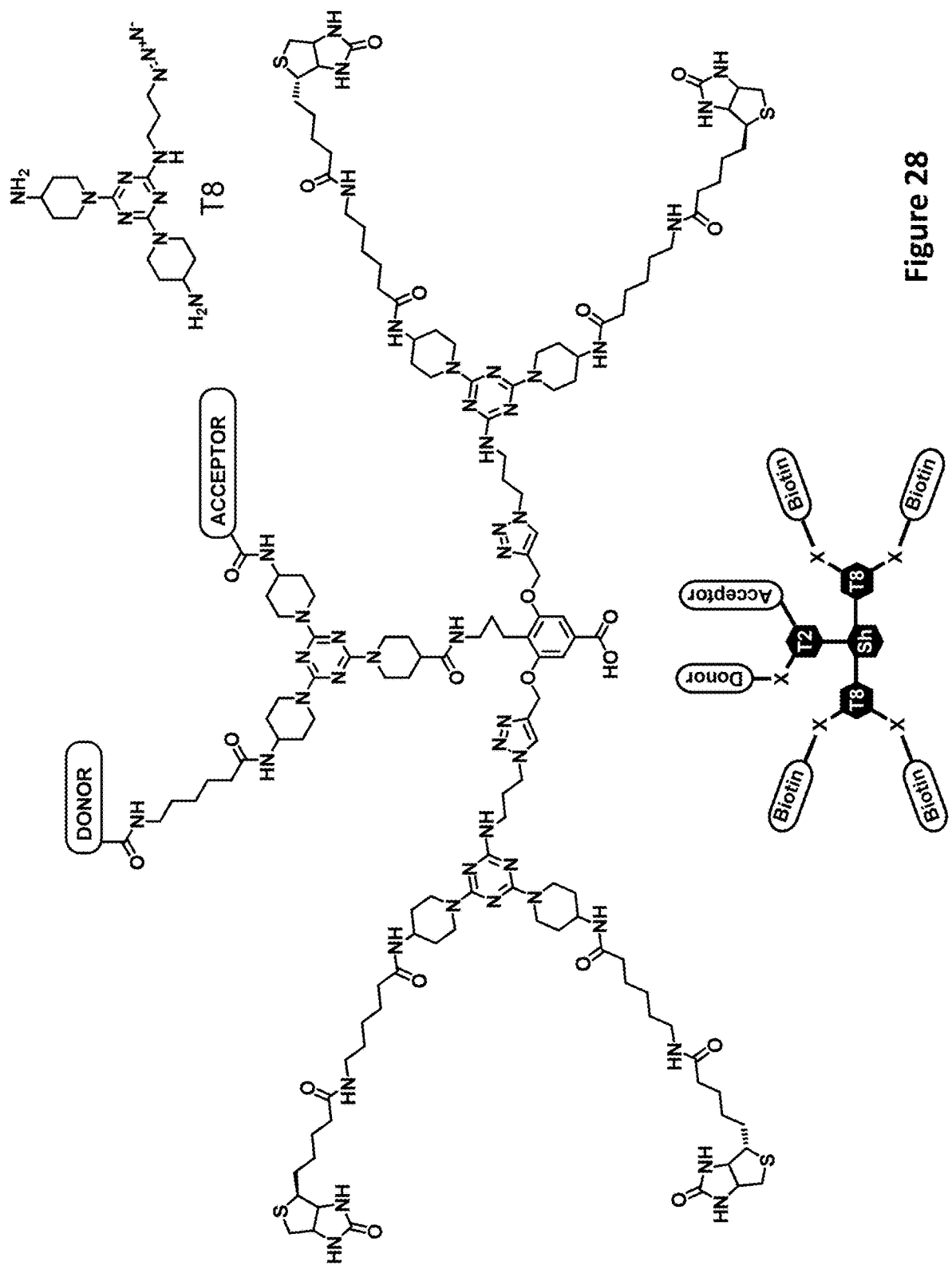
FIG. 28 shows an exemplary tetra-biotin dye component having two dyes, one being a FRET donor, and the other being a FRET acceptor. The figure also shows T8, an exemplary trifunctional linker that can be used to make such a tetra-biotin dye component.

FIG. 28 shows an example of a tetra-biotin dye component that can be used to produce nucleotide analogs of the invention. The two bis-biotin moieties have biotins connected to a trifunctional linker T8 through an amino hexanamide linker. These bis-biotin moieties are each connected to a trifunctional linker Sh, which is also connected to a trifunctional linker T2 which has donor and acceptor dyes connected to it. This tetra-biotin dye component can be prepared using standard organic chemistry.

We have found that it can be quite advantageous for the performance of the protein shielded nucleotide analog to have multiple charged groups. In some cases the multiple charged groups are anionic. In some cases the multiple charged groups comprise carboxylate, sulfonate, sulfate or phosphate groups. In one preferred approach, the protein shield nucleotide analog comprises multiple sulfonate ($—SO_3^-$) groups. For example, the nucleotide analog can have 6 to 50 sulfonate groups, 9 to 40 sulfonate groups, or 10 to 30 sulfonate groups. In some cases, multiple sulfonate groups are included in a bis-biotin compound comprising the nucleotide component. In some cases, the bis-biotin comprising the nucleotide component has from 6 to 50 sulfonate groups, 9 to 40 sulfonate groups, or 10 to 30 sulfonate groups. In some cases the bis-biotin comprising the nucleotide component has 6, 7, 8, 9, 10, 11, 12, 13, 14, 15, 16, 17, 18, 19, 20, 21, 22, 23, 24, 25, 26, 27, 28, 29, or 30 sulfonate groups. In some cases, the bis-biotin comprising the nucleotide component at least about 6, 7, 8, 9, 10, 11, 12, 13, 14, 15, 16, 17, 18, 19, 20, 21, 22, 23, 24, 25, 26, 27, 28, 29, or 30 sulfonate groups.

We have found that one particularly useful way to introduce sulfonate groups into the nucleotide analog is to include one or more six membered aromatic rings each having multiple sulfonate groups attached to it, which we refer to as a kinetic modifier group, for example, a six membered aromatic ring having 2, 3, 4, or 5 sulfonate groups attached. One particularly useful group for attaching multiple sulfonate groups to the nucleotide analogs of the invention is an SG group as shown below:

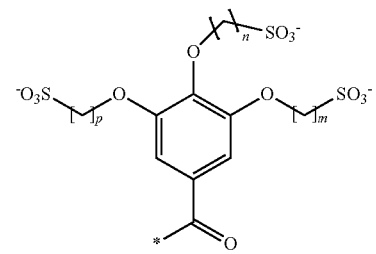

where m, n, and p are independently selected 1-18. In some cases m, n, and p are each 3, 4, 5, or 6. In some cases m, n, and p are each 3.

We have found that the inclusion of 2, 3, 4, 5, 6, 7, 8, 9, 10, 11, or 12 of these kinetic modifier groups can produce a protein shielded nucleotide analog with improved kinetic performance in sequencing.

Figure 36:
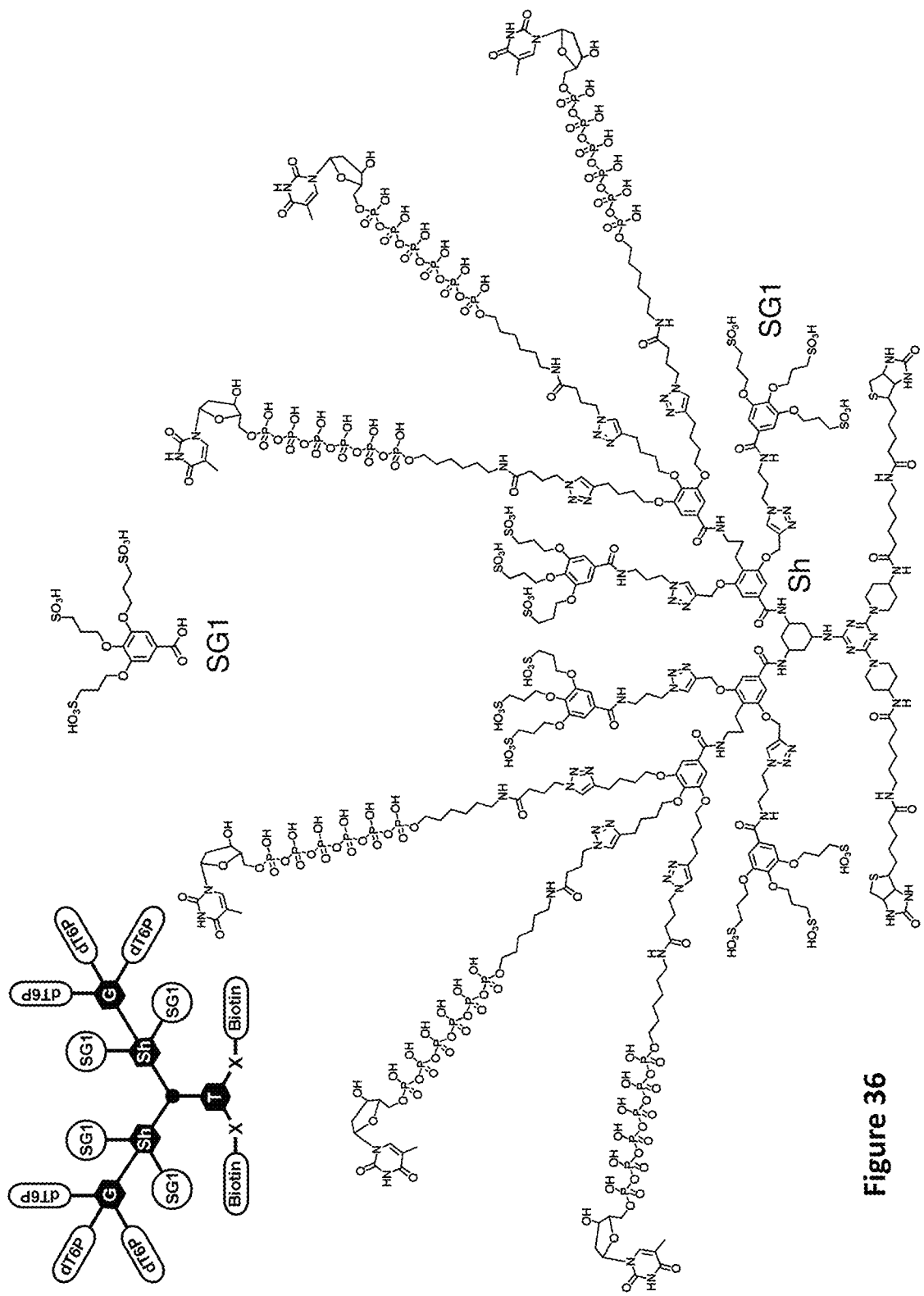
FIG. 36 shows an exemplary bis-biotin compound having six phospholinked nucleotides and having four kinetic modifier groups.

FIG. 36 shows an exemplary bis-biotin compound having six phospholinked nucleotides and having four kinetic modifier groups. For this compound four kinetic modifier groups SG1, shown in the figure is used.

The structures below provides an exemplary bis-biotin compound having two dye moieties for use in producing a nucleotide analog of the invention.

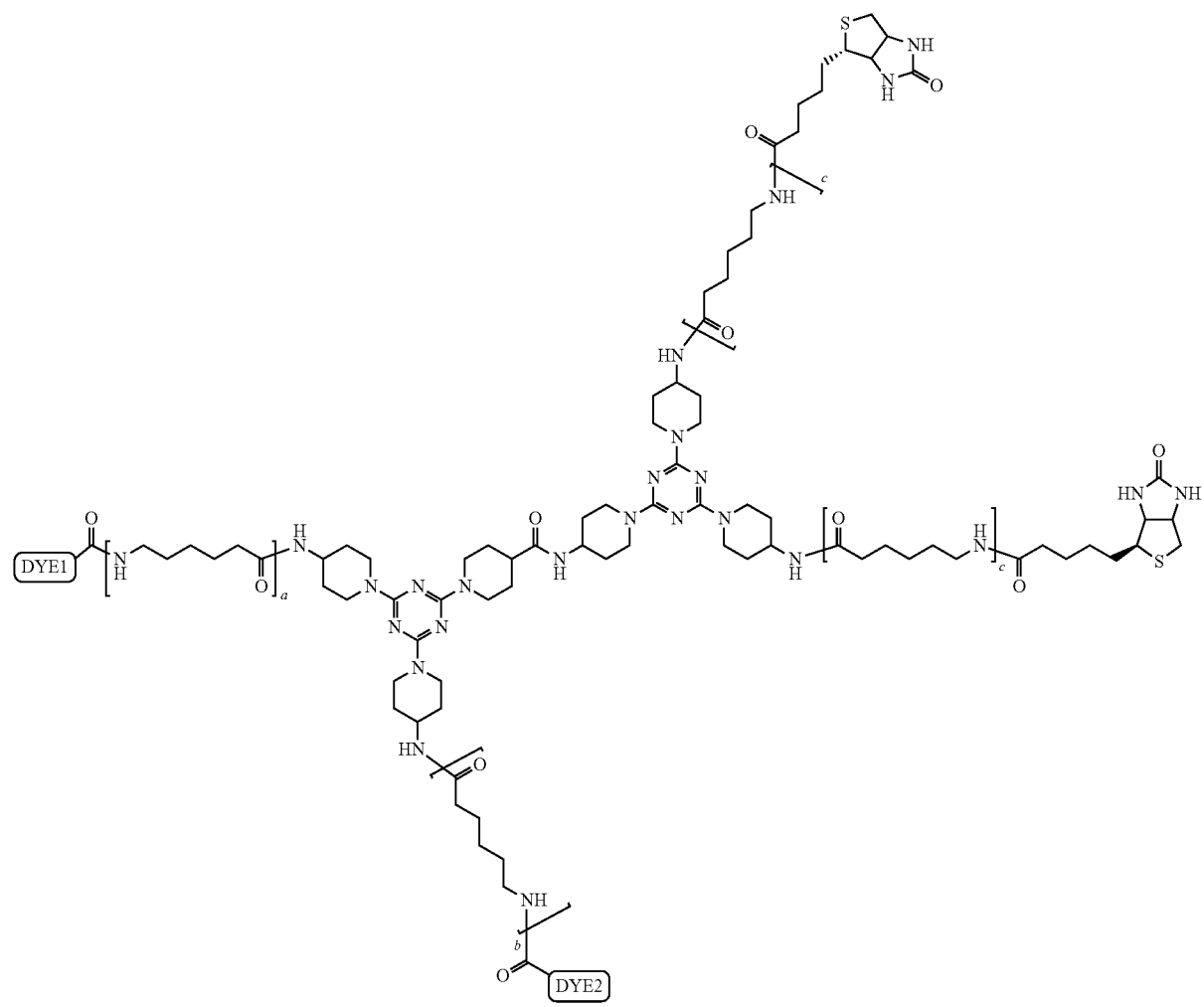
where a=0-1; b=0-1; c=1-2; Dye 1 and Dye2 are selected from the Table 4.
The structure below provides an exemplary bis-biotin compound having a single dye moiety.

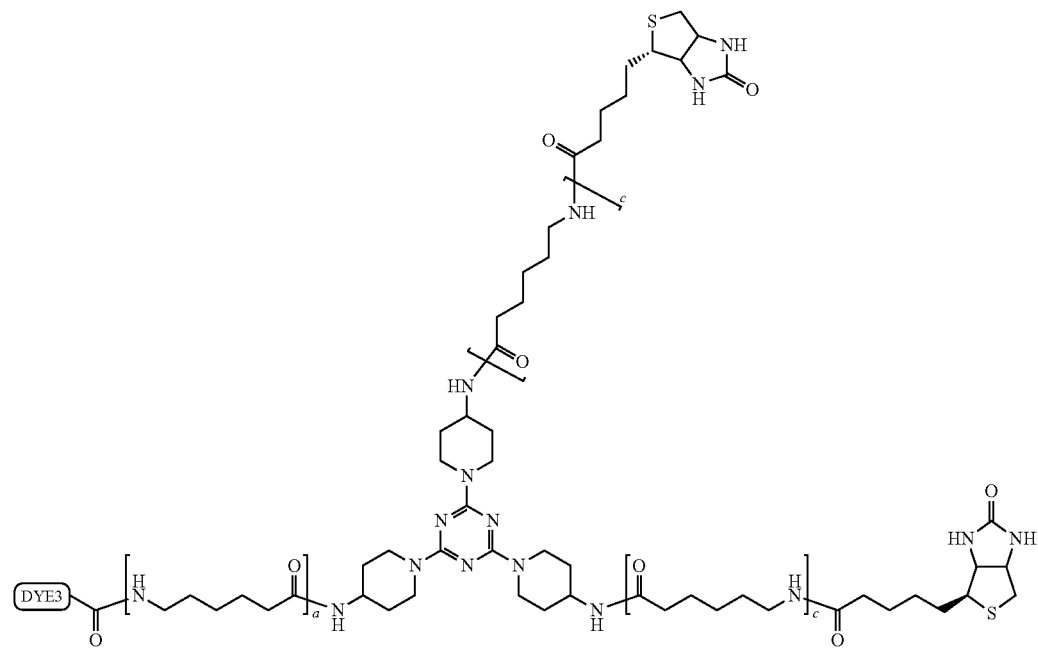
where a=0-1; c=1-2; and Dye3 is selected from the Table 4.
TABLE 4
Exemplary Fluorescent Dyes
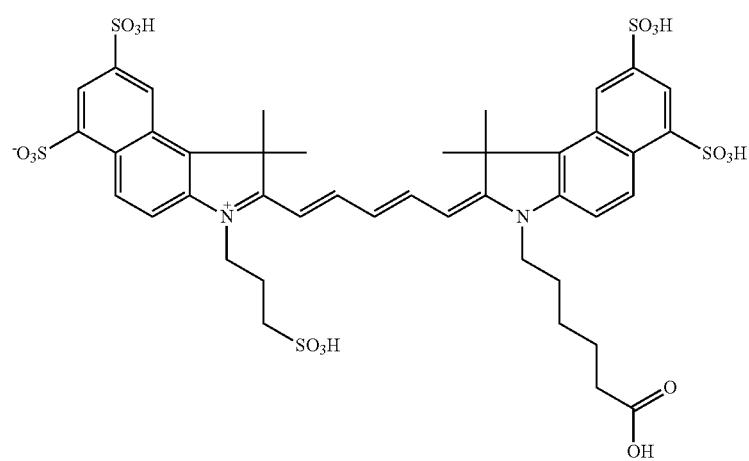

TABLE 4-continued
Exemplary Fluorescent Dyes
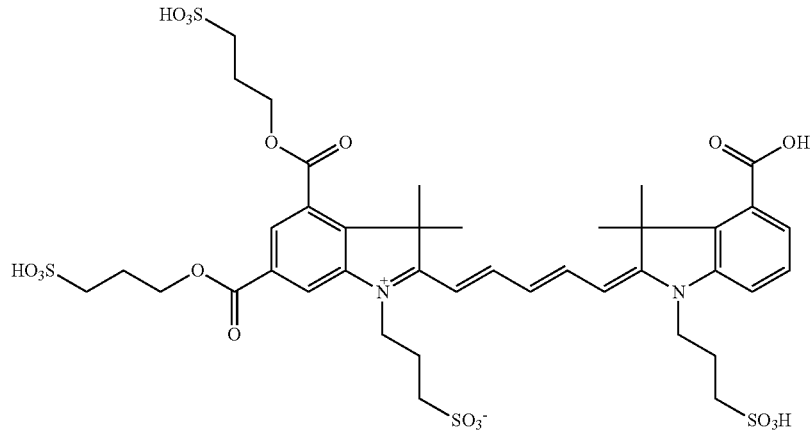
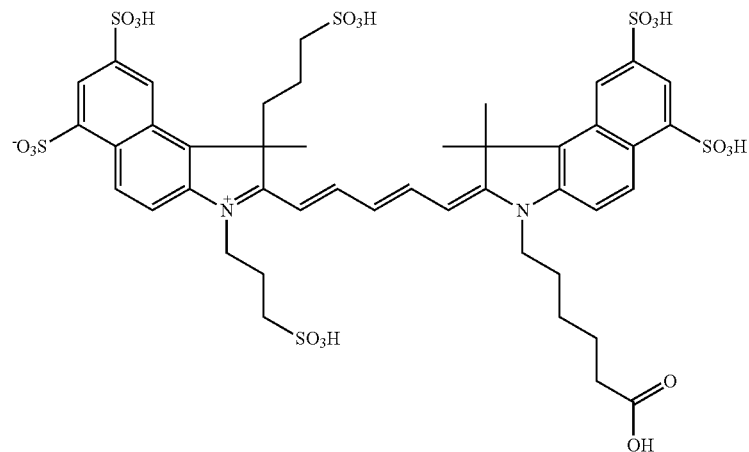
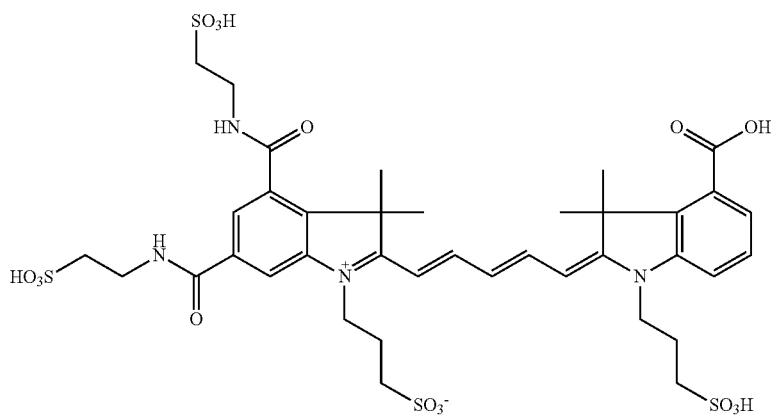

TABLE 4-continued
Exemplary Fluorescent Dyes
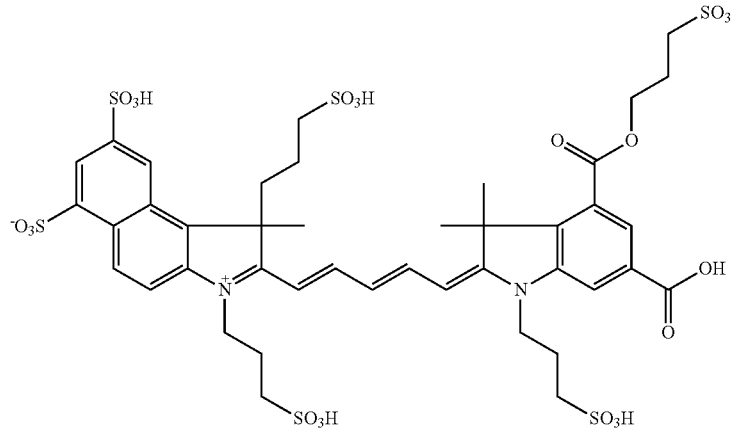
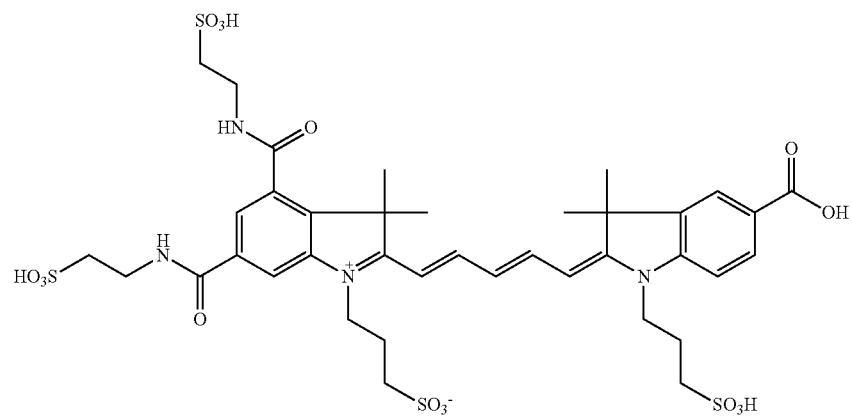
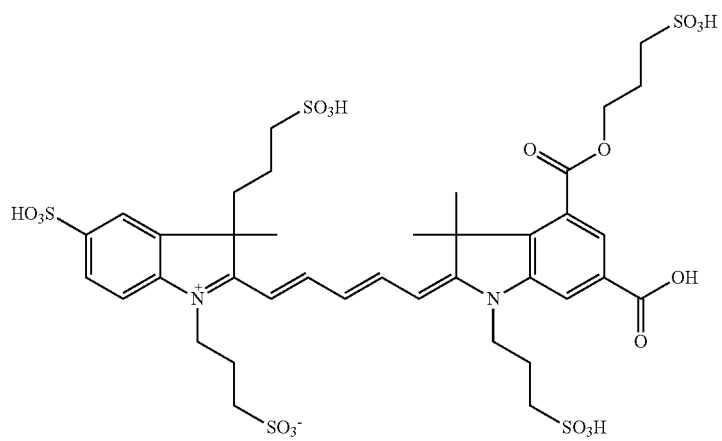

TABLE 4-continued
Exemplary Fluorescent Dyes
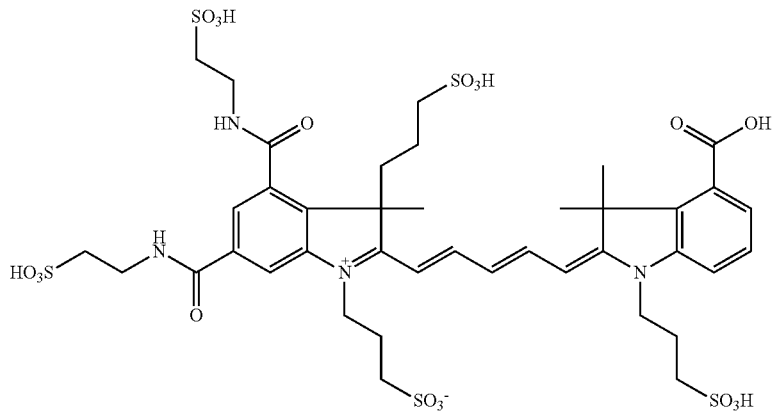
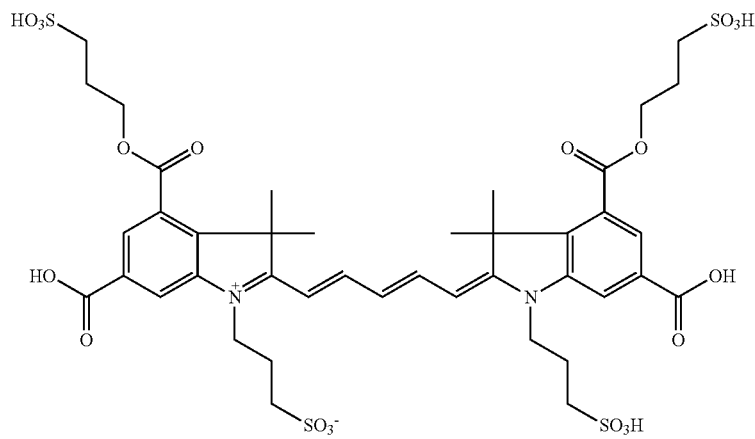
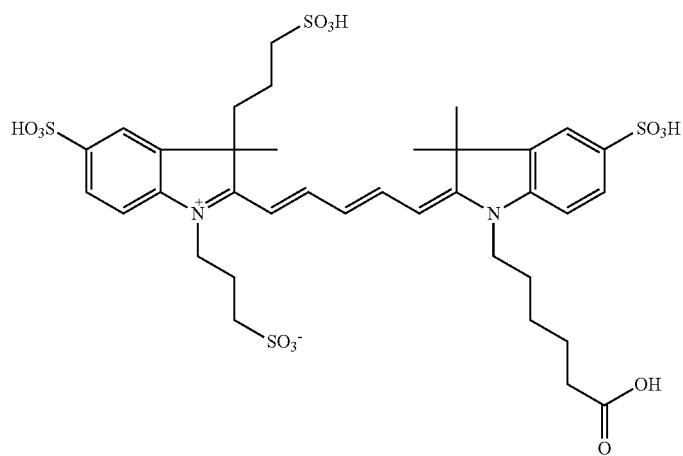

TABLE 4-continued
Exemplary Fluorescent Dyes
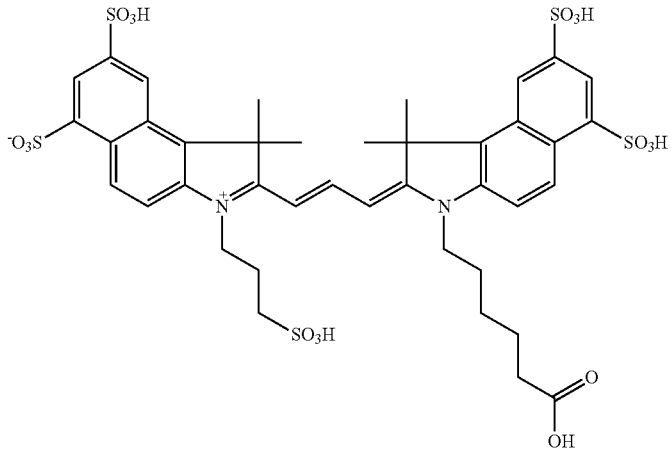
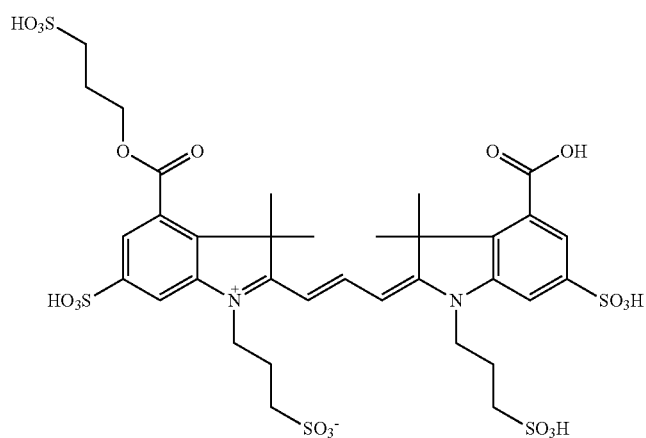
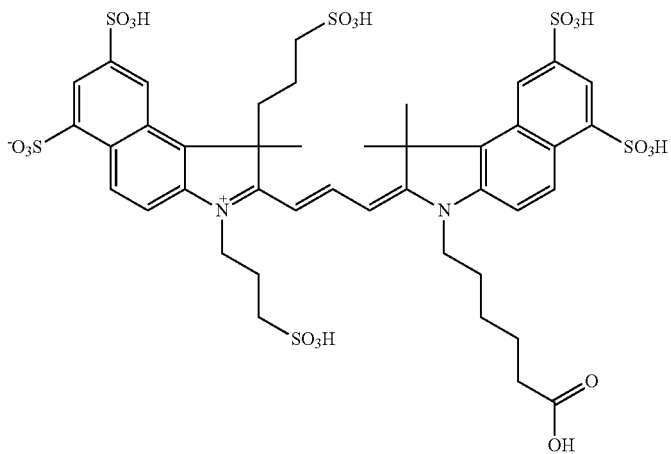

TABLE 4-continued
Exemplary Fluorescent Dyes
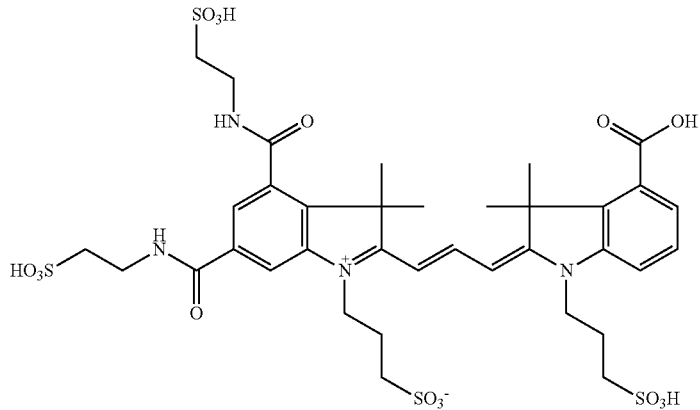
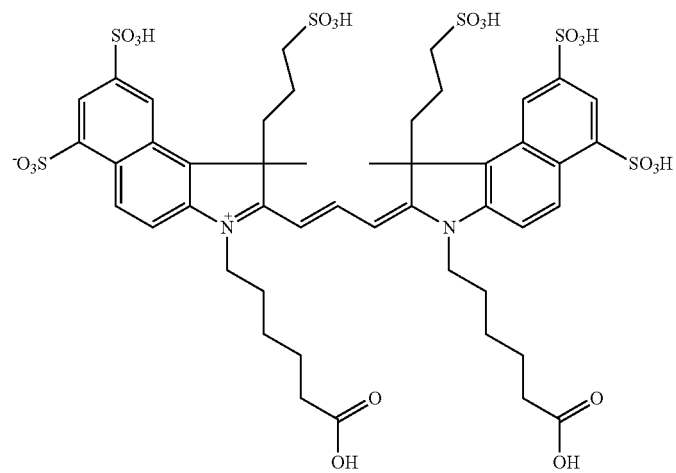
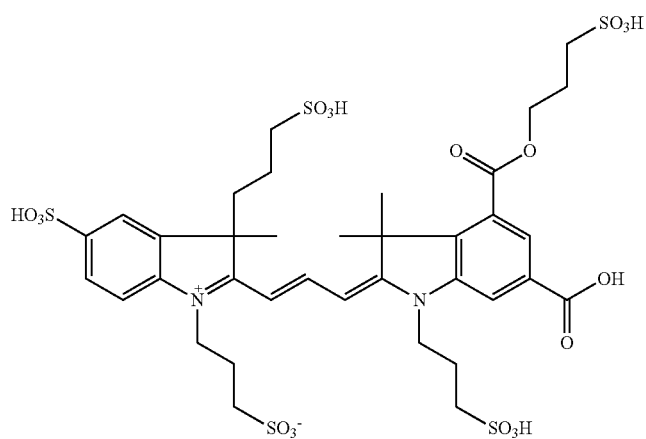

TABLE 4-continued
Exemplary Fluorescent Dyes
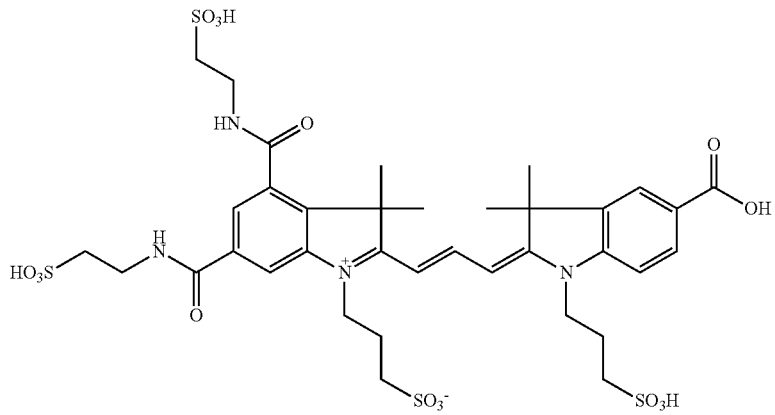
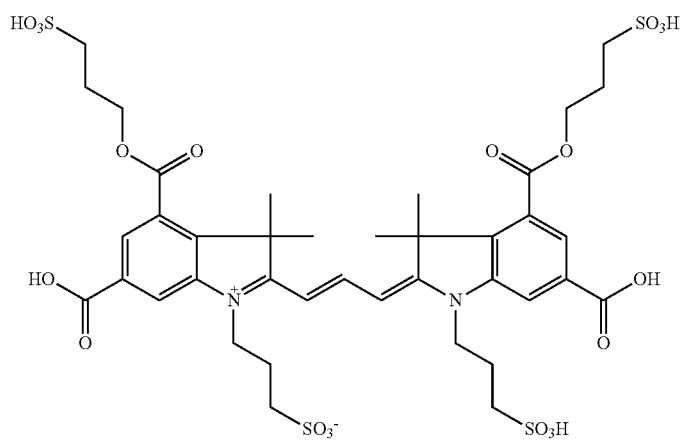
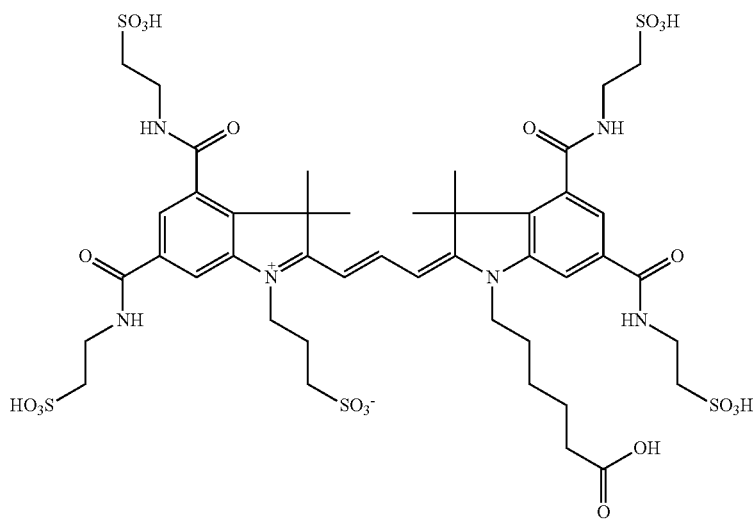

TABLE 4-continued

Exemplary Fluorescent Dyes

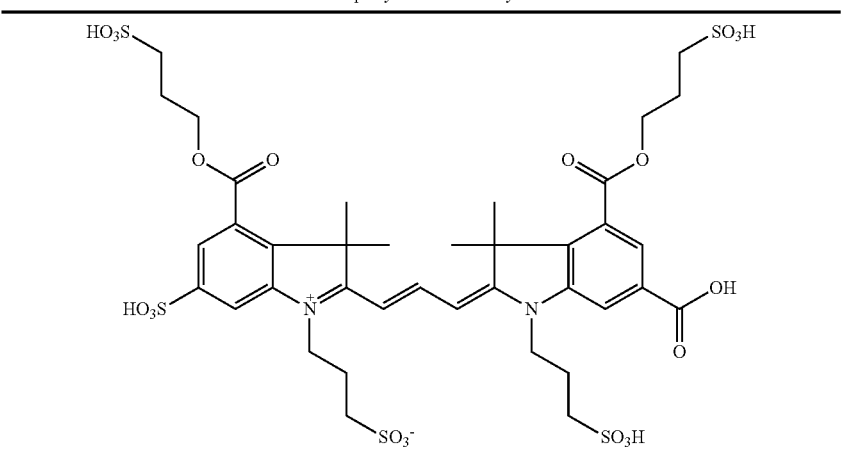

The exemplary compounds shown above are not meant to be limiting but to illustrate some ways in which one of ordinary skill can carry out the invention. The compounds can be prepared by standard organic chemistry techniques, and bis biotin compounds having any suitable type and number of dye moiety can be analogously provided. As described herein, in some cases, the dye moieties comprise fluorescent dyes. Table 4 provides structures of some exemplary fluorescent dyes that can be used. As described herein, it is typically desired that the nucleotide analogs of the invention be used in aqueous solution, and therefore that the dye moieties are soluble in water. As illustrated in the table, the dye moieties of the invention will typically have polar and/or ionic groups in order to provide solubility. A particularly useful solubilizing group is a sulfonate ($-SO_3^-$) group.

In some, the four binding sites on streptavidin can be thought of as two pairs of sites where the sites within the pair are closer together than the sites pairs are from one another. Thus, one can selectively functionalize one pair of sites with dye moieties, and the other pair of sites with nucleotide moieties to ensure that they are far enough apart such that when the nucleotide moiety is associated with the polymerase enzyme, the dye moiety does not come into contact with the polymerase enzyme.

The protein shields of the invention do not typically include short proteins and peptides of fewer than about 60 amino acids. Even where these oligo-proteins are rigid, such as poly-proline linkers in some cases are not included in the invention.

It is understood in the literature how to direct dyes and nucleotides to distinct monomers within the streptavidin tetramer. Protocols are described for forming a tetramer containing 1. 2, 3, or 4 monomers incapable of binding biotin. See e.g. Howarth et al Nature Methods 2006, which is incorporated herein by reference for all purposes. The introduction of single cysteine residues within streptavidin can also be used for example for providing conjugation sites that are chemically orthogonal to biotin. In one example of a heterotetramer a mixed heterotetramer with 2 subunits containing reactive cysteines, and two subunits capable of binding biotin is used. In another example, the subunits can be assembled separately. A maleimide PEG-N3 and maleirnide PEG alkvne can be assembled using click chemistry. This yields an assembly with a large spatial segregation of dye and nucleotide. Any suitable dye (or nucleotide) conjugated with a single reactive PEG moiety may also be substituted for one of the tetramers.

Any of the nucleotide moieties or fluorescent moieties can be connected to the shielding protein by a linker. The linker can have any suitable molecular structure. It can include, for example, alkanes, hydroxyls, phosphates, peptides, glycols, or saccharide linkages. It is generally preferred that a polar or hydrophilic linker be used in order to enhance water solubility. The length of the linker is selected in order to allow the moiety freedom to move with respect to the protein, but to prevent contact of the fluorescent moiety with the polymerase when the nucleotide moiety is associated with the polymerase.

Polar and ionic groups are also often added to portions of the nucleotide analog in order to improve water solubility as most sequencing reactions are carried out in aqueous environments. For example, carboxylic acid groups, sulfate groups, sulfonate groups, phosphate groups and/or amine groups are added to the dye moieties, bis-biotin moieties, pholinked nucleotide moieties or other portions of the nucleotide analog to ensure adequate aqueous solubility. In preferred embodiments, as described herein, multiple sulfonate ($-SO_3^-$) groups are attached to the linkers, in particular the linkers connecting the phospholinked nucleotide moieties. We have found that the inclusion of the sulfonate groups can enhance the kinetic performance of the nucleotide analogs. One particularly useful way to introduce sulfonate groups into the nucleotide analog is to include one or more six membered aromatic rings each having multiple sulfonate groups attached to it, which we refer to as a kinetic modifier group, for example, a six membered aromatic ring having 2, 3, 4, or 5 sulfonate groups attached.

In some cases, the rigidity of the linker is controlled in order to hold the relevant component in the appropriate position. For example, rigid components such as connected aromatic rings can be used in order to control the rigidity of the linker. Another way to control the rigidity of the linker and the position of a dye or nucleotide component is to use a nucleic acid linker such as DNA or a derivative thereof such as PNA. For example, it is known that stretches of double stranded DNA can be relatively rigid, allowing for controlling the position of the component attached thereto. In some embodiments, the linkers comprise double-stranded nucleic acid portions such as double-stranded DNA portions.

The dye moieties can comprise any suitable luminescent label. Typically the dye moieties are fluorescent moieties. Fluorescent moieties can have any suitable fluorescent dye or fluorescent particle or combination thereof. The fluorescent moiety provides a signaling function, absorbing the incident excitation light and giving off emitted light. Detectors are used to determine the level of emitted light, allowing for determining whether a molecule having a given fluorescent moiety is within an observation volume. In sequencing reactions, generally multiple nucleotide analogs are employed, each corresponding to a different base, and each emitting at a color that is distinct from the other analogs. In some cases, the dye moieties can comprise phosphorescent moieties.

A fluorescent moiety or fluorophore (F) can be selected from fluorescent labeling groups including individual fluorophores and cooperative fluorophores, e.g., one or both members of a donor-quencher or FRET pair. In the case where F is at least one member of a cooperative fluorophore pair, the second member of the pair may also be included within the F group, e.g., as a unified FRET dye structure (See, e.g., U.S. Pat. No. 5,688,648 for a discussion of FRET dyes), or it may be provided elsewhere on the analog or the overall system. For example, in some cases, the other member of the pair may be coupled to and as a portion of the Base moiety attached to the sugar group (See, e.g., U.S. Pat. No. 6,232,075 previously incorporated herein by reference). Alternatively, the other member of the pair may be coupled to another reaction component, e.g., a polymerase enzyme (See, e.g., U.S. Pat. No. 7,056,676, previously incorporated herein by reference).

A wide variety of different types of fluorophores are readily available and applicable to the compounds of the invention and include fluorescein, or rhodamine based dyes, cyanine dyes and the like. A variety of such dyes are commercially available and include the Cy dyes available from GE Healthcare (Piscataway, N.J.), such as Cy3, Cy5, and the like, or the Alexa® family of dyes available from Invitrogen/Molecular Probes (Carlsbad, Calif.), such as Alexa 488, 500, 514, 532, 546, 555, 568, 594, 610, 633, 647, 660, 680, 700, and 750. These fluorophores may be present as individual fluorophores or they may be present in interactive pairs or groups, e.g., as fluorescent resonant energy transfer (FRET) pairs.

Alternative labeling strategies may employ inorganic materials as labeling moieties, such as fluorescent or luminescent nanoparticles, e.g. nanocrystals, i.e. Quantum Dots, that possess inherent fluorescent capabilities due to their semiconductor make up and size in the nanoscale regime (See, e.g., U.S. Pat. Nos. 6,861,155, 6,699,723, 7,235,361). Such nanocrystal materials are generally commercially available from, e.g., Invitrogen, Inc., (Calsbad Calif.). Again, such compounds may be present as individual labeling groups or as interactive groups or pairs, e.g., with other inorganic nanocrystals or organic fluorophores.

Suitable fluorescent moieties are described in copending U. S. Patent Applications 2012/0077189, 2012/0058482, 2012/0058469, and 2012/0052506, which are incorporated herein by reference in their entirety for all purposes.

In preferred aspects of the invention, the template nucleic acid is in a cyclic form. Performing single-molecule sequencing on a cyclic nucleic acid template is advantageous in that it allows for redundant sequencing of a given region. The accuracy of a sequence determination can be improved significantly by sequencing the same region multiple times. Cyclic nucleic acids that are highly useful for the current invention include SMRT Bell™ templates, which are nucleic acids having a central double-stranded region, and having hairpin regions at each end of the double-stranded region. The preparation and use of cyclic templates such as SMRT Bells™, are described for example in U.S. patent application Ser. No. 12/286,119, filed Sep. 26, 2008, and U.S. patent application Ser. No. 12/383,855, filed Mar. 27, 2009, the full disclosure of which is incorporated herein by reference for all purposes. One advantage of the SMRT Bell™ template is that it can be made from a library of double-stranded nucleic acid, e.g. DNA, fragments. For example, a sample of genomic DNA can be fragmented into a library of DNA fragments, by known methods such as by shearing or by use of restriction enzymes. The library of DNA fragments can be ligated to hairpin adaptors at each end of the fragment to produce a library of SMRT Bell™ templates. The hairpin adaptors provide single stranded regions within the hairpins. By using the same hairpin adaptor for all of the fragments, the hairpin adaptors, provide a position for universal priming of all of the sequences.

Methods for treating the surfaces of zero mode waveguides including methods for obtaining selective coupling to the base of the zero mode waveguides are described, for example, in U.S. Pat. Nos. 7,833,398, 7,292,742 and in U.S. Patent Application Nos. 2008/0032301, 2008/0241892, and 2008/0220537, the full disclosures of which are incorporated by reference herein for all purposes. In some cases, for example biotin is selectively coupled to the base of the zero mode waveguide.

The template nucleic acid can be derived from any suitable natural or synthetic source. In preferred embodiments, the template comprises double stranded DNA, but in some circumstances double-stranded RNA or RNA-DNA heteroduplexes can be used. The template nucleic acid can be genomic DNA from eukaryotes, bacteria, or archaea. The template nucleic acid can be cDNA derived from any suitable source including messenger RNA. The template nucleic acid can be a library of double stranded segments of DNA. The template nucleic acid can be linear or circular. For example, the nucleic acid can be topologically circular and have a linear double stranded region. A circular nucleic acid can be, for example, a gapped plasmid. The nucleic acid is a double stranded linear DNA having a gap in one of the strands. The gap provides a site for attachment of the polymerase enzyme for nucleic acid synthesis. The linear double stranded DNA having a double-stranded DNA adaptor can be made by ligation of DNA fragment to an adaptor through blunt end—ligation or sticky end ligation. The ligation produces a linear DNA having a gap close to the 5' end of one or both of the strands. The gap can be any suitable width. For example, the gap can be from 1 to 50 bases, from 2 to 30 bases, or from 3 to 12 bases.

By "nucleic acid" or "oligonucleotide" or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones; non-ionic backbones, and non-ribose backbones, including those described in U.S. Pat. Nos. 5,235,033 and 5,034,506. The template nucleic acid may also have other modifications, such as the inclusion of heteroatoms, the attachment of labels, such as dyes, or substitution with functional groups which will still allow for base pairing and for recognition by the enzyme.

The template sequence may be provided in any of a number of different format types depending upon the desired application. The template may be provided as a circular or functionally circular construct that allows redundant processing of the same nucleic acid sequence by the synthesis complex. Use of such circular constructs has been described in, e.g., U.S. Pat. No. 7,315,019 and U.S. Patent Application No. 2009/0029385. Alternate functional circular constructs are also described in U.S. Patent Application 2009/0280538, and U.S. Patent Application 2009/0298075, the full disclosures of each of which are incorporated herein by reference in their entirety for all purposes.

Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

The nucleic acids can comprise a population of nucleic acids having universal sequence regions which are common to all of the nucleic acids in the population and also have specific regions which are different in the different members of the population. The current invention allows for capturing and isolating polymerase-nucleic acid complexes using either the universal or the specific regions.

Polymerase enzymes useful in the invention include polymerases mutated to have desirable properties for sequencing. For example, suitable enzymes include those taught in, e.g., Copending Patent Application entitled "Recombinant Polymerases for Incorporation of Protein Shield Nucleotide Analogs", U.S. patent application Ser. No. 61/794,971, filed Feb. 14, 2013, WO 2007/076057 POLYMERASES FOR NUCLEOTIDE ANALOGUE INCORPORATION by Hanzel et al., WO 2008/051530 POLYMERASE ENZYMES AND REAGENTS FOR ENHANCED NUCLEIC ACID SEQUENCING by Rank et al., and U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES." The modified polymerases may have modified properties such as decreased branch fraction formation, improved specificity, improved processivity, altered rates, improved retention time, improved stability of the closed complex, etc.

In addition, the polymerases can also be modified for application-specific reasons, such as to increase photostability, e.g., as taught in U.S. patent application Ser. No. 12/384,110 filed Mar. 30, 2009, by Keith Bjornson et al. entitled "Enzymes Resistant to Photodamage," to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

The polymerase enzymes used in the invention will generally have strand-displacement activity. Many polymerases have this capability, and it is useful in the context of the current invention for opening up and exposing the regions of a nucleic acid sample for capture by a hook molecule. In some cases, strand displacement is part of the polymerase enzyme itself. In other cases, other cofactors or co-enzymes can be added to provide the strand displacement capability.

The enzymes used in the invention can comprise DNA polymerases. DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47): 43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1): reviews 3002.1-3002.4; and Steitz (1999) "DNA polymerases: structural diversity and common mechanisms" J Biol Chem 274:17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296). In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, a M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. 129 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ 129 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, *E. coli* DNA Polymerase 1, Klenow fragment, reverse transcriptases, 129 related polymerases including wild type 129 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SFS, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. patent application Ser. No. 12/924,701, filed Sep. 30, 2010; and Ser. No. 12/384,112, filed Mar. 30, 2009.

In some embodiments, the polymerase enzyme that is used for sequencing is an RNA polymerase including an RNA dependent RNA polymerase and a DNA dependent RNA polymerase. Any suitable RNA polymerase can be used including RNA polymerases from bacteria, eukaryotes, viruses, or archea. Suitable RNA polymerases include RNA Pol I, RNA Pol II, RNA Pol III, RNA Pol IV, RNA Pol V, T7 RNA polymerase, T3 RNA polymerase or SP6 RNA polymerase. Where RNA polymerases are used, the polymerizing reagents will generally include NTPs or their analogs rather than the dNTPs used for DNA synthesis. In addition, RNA polymerases can be used with specific cofactors. There are many proteins that can bind to RNAP and modify its behavior. For instance, GreA and GreB from *E. coli* and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e. they help RNAP choose whether or not to express certain genes. RNA dependent RNA polymerases (RNA replicases) may also be used including viral RNA polymerases: e.g. polioviral 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

The use of an RNA dependent polymerase such as an RNA dependent DNA polymerase or an RNA dependent RNA polymerase allows for the direct sequencing of messenger RNA, transfer RNA, non-coding RNA, ribosomal RNA, micro RNA or catalytic RNA. The polymerase enzyme used in the methods or compositions of the invention include RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

The conditions required for nucleic acid synthesis are well known in the art. The polymerase reaction conditions include the type and concentration of buffer, the pH of the reaction, the temperature, the type and concentration of salts, the presence of particular additives which influence the kinetics of the enzyme, and the type, concentration, and relative amounts of various cofactors, including metal cofactors.

Enzymatic reactions are often run in the presence of a buffer, which is used, in part, to control the pH of the reaction mixture. Buffers suitable for the invention include, for example, TAPS (3-{[tris(hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the rate of the polymerase reaction. The temperature of the reaction can be adjusted to enhance the performance of the system. The reaction temperature may depend upon the type of polymerase which is employed.

As used in the art, the term nucleotide refers both to the nucleoside triphosphates that are added to a growing nucleic acid chain in the polymerase reaction, and also to refer to the individual units of a nucleic acid molecule, for example the units of DNA and RNA. Herein, the term nucleotide used in consistent with its use in the art. Whether the term nucleotide refers to the substrate molecule to be added to the growing nucleic acid or to the units in the nucleic acid chain can be derived from the context in which the term used.

The nucleotides or set of nucleotides used during nucleic acid synthesis are generally naturally occurring nucleotides but can also include modified nucleotides (nucleotide analogs). The nucleotides used in the invention, whether natural, unnatural, modified or analog are suitable for participation in the polymerase reaction. The term nucleotide may also be used to refer to nucleotides having other than three phosphate groups, for example 4, 5, 6, 7 or more phosphate groups. Such nucleotides have been described, for example in U.S. Pat. Nos. 6,936,702 and 7,041,812. Labels such as fluorescent dye group may be located in various positions on the nucleotide. In some cases, a fluorescent dye is located on the terminal phosphate of the nucleotide.

The nucleotide compositions may include nucleoside triphosphates, or analogs of such compounds. For example, in some cases, the reaction mixtures will include nucleotide analogs having longer phosphate chains, such as nucleoside tetra, penta-, hexa- or even heptaphosphates. In addition, the nucleotide analogs of the compositions of the invention may additionally include other components, such as detectable labeling groups. Such detectable labeling groups will typically impart an optically or electrochemically detectable property to the nucleotide analogs being incorporated into the synthesis reaction. In particularly preferred aspects, fluorescent labeling groups, i.e., labeling groups that emit light of one wavelength when excited with light of another wavelength, are used as the labeling groups. For purposes of the present disclosure, the foregoing or later discussed nucleotide or nucleotide analog compositions whether labeled or unlabeled, possessing of one or more phosphate groups, typically two or more or three or more phosphate groups, or otherwise modified, are generally referred to herein as nucleotides.

The methods, compositions, and devices of the invention are particularly useful for performing single-molecule analysis. In some cases, the substrate or chip comprises an array of nanoscale wells such as arrays of zero mode waveguides (ZMWs). For example, the substrate can have a transparent lower layer such as fused silica, upon which is deposited a cladding layer with a thickness of between about 10 nm and about 500 nm. Through the cladding layer is an array of holes extending to the transparent substrate, and in some cases extending into the transparent substrate. The holes can have any suitable profile including a circular profile. Where the holes have a circular profile, the diameter of the holes is generally from about 20 nm to about 500 nm. The holes extending to the transparent substrate will generally have a portion of the transparent substrate as their base, thus forming nanoscale wells. For use in the present invention, the arrays of nanoscale wells are typically functionalized such that binding molecules are attached at the base of the wells for binding the molecule of interest such as the polymerase-nucleic acid complex within the well. In some cases, the arrays are selectively functionalized such that a higher density of binding molecules is present within the wells than outside of the wells. Approaches to functionalizing zero mode waveguide substrates are provided in U.S. Pat. Nos. 7,833,398, 7,292,742 and in U.S. patent application Ser. No. 11/731,748, filed Mar. 29, 2007, Ser. No. 12/079,922, filed Mar. 27, 2008, and Ser. No. 12/074,716, filed Mar. 5, 2008, the full disclosures of which are incorporated by reference herein for all purposes. As described elsewhere herein, these nanoscale wells provide for carrying out analyses on very small numbers of molecules down to single molecules. In some cases the methods, devices, and compositions of the invention allow for the deposition of single molecules of interest within nanoscale wells.

The coupling groups or binding molecules on the substrate for coupling between the molecule of interest, e.g. polymerase-nucleic acid complex can be any suitable coupling group or binding molecules. The coupling can be accomplished by forming a covalent bond or through a non-covalent interaction. It is generally desired that the coupling to the substrate result in a strong bond relative to the other linkages. Many types of binding pairs are known in the art. In some cases, an interaction between biotin and a biotin binding protein such as avidin or streptavidin is used. In some cases, an antibody-antigen interaction, for example between digoxigenin and anti-digoxigenin is used. Reactions that form covalent linkages, for example SNAP or Click chemistry can be used to bind the polymerase-nucleic acid complex to the substrate. Oligonucleotide hybridization can also be used for the attachment. Where such hybridization is used, the linkages are designed such that the oligonucleotide binding to the surface is stronger, e.g. has a higher Tm than the other linkages between the surface and the bead.

Binding of the polymerase-nucleic acid complex to the substrate can be carried out by forming a bond to the polymerase. One member of the binding pair used to attach the complex to the solution is connected directly or indirectly to the polymerase. In some cases, a biotinylation sequence is included when producing the polymerase, the protein is biotinylated and attached to streptavidin prior to formation of the complex. The polymerase-streptavidin is then ready for binding to a substrate that is prepared by having biotin groups on its surface.

Where the molecule of interest comprises a polymerase-nucleic acid complex, the solution that is used for deposition with beads is generally an aqueous solution. The components of the solution and the conditions are controlled as described above in order that the polymerase-nucleic acid complex remains intact. For example, the appropriate level of monovalent and divalent ions, the concentration of nucleotide, the pH and the temperature are controlled. It is also generally desired that the polymerase not continue to perform nucleic acid synthesis during deposition, and Sr and Ca can be added in order to inhibit or reduce polymerization.

One object of the invention is providing molecules of interest such as polymerase-nucleic acid complexes to a substrate for single molecule analysis. For single molecule analysis it is generally desired that single molecules of interest are bound to a substrate at a density and pattern such that the optical signal from one molecule can be detected distinctly from signals from other molecules and from solution. That is, the molecules are deposited so as to be individually optically resolvable. One method that has been used for this purpose is to deposit molecules of interest from a solution that is diluted such that on average, an acceptable number of single molecules will be individually optically resolvable. If the concentration is too high, the density on the surface will be such that few, if any, single molecules will be resolvable. If the concentration is too low, this may also result in very few single molecules. The methods, devices and compositions of the present invention provide an alternative approach for obtaining high levels of optically resolvable single molecules on a substrate.

As described above, a preferred substrate for single-molecule analysis is a zero mode waveguide (ZMW) array. Here, the optical analysis is carried out only within the ZMWs on the surface. We have found that the invention provides useful methods for loading single-molecules into a ZMW array. As with other substrates for single molecule analysis, loading molecules of interest onto ZMWs to obtain acceptable numbers of single molecules is often carried out with the dilution method. The methods of the invention provides tools for controlling the way in which molecules of interest are loaded into ZMWs.

When depositing a library of polymerase-nucleic acid complexes onto a substrate, for example a ZMW substrate, by diffusion from solution we have found that there can be relatively a large number of smaller fragments deposited than larger fragments. We have found that by depositing with beads, there is a much more even distribution of deposited polymerase-nucleic acid complexes by size, allowing for a better representation of the larger size fragments in the data in single molecule analysis.

Since ZMWs are wells with defined dimensions, the sizes, shapes, and extension (reach) of the beads can be used to control the manner in which molecules of interest are deposited. For example in some cases, beads are used that have a size that is smaller than the ZMW, such that it fits into the ZMW, and has a reach such that only molecules of interest from a bead fitting into the ZMW will be deposited. In some cases, beads will be used that are smaller than the diameter of a ZMW, but larger than half of the diameter of the ZMW. In this way, only one bead will deposit into the ZMW, preventing the deposition of a second bead, ensuring that each ZMW will only receive molecules of interest from one bead. For example, where a ZMW array having ZMWs with diameters of 200 nm, beads having diameters from about 100 nm to about 190 nm are used. Another way of controlling the level of loading is by controlling the density of molecules of interest on the surfaces of the beads. For example, by using sparsely functionalized beads, only small numbers of molecules of interest will be deposited.

When loading a surface for single molecule analysis, generally a small amount of material is deposited as compared to the total amount on the bead. This allows for re-using the beads by removing them from the substrate, optionally storing them, and then applying them to another substrate. The beads can be re-used in some case to load substrates 1, 2, 3, 4, 5, 10, 20 or more times while still obtaining acceptable loading. We have found that after each loading, the amount loaded onto the next substrate may be slightly less, but that the levels on the later substrates are still acceptable. Comparable levels can also be obtained on later substrates by changing deposition conditions, for example by lengthening the time of deposition. The ability to re-use the beads can be important for getting the most out of small samples. The ability to store the beads for future loading and testing can be important for the integrity of the date from a study. We have also found that the beads can be stored for days, weeks, and for over a month without any measurable deterioration in properties.

The methods, devices, and compositions of the invention are particularly useful for single molecule sequencing, and specifically single molecule sequencing by incorporation in real time. For sequencing processes that rely upon monitoring of the incorporation of nucleotides into growing nascent strands being synthesized by the complex, the progress of the reaction through these steps is of significant importance. In particular, for certain "real-time" nucleotide incorporation monitoring processes, the detectability of the incorporation event is improved based upon the amount of time the nucleotide is incorporated into and retained within the synthesis complex during its ultimate incorporation into a primer extension product.

By way of example, in certain exemplary processes, the presence of the nucleotide in the synthesis complex is detected either by virtue of a focused observation of the synthesis complex, or through the use of interactive labeling techniques that produce characteristic signals when the nucleotide is within the synthesis complex. See, e.g., Levene, et al., Science 299:682-686, January 2003, and Eid, J. et al., Science, 323(5910), 133-138 (2009), the full disclosures of which are incorporated herein by reference in their entirety for all purposes.

Figure 29:
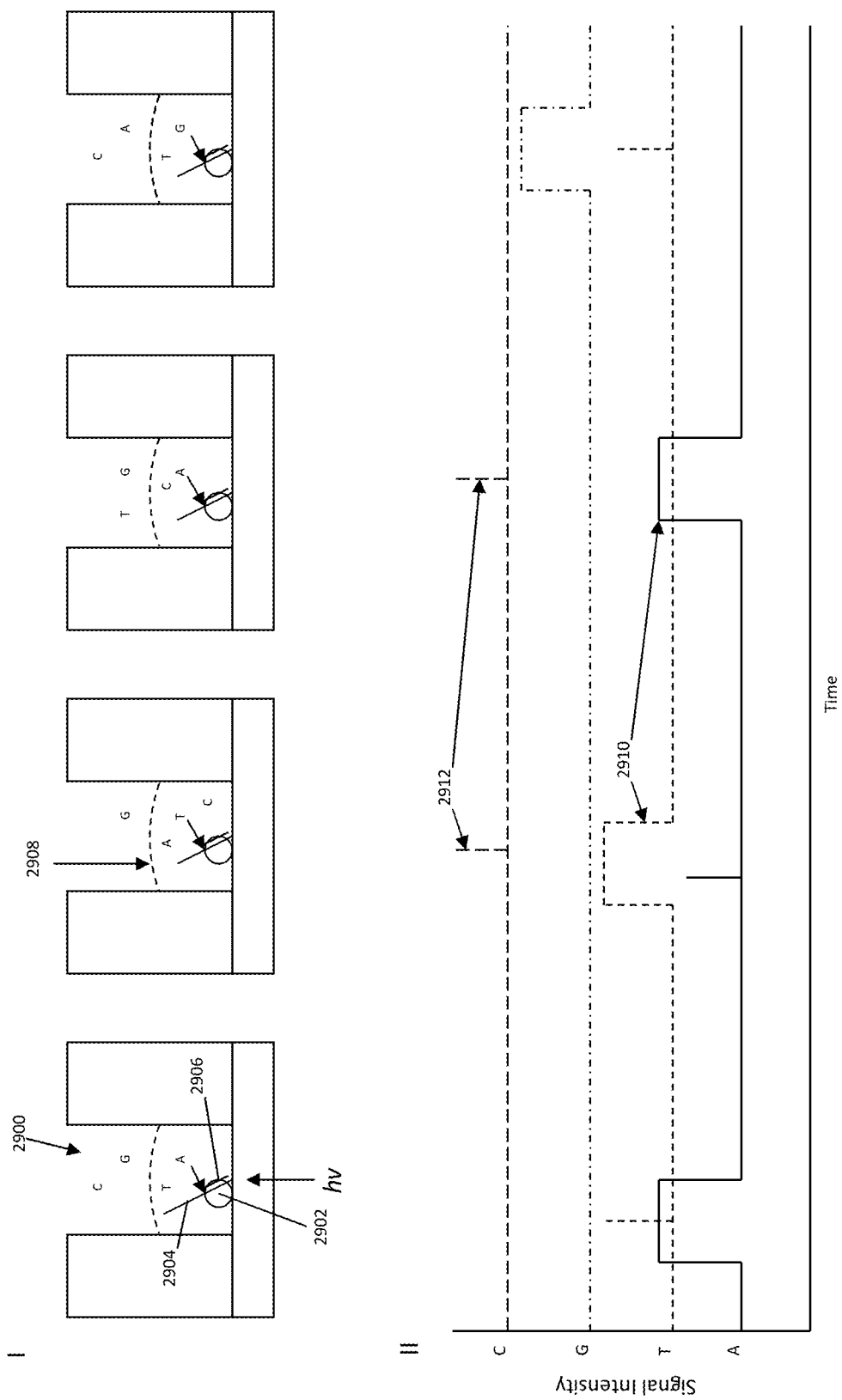
FIG. 29 shows a schematic showing one way of carrying out real-time single molecule nucleic acid sequencing. Panel (I) shows the sequencing process involving observing a polymerase within an observation volume, Panel (II) shows an exemplary plot of signal intensity versus time during the sequencing process.

In the first exemplary technique, as schematically illustrated in FIG. 29, a nucleic acid synthesis complex, including a polymerase enzyme 2902, a template sequence 2904 and a complementary primer sequence 2906, is provided immobilized within an observation region 2900, that permits illumination (as shown by hv) and observation of a small volume that includes the complex without excessive illumination of the surrounding volume (as illustrated by dashed line 2908). By illuminating and observing only the volume immediately surrounding the complex, one can readily identify fluorescently labeled nucleotides that become incorporated during that synthesis, as such nucleotides are retained within that observation volume by the polymerase for longer periods than those nucleotides that are simply randomly diffusing into and out of that volume.

In particular, as shown in panel II of FIG. 29, when a nucleotide, e.g., A, is incorporated into by the polymerase, it is retained within the observation volume for a prolonged period of time, and upon continued illumination yields a prolonged fluorescent signal (shown by peak 2910). By comparison, randomly diffusing and not incorporated nucleotides remain within the observation volume for much shorter periods of time, and thus produce only transient signals (such as peak 2912), many of which go undetected, due to their extremely short duration.

In particularly preferred exemplary systems, the confined illumination volume is provided through the use of arrays of optically confined apertures termed zero-mode waveguides, e.g., as shown by confined reaction region 100 (ZMWs)(See, e.g., U.S. Pat. No. 6,917,726, which is incorporated herein by reference in its entirety for all purposes). For sequencing applications, the DNA polymerase is provided immobilized upon the bottom of the ZMW (See, e.g., Korlach et al., PNAS U.S.A. 105(4): 1176-1181. (2008), which is incorporated herein by reference in its entirety for all purposes.

In operation, the fluorescently labeled nucleotides (shown as A, C, G and T) bear one or more fluorescent dye groups on a terminal phosphate moiety that is cleaved from the nucleotide upon incorporation. As a result, synthesized nucleic acids do not bear the build-up of fluorescent labels, as the labeled polyphosphate groups diffuses away from the complex following incorporation of the associated nucleotide, nor do such labels interfere with the incorporation event. See, e.g., Korlach et al., Nucleosides, Nucleotides and Nucleic Acids, 27:1072:1083, 2008.

In another exemplary technique, the nucleotides to be incorporated are each provided with interactive labeling components that are interactive with other labeling components provided coupled to, or sufficiently near the polymerase (which labels are interchangeably referred to herein as "complex borne"). Upon incorporation, the nucleotide borne labeling component is brought into sufficient proximity to the complex-borne (or complex proximal) labeling component, such that these components produce a characteristic signal event. For example, the polymerase may be provided with a fluorophore that provides fluorescent resonant energy transfer (FRET) to appropriate acceptor fluorophores. These acceptor fluorophores are provided upon the nucleotide to be incorporated, where each type of nucleotide bears a different acceptor fluorophore, e.g., that provides a different fluorescent signal. Upon incorporation, the donor and acceptor are brought close enough together to generate energy transfer signal. By providing different acceptor labels on the different types of nucleotides, one obtains a characteristic FRET-based fluorescent signal for the incorporation of each type of nucleotide, as the incorporation is occurring.

In a related aspect, a nucleotide analog may include two interacting fluorophores that operate as a donor/quencher pair or FRET pair, where one member is present on the nucleobase or other retained portion of the nucleotide, while the other member is present on a phosphate group or other portion of the nucleotide that is released upon incorporation, e.g., a terminal phosphate group. Prior to incorporation, the donor and quencher are sufficiently proximal on the same analog as to provide characteristic signal, e.g., quenched or otherwise indicative of energy transfer. Upon incorporation and cleavage of the terminal phosphate groups, e.g., bearing a donor fluorophore, the quenching or other energy transfer is removed and the resulting characteristic fluorescent signal of the donor is observable.

In preferred aspects, the synthesis complexes in such reaction mixtures are arrayed so as to permit observation of the individual complexes that are being so modulated. In arraying individual complexes to be individually optically resolvable, the systems of the invention will position the complexes on solid supports such that there is sufficient distance between adjacent individual complexes as to allow optical signals from such adjacent complexes to be optically distinguishable from each other.

Typically, such complexes will be provided with at least 50 nm and more preferably at least 100 nm of distance between adjacent complexes, in order to permit optical signals, and particularly fluorescent signals, to be individually resolvable. Examples of arrays of individually resolvable molecules are described in, e.g., U.S. Pat. No. 6,787,308.

In some cases, individual complexes may be provided within separate discrete regions of a support, for example on a chip. For example, in some cases, individual complexes may be provided within individual optical confinement structures, such as zero-mode waveguide cores. Examples of such waveguides and processes for immobilizing individual complexes therein are described in, e.g., Published International Patent Application No. WO 2007/123763, the full disclosure of which is incorporated herein by reference in its entirety for all purposes.

The synthesis complexes are typically provided immobilized upon solid supports, and preferably, upon supporting substrates. The complexes may be coupled to the solid supports through one or more of the different groups that make up the complex. For example, in the case of nucleic acid polymerization complexes, attachment to the solid support may be through an attachment with one or more of the polymerase enzyme, the primer sequence and/or the template sequence in the complex. Further, the attachment may comprise a covalent attachment to the solid support or it may comprise a non-covalent association. For example, in particularly preferred aspects, affinity based associations between the support and the complex are envisioned. Such affinity associations include, for example, avidin/streptavidin/neutravidin associations with biotin or biotinylated groups, antibody/antigen associations, GST/glutathione interactions, nucleic acid hybridization interactions, and the like. In particularly preferred aspects, the complex is attached to the solid support through the provision of an avidin group, e.g., streptavidin, on the support, which specifically interacts with a biotin group that is coupled to the polymerase enzyme.

The sequencing processes, e.g., using the substrates described above and the synthesis compositions of the invention, are generally exploited in the context of a fluorescence microscope system that is capable of illuminating the various complexes on the substrate, and obtaining detecting and separately recording fluorescent signals from these complexes. Such systems typically employ one or more illumination sources that provide excitation light of appropriate wavelength(s) for the labels being used. An optical train directs the excitation light at the reaction region(s) and collects emitted fluorescent signals and directs them to an appropriate detector or detectors. Additional components of the optical train can provide for separation of spectrally different signals, e.g., from different fluorescent labels, and direction of these separated signals to different portions of a single detector or to different detectors. Other components may provide for spatial filtering of optical signals, focusing and direction of the excitation and or emission light to and from the substrate.

Figure 30:
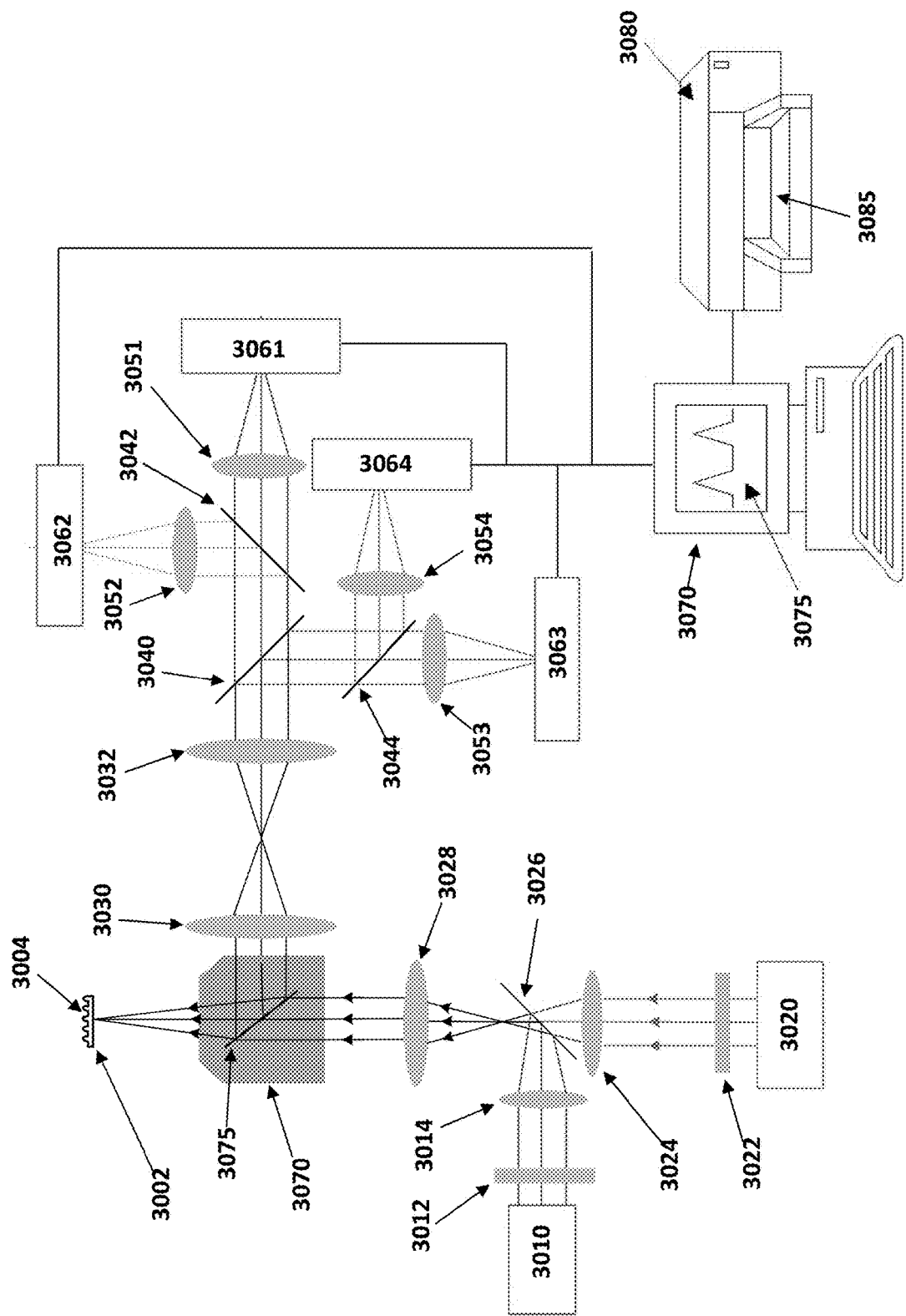
FIG. 30 shows a system for carrying out real-time single molecule sequencing.

One such exemplary system is shown in FIG. 30. An exemplary system is also described in Lundquist et al., Published U.S. Patent Application No. 2007-0036511, Optics Letters, Vol. 33, Issue 9, pp. 1026-1028, the full disclosure of which is incorporated herein by reference in its entirety for all purposes.

Fluorescence reflective optical trains can be used in the applications of the systems of the invention. For a discussion on the advantages of such systems, see, e.g., U.S. patent application Ser. No. 11/704,689, filed Feb. 9, 2007, Ser. No. 11/483,413, filed Jul. 7, 2006, and Ser. No. 11/704,733, filed Feb. 9, 2007, the full disclosures of which are incorporated herein by reference in their entirety for all purpose.

For purposes of the present invention, the processes and systems will be described with reference to detection of incorporation events in a real time, sequence by incorporation process, e.g., as described in U.S. Pat. Nos. 7,056,661, 7,052,847, 7,033,764 and 7,056,676 (the full disclosures of which are incorporated herein by reference in their entirety for all purposes), when carried out in arrays of discrete reaction regions or locations. An exemplary sequencing system for use in conjunction with the invention is shown in FIG. 30. As shown, the system includes a substrate 3002 that includes a plurality of discrete sources of optical signals, e.g., reaction wells, apertures, or optical confinements or reaction locations 3004. In typical systems, reaction locations 3004 are regularly spaced and thus substrate 3002 can also be understood as an array 3002 of reaction locations 3004. The array 3002 can comprise a transparent substrate having cladding layer on its top surface with an array of nanoscale apertures extending through the cladding to the transparent substrate. This configuration allows for one or more samples to be added to the top surface of the array, and for the array to be observed through the transparent substrate from below, such that only the light from the apertures is observed. The array can be illuminated from below as shown in FIG. 30, and in some embodiments, the array can also be illuminated from above (not shown in FIG. 30).

For illumination from below, one or more excitation light sources, e.g., lasers 3010 and 3020, are provided in the system and positioned to direct excitation radiation at the various signal sources. Here, two lasers are used in order to provide different excitation wavelengths, for example with one laser 3010 providing illumination in the red, and laser 3020 providing illumination in the green. The use of multiple laser excitation sources allows for the optimal excitation of multiple labels in a sample in contact with the array. The excitation illumination can be a flood illumination, or can be directed to discrete regions on the array, for example, by breaking the excitation beam into an array of beamlets, each beamlet directed to a feature on the array. In order to break the excitations beams into an array of beamlets, a diffractive optical element (DOE). In the system of FIG. 30, the light from excitation sources 3010 and 3020 is sent through DOE components 3012 and 3022 respectively. The use of a DOE for providing an array of beamlets is provided, e.g. in U.S. Pat. No. 7,714,303, which is incorporated by reference herein in its entirety. Excitation light is then passed through illumination relay lenses 3014 and 3024 to interact with dichroic 3026. In the system of FIG. 30, the red light from laser 3010 is reflected off of dichroic 3026, and the green light from laser 3020 is directed through the dichroic 3026. The excitation light is then passed through illumination tube lens 3028 into objective lens 3070 and onto the array 3002.

Emitted signals from sources 3004 are then collected by the optical components, e.g., objective 3070, comprising dichroic element 3075 which allows the illumination light to pass through and reflects the excitation light. The emitted light passes through collection tube lens 3030 and collection relay lens 3032. The emitted light is then separated into D different spectral channels, and each spectral channel is directed to a different detector. In the system of FIG. 30, the light is separated into four different channels, each channel corresponding predominantly to one of four labels to be detected in the sample. Thus, the system allows the user to obtain four two dimensional images, each image corresponding to one of the four labels. In order to separate the light into the four spectral channels, dichroics 3040, 3042, and 3044 are used. Dichroic 3040 allows the light for channels 1 and 2 to pass while reflecting the light for channels 3 and 4. Dichroic 3042 allows the light for channel 1 to pass, through collection imaging lens 3051 to detector 3061, and reflects the light for channel 2 through collection imaging lens 3052 to detector 3062. Dichroic 3044 allows the light for channel 3 to pass, through collection imaging lens 3053 onto detector 3063, and reflects the light for channel 4 through collection illumination lens 3054 onto detector 3064. Each of the detectors 3061-3064 comprise arrays of pixels. The detectors can be, for example, CMOS, EMCCD, or CCD arrays. Each of the detectors obtains 2-dimensional images of the channel that is directed to that detector. The data from those signals is transmitted to an appropriate data processing unit, e.g., computer 3070, where the data is subjected to processing, interpretation, and analysis. The data processing unit is configured to process the data both pixel by pixel and pixel region by pixel region, where each pixel region corresponds to a feature on the substrate. The data processing unit can receive data from calibration runs in order to define software mask pixel weighting, spectral weighting, and noise parameters. These parameters and weightings can be applied to signals that are measured on the detectors during an analytical reaction such as during sequencing. In some embodiments, the data processing unit is configured to define and apply software mask pixel weighting, spectral weighting, and noise parameters that are determined and then applied during an analytical reaction such as during sequencing.

Analyzed and processed obtained from the analytical reactions can ultimately be presented in a user ready format, e.g., on display 3075, printout 3085 from printer 3080, or the like, or may be stored in an appropriate database, transmitted to another computer system, or recorded onto tangible media for further analysis and/or later review. Connection of the detector to the computer may take on a variety of different forms. For example, in preferred aspects, the detector is coupled to appropriate Analog to Digital (A/D) converter that is then coupled to an appropriate connector in the computer. Such connections may be standard USB connections, Firewire® connections, Ethernet connections or other high speed data connections. In other cases, the detector or camera may be formatted to provide output in a digital format and be readily connected to the computer without any intermediate components.

This system, and other hardware descriptions herein, are provided solely as a specific example of sample handling and image capture hardware to provide a better understanding of the invention. It should be understood, however, that the present invention is directed to data analysis and interpretation of a wide variety of real-time florescent detecting systems, including systems that use substantially different illumination optics, systems that include different detector elements (e.g., EB-CMOS detectors, CCD's, etc.), and/or systems that localize a template sequence other than using the zero mode wave-guides described herein.

In the context of the nucleic acid sequencing methods described herein, it will be appreciated that the signal sources each represent sequencing reactions, and particularly, polymerase mediated, template dependent primer extension reactions, where in preferred aspects, each base incorporation event results in a prolonged illumination (or localization) of one of four differentially labeled nucleotides being incorporated, so as to yield a recognizable pulse that carries a distinguishable spectral profile or color.

The present invention can include computer implemented processes, and/or software incorporated onto a computer readable medium instructing such processes, as set forth in greater detail below. As such, signal data generated by the reactions and optical systems described above, is input or otherwise received into a computer or other data processor, and subjected to one or more of the various process steps or components set forth below. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

While described in terms of a particular sequencing by incorporation process or system, it will be appreciated that certain aspects of the processes of the invention may be applied to a broader range of analytical reactions or other operations and varying system configurations than those described for exemplary purposes.

In some cases, the compositions, methods, and systems of the invention can be used as part of an integrated sequencing system, for example, as described in US 20120014837—Illumination of Integrated Analytical Systems, US 20120021525—Optics Collection and Detection System and Method, US 20120019828—Integrated Analytical System and Method, 61/660,776 filed Jun. 17, 2012—Arrays of Integrated Analytical Devices and Methods for Production, and US 20120085894—Substrates and Optical Systems and Methods of Use Thereof which are incorporated herein by reference in their entirety for all purposes.

In certain embodiments, the sequencing compositions described herein will be provided in whole, or in part, in kit form enabling one to carry out the processes described herein. Such kits will typically comprise one or more components of the reaction complex, such as the polymerase enzyme and primer sequences. Such kits will also typically include buffers and reagents that provide the catalytic and non-catalytic metal co-factors employed in the processes described herein. The kits will also optionally include other components for carrying out sequencing applications in accordance with those methods described herein. In particular, such kits may include ZMW array substrates for use in observing individual reaction complexes as described herein.

In addition to the various components set forth above, the kits will typically include instructions for combining the various components in the amounts and/or ratios set forth herein, to carry out the desired processes, as also described or referenced herein, e.g., for performing sequence by incorporation reactions.

Proteins Having Buried Chromophores

Figure 12:
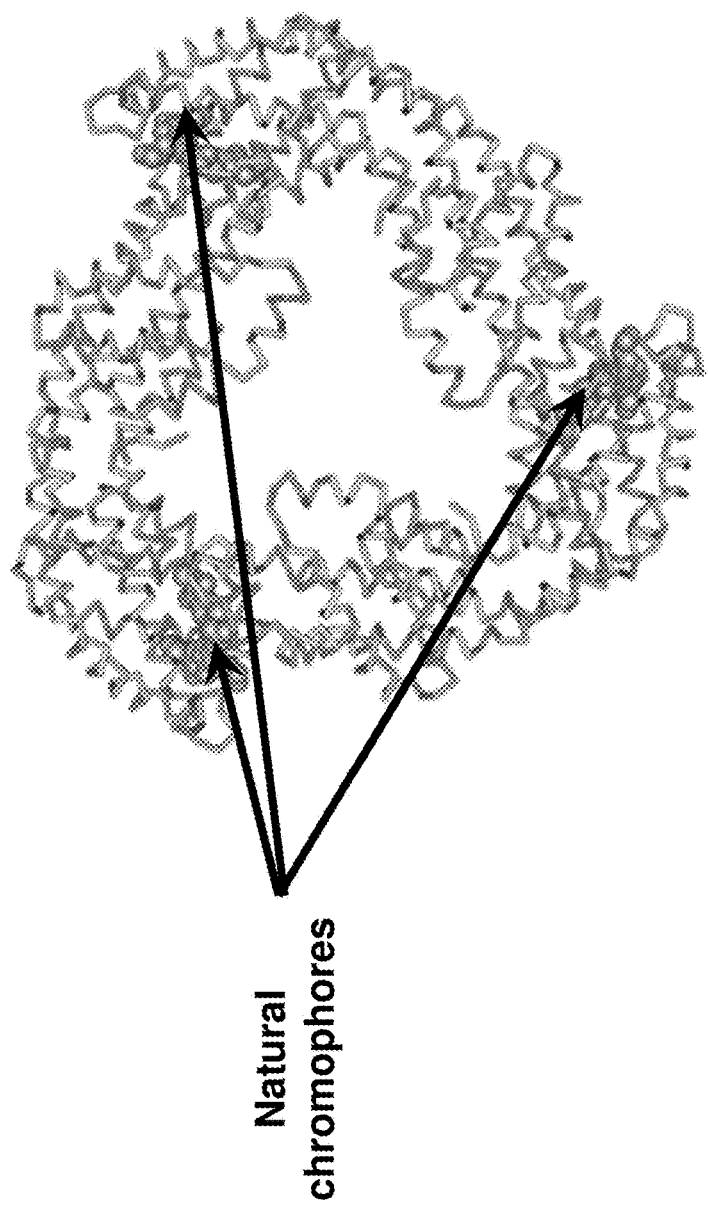
FIG. 12 shows a three dimensional representation of Allophycocyanin for use as a nucleotide analog having buried chromophores.

Another approach of the invention for ensuring that the dye portion of a nucleotide analog does not come into contact with the polymerase enzyme is to use protein scaffolds that have buried chromophores. In this approach, one or more nucleotides is attached to a protein scaffold that has one or more chromophores within its protein structure. By the term buried or the term within the protein structure, we mean that the dyes are surrounded by amino acid residues in the protein so that they are not accessible for contact with a molecule that could come into contact with the protein. Natural proteins are known that have chromophores buried within the protein. One such protein is allophycocyanin, which is the primary pigment-protein component of the cores of the phycobilisome antenna complex. See McGregor, et al. Journal: (2008) J. Mol. Biol. 384: 406-421, incorporated herein by reference in its entirety. A three dimensional representation of allophycocyanin is shown in FIG. 12. Allophycocyanin has three chromophores within its structure. One or more residues can be mutated to provide attachment points for one or more nucleotide residues.

Figure 13:
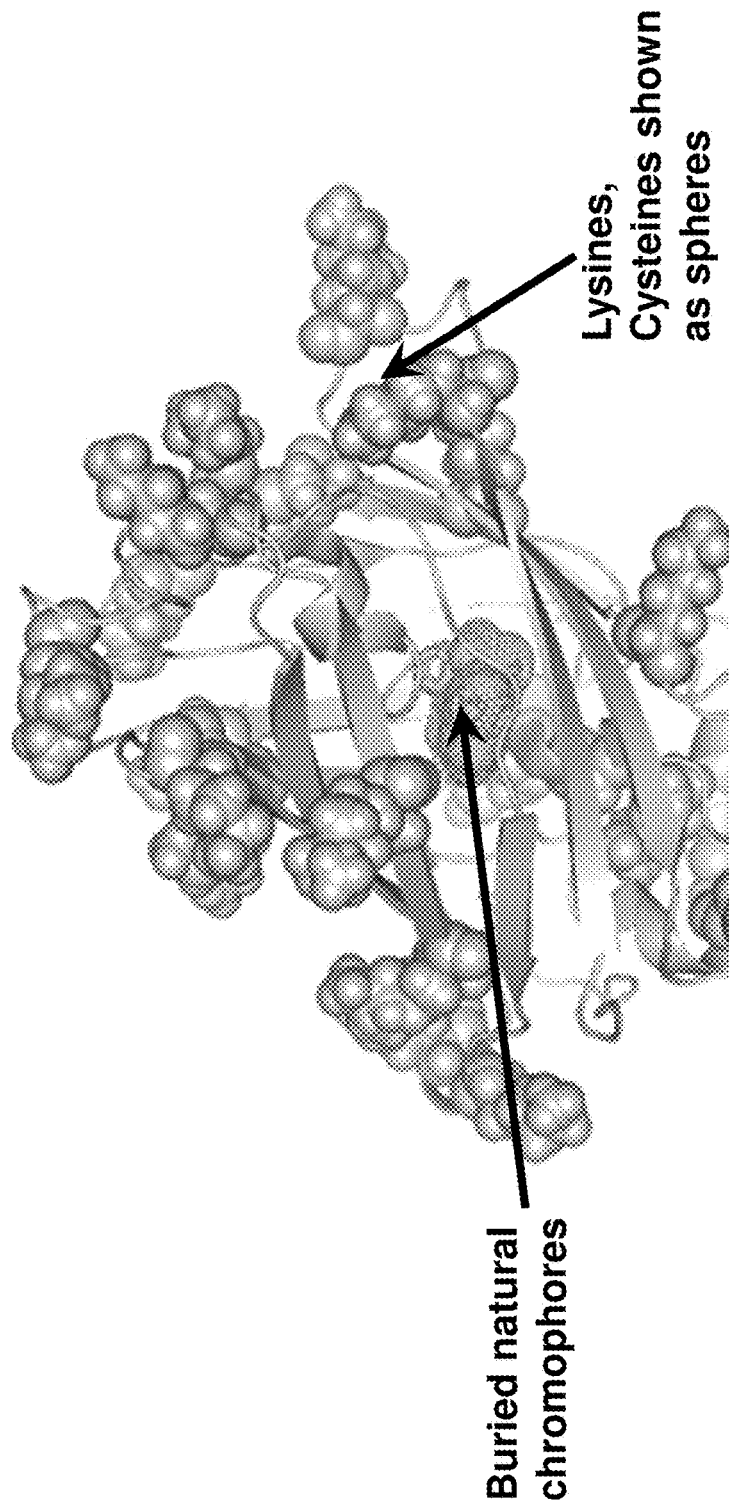
FIG. 13 shows a three dimensional representation of Green Fluorescent Protein for use as a nucleotide analog having buried chromophores.

Another protein scaffold having buried chromophores is green fluorescent protein (GFP). GFP is a protein composed of about 238 amino acid residues (26.9 kDa) that exhibits bright green fluorescence when exposed to ultraviolet blue light. In addition to native GFP, other related fluorescent proteins can also be used. For example, many mutants of GFP have been produced which have fluorescence at different wavelengths to GFP. See e.g. Shaner, N. et al. Nat Methods 2 (12): 905-9, incorporated herein by reference in its entirety. Amino acids on the protein or mutated into the protein can be used for attachment of one or more nucleotide analogs, resulting in a nucleotide analog having a fluorescent dye that will not come into contact with a polymerase associated with the nucleotide portion of the analog. For sequencing applications, several different GFP type proteins can be used to provide spectral separation in order to distinguish the bases for providing the sequence of the template. Suitable GFP type proteins include mPlum, mCherry, tdTomato, mStrawberry, J-Red, DsRed-monomer, mOrange, mKO, mCitrine, Venus, YPet, EYFP, Emerald, EGFP, CyPet, mCFPm, Cerulean, and T-Sapphire. FIG. 13 shows a three dimensional representation of a GFP showing the buried natural chromophore. Lysines and cysteines, shown as spheres, represent positions to which one or more nucleotides can be attached as described herein.

Other proteins that can be used include phycobiliproteins, ferritin, phycoerythrin or phycohemerythrin. These can be used with their native chromophore or the protein can be modified to include non-native chromophores having desired properties.

Multi-Level Dye Analogs to Mitigate Pulse Merging

Figure 31A:
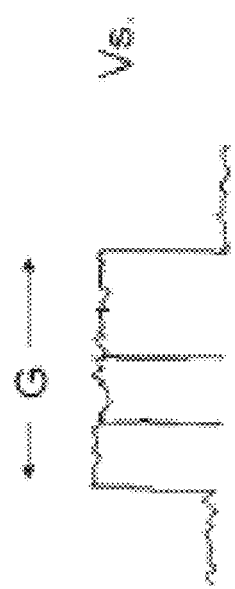
FIGS. 31(A)-31(B) show how having sets of nucleotide analogs with multiple intensity levels can allow for calling pulses that would otherwise be merged. The pulse train shown in FIG. 31(A) illustrates a run of three Gs having a short inter pulse distance (IPD) between them.
Figure 31B:
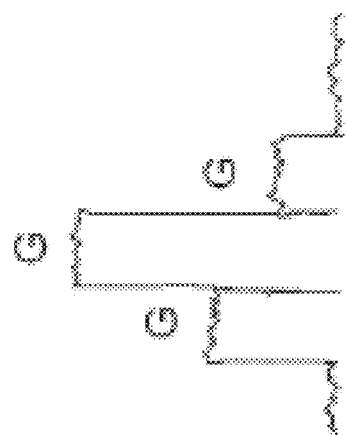

One aspect of the invention is the use of a set of analogs wherein each of the types of nucleotide analogs is represented by multiple analogs, each having a different intensity level. For example, where there are four analog types, each representing one of A, G, C, T or A, G, C, U, for each of the types there are analogs present having 1, 2, 3, 4, 5, or 6 fluorescent dyes. An advantage of this approach is that it provides a way of mitigating pulse merging in real time sequencing. Pulse merging results when two real time sequencing events happen close together in time such that it is difficult to tell that they are separate events. In some cases when the individual pulses are not identified, they are seen as a single "merged" pulse. The use of a mixture of multi-level dyes allows the base caller to use brightness as a method to discriminate one vs. multiple incorporation events in a run of homopolyrners. FIG. 31 illustrates this concept. The pulse train shown in FIG. 31(A) illustrates a run of three Gs having a short inter pulse distance (IPD) between them. When the pulses merge in this manner, the base caller can have trouble correctly recognizing that this represents 3 Gs. The example shown in FIG. 31(B) illustrates a pulse train with similar overall kinetics to that in FIG. 31(A), but with the use of multi-level dyes. Here, rather than having one nucleotide analog representing G, a group of nucleotide analogs is used in which the members of the group have different brightness levels. This can be accomplished, for example by having three G analogs, each with a different brightness level. In some cases, 3, 4, 5, 6, 7, 9, or 10 different brightness levels can be used. The group of analogs can be a set of analogs each using the same type of dye, but with different members of the set having different numbers of dyes.

Multilevel dye analogs can be made, for example using a streptavidin core. For example one or more nucleotides can be connected to streptavidin through one of the four biotin binding sites. The other three sites can be randomly populated with dye such that a set of nucleotide analogs (each having one type of base, e.g. G) having 1, 2 and 3 dyes or 2, 4, and 6 dyes is created. Alternatively, the one or more nucleotide moieties can be attached directly to the streptavidin, and the four biotin binding sites can be randomly populated with dyes to provide an analog set having 1, 2, 3, and 4 dyes, or 2, 4, 6, and 8 dyes. Multilevel dye analogs with a streptavidin core have been produced by the inventors and used in real time single molecule sequencing. Results showed that analogs having multiple different levels of signal could be detected.

EXAMPLES

Figure 32:
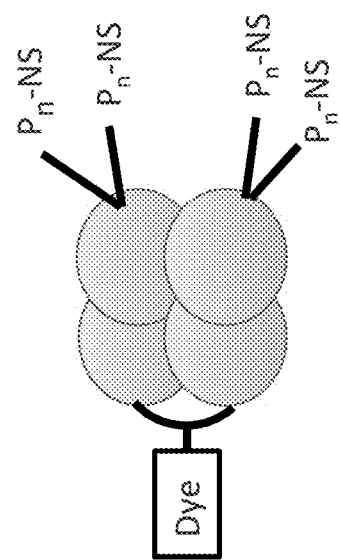
FIG. 32 shows one construct of a nucleotide analog having a streptavidin protein shield.

Example 1: Sequencing with Nucleotide Analogs Using a Streptavidin Protein Shield FIG. 32 shows a type of streptavidin structures that can be used to increase photostability of a nucleic acid sequencing reaction. The central portion of the analog is the tetrameric streptavidin protein. A dye is attached through a linker molecule having two biotin sites that are designed such that each of the biotins can attach to one binding site on a single streptavidin. To the other two sites on the streptavidin are attached nucleotides (nucleoside phosphates, Pn-NS) that are attached to the streptavidin through their phosphate groups (Pn). In the version shown in FIG. 32, two nucleotides are attached at each of the two biotin binding sites resulting in four nucleoside phosphates per streptavidin. Analogous constructs can be made having 2, 3, 4, or more dyes attached to a the linker molecule having two biotins. The number of nucleotides can also be varied by having 1, 2, 3, 4 or more nucleotides bound to each biotin binding site.

Figure 33:
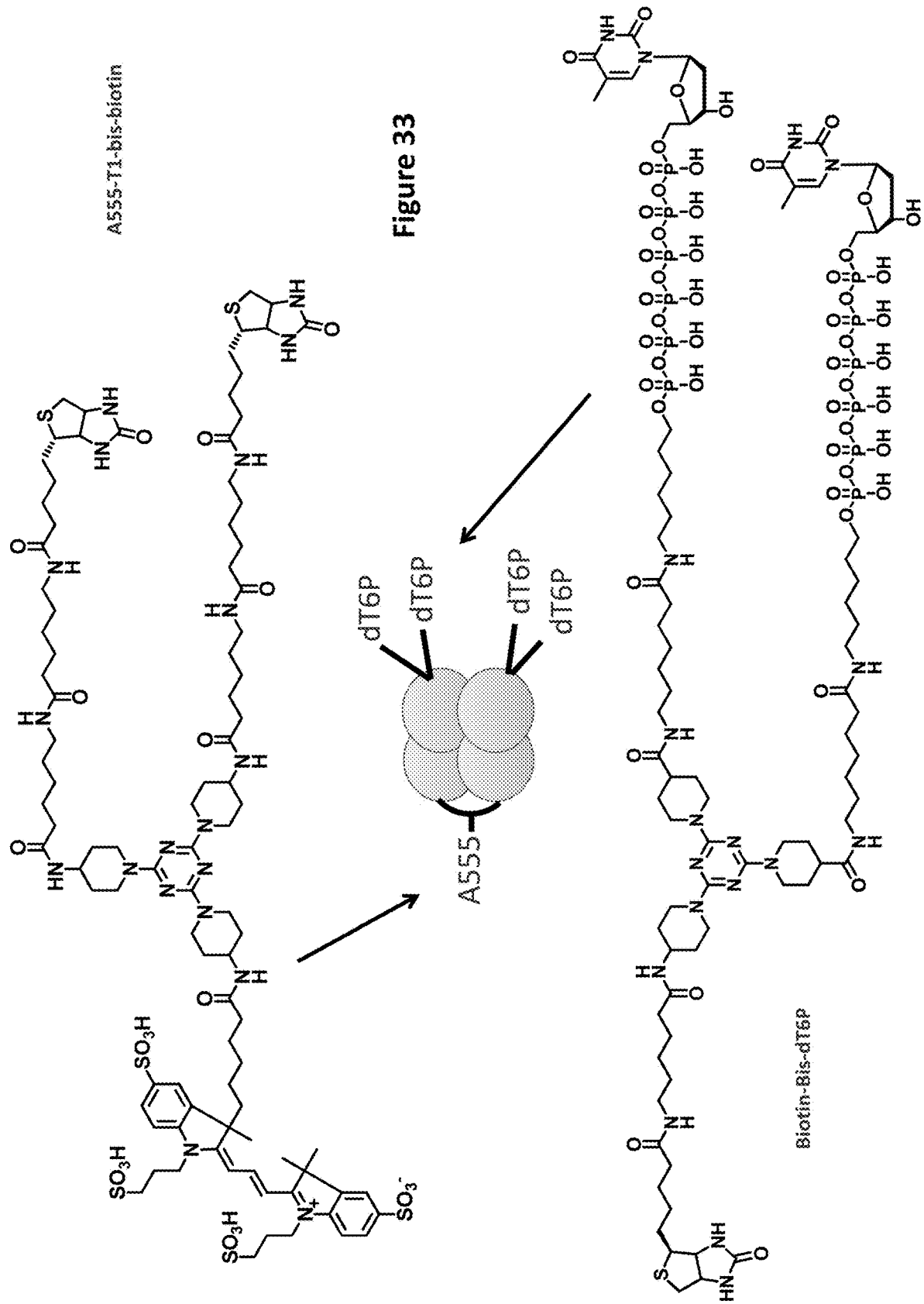
FIG. 33 shows a construct of a nucleotide analog having a streptavidin protein shield that was used in real-time single molecule sequencing.

FIG. 33 shows one example of a structure of a nucleotide analog having a protein shield that the inventors have prepared and used to perform single molecule real time nucleic acid sequencing. The A555-T1-bis-biotin shown in FIG. 33 was synthesized by conventional organic chemical techniques. A555 is a fluorescent dye moiety that can be useful in single molecule sequencing. T1 is the designation of the trifunctional unit. The A555-T1-bis-biotin was reacted with streptavidin and purified to isolate the complex having a single A555-T1-bis-biotin attached to streptavidin. This complex was then contacted with biotin-bis-dT6P (shown in FIG. 33). Biotin-bis-dT6P has a single biotin attached through a trifunctional liner to two nucleotides. The nucleotides are deoxythymidine hexaphosphates. This synthesis results in the preparation of the nucleotide analog shown in FIG. 33 having one A555 dye on one side of the streptavidin and having four nucleotides attached to the other side of the streptavidin.

Figure 34A:
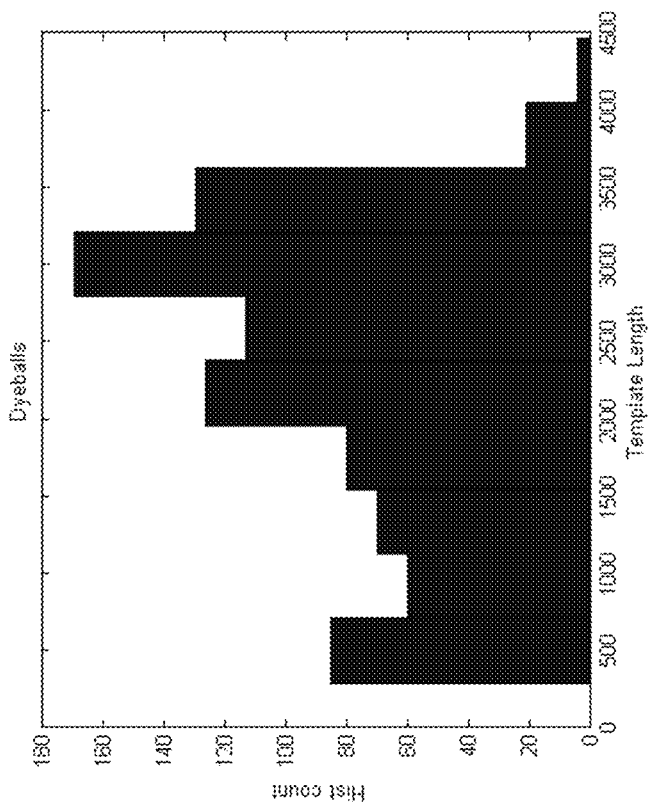
FIGS. 34(A)-34(B) show histograms of read lengths for a control FIG. 34(A) and for a sequencing reaction with a nucleotide analog having a protein shield showing improved photostability FIG. 34(B).
Figure 34B:
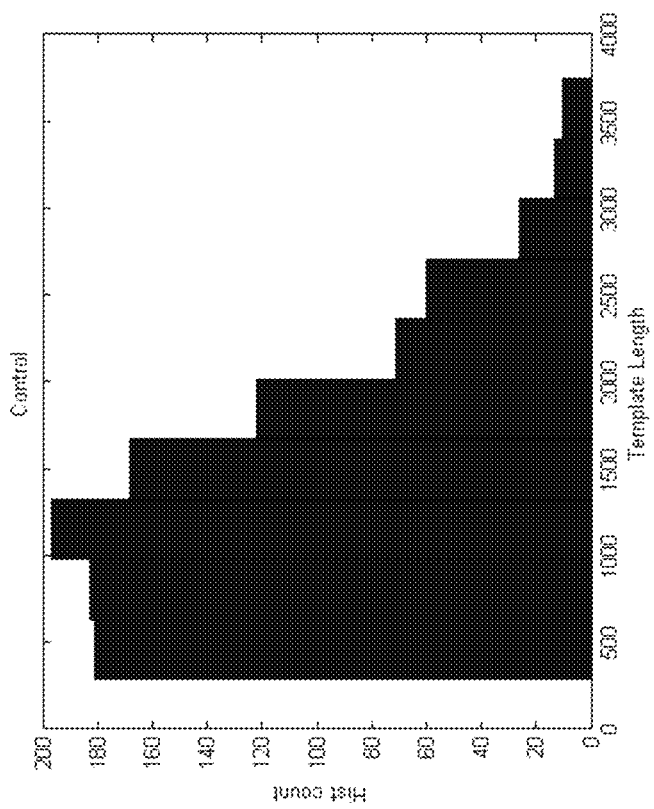
Figure 35B:
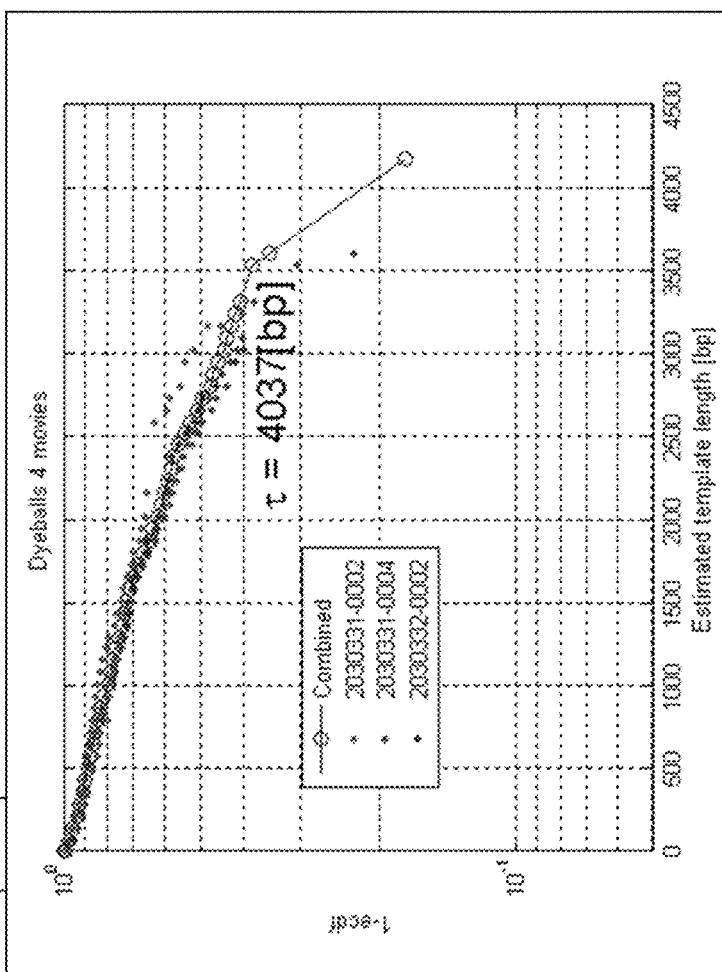
FIGS. 35(A)-35(B) show read length plots for four movies of a control FIG. 35(A) and for a sequencing reaction with a nucleotide analog having a protein shield showing improved photostability FIG. 35(B).
Figure 35A:
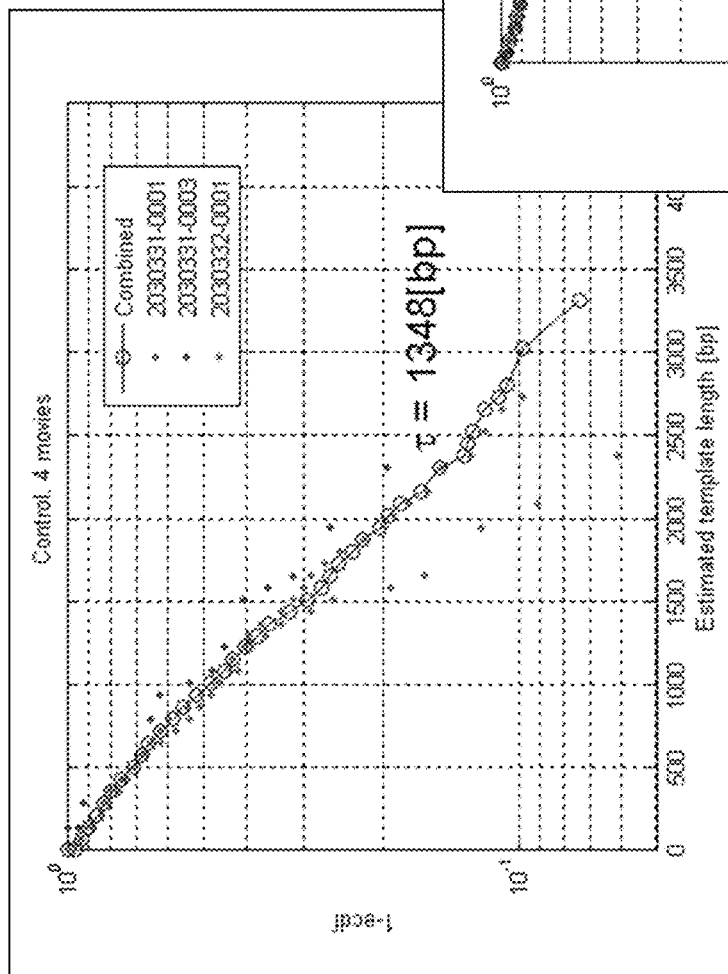

The nucleotide analog with protein shield of FIG. 33 was used in a single molecule sequencing reaction carried out in a sequencing system as describe in Eid, J. et al., Science, 323(5910), 133-138 (2009)) using a 72 base circular template. The experiment was carried out to emphasize photodamage in the channel with the protein shield nucleotide analog. The movie length was 30 minutes, and the laser power was 2.5 µW/µm². Concentrations were adjusted, e.g. by raising the concentrations of the protein shield nucleotide analog to match the kinetics (e.g. interpulse distance) of a control reaction carried out in the same manner, but with a conventional nucleotide analog in place of the protein shield nucleotide analog. Results of the experiment are shown in FIGS. 19 and 20. A measure of improvements in photostability of the sequencing system is the readlength. Experiments have shown that when light exposure is minimized, longer readlengths can be obtained, indicating that photodamage is limiting the readlength. FIG. 34 shows readlength histograms for the control (A) and protein shielded nucleotide analog (B). It can be seen from the figures that the reaction run with the protein shielded nucleotide analog has a distribution with significantly longer readlengths. The change in shape of the histograms is partly due to the fact that for longer read lengths, the length of the movie can be the limiting factor in the readlength obtained. FIG. 35 shows the data for four control movies (A) and four protein shielded nucleotide analog movies (B). Tau (τ) is a measure of the readlength. It can be seen that for the control, τ is 1,348 base pairs, while τ for the protein shield nucleotide analog is 4,037 base pairs. Again, this shows a significant increase in readlength which indicates a significant improvement in photostability of the sequencing system by using the protein shielded nucleotide analog.

Example 2: Streptavidin Constructs

The following streptavidin constructs have been cloned for use as protein shields:

pET11a.Core_Streptavidin.co
pET11a.CTerm_His6co.Core_Streptavidin.co
pET11a.Core_Streptavidin.N23A_S27D_S45A.co
pET11a.Core_Streptavidin.N23A_S27D_S45A_N49C.co
pET11a.Core_Streptavidin.N23A_S27D_S45A_S139C.co
pET11a.Core_Streptavidin.N49C.co
pET11a.Core_Streptavidin.S139C.co

Example 3: Top7 Constructs

The following mutants have been cloned:

pET11a.TOP7.co.His6co
pET11a.TOP7.K15R_K31R_K41R_K42R_K46R_K57R_K58R_K62R_K69R_110.1C.co.His6co
pET11a.BtagV07co.TOP7.100.1C.co.His6co The first three mutants have been purified, and found to express well. The second construct knocks out all the lysines except for the N-terminus, and introduces a unique cysteine. This second construct generates a scaffold which can be attached to one dye and one base, with the two attachment points ~30 Angstroms apart. The third construct allows multiple attachment points through lysine (e.g. for bases) and a unique cysteine through which to couple a dye. Alternately, because it contains a B-tag, this construct can also be combined with the streptavidin experiments. For example using biotin tagged dye+lysine targeted base tagged top 7, one could obtain streptavidin tetramers where some of the monomers were associated with dye, and other monomers with top7/base.

Example 4: Real-Time Single Molecule Sequencing Using Nucleotide Analogs with Both the Dye Component and Phospholinked Nucleotide Component Attached Through a Bis-Biotin Moiety This experiment was performed to determine the sequencing performance of a full set of four protein shield nucleotide analogs with both the dye component and phospholinked nucleotide component attached through bis-biotin linkers. A set of protein shield analogs was made with a structure similar to that shown in FIG. 23 corresponding to bases A, G, C, and T. Each of the T, A, and C protein shield analogs had 6 phospholinked nucleotide moieties linked to a streptavidin through a bis-biotin linker. The G protein shield nucleotide analogs had 4 phospholinked nucleotide moieties linked to a streptavidin through a bis-biotin linker. Each of the nucleotide analogs had a different dye component. The T analog had a double dye moiety with an emission maximum of about 558 nm, the G analog had a FRET dye pair with an emission maximum of about 598 nm, the A analog had a single dye with an emission maximum of about 659 nm, and the C analog had a FRET dye pair with an emission maximum of about 697 nm. The four protein shield nucleotide analogs were added at a final concentration of 65-1,000 nM. The template nucleic acid was a 250 base pair cyclic template. Sequencing was performed on a PACBIO™ RS sequencing instrument using standard laser and analysis options. The SMRT sequencing method performed is described, for example, in Korlach et al., Methods in Enzymology, Volume 472, 2010, Pages 431-455. In addition, free streptavidin was added to the mix in the range of 65 to 650 nM. Additionally 650 nM free streptavidin is added to the chip wash buffer. All other reagents are standard. The polymerase enzyme used was a mutant Phi-29 polymerase enzyme including an E508R mutation such as described in copending patent application entitled "Recombinant Polymerases for Incorporation of Protein Shield Nucleotide Analogs", U.S. patent application Ser. No. 61/764,971, filed Feb. 14, 2013, which is incorporated herein by references in its entirety for all purposes. The sequencing movies were run for two hours. The protein shield nucleotide analogs performed very well with an average readlength was 9,650 bases with an average accuracy of 83.8%. The fraction of traces that were movie limited was 25%.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

We claim:

1. A polymerase enzyme substrate comprising:
   a protein comprising at least 60 amino acids;
   a nucleotide component comprising at least one nucleoside polyphosphate attached through its phosphate portion to a first position on the protein;
   a dye component comprising at least one fluorescent dye moiety attached to a second position on the protein.

2. The polymerase enzyme substrate of claim 1 wherein the nucleotide component or the protein component are connected covalently attached to the protein.

3. The polymerase enzyme substrate of claim 1 wherein the protein comprises 60 to 1,000 amino acids.

4. The polymerase enzyme substrate of claim 1 wherein the protein comprises 80 to 600 amino acids.

5. The polymerase enzyme substrate of claim 1 wherein the nucleotide component and dye component are covalently attached to the protein.

6. The polymerase enzyme substrate of claim 1 wherein the nucleotide component comprises two or more nucleoside phosphates.

7. The polymerase enzyme substrate of claim 1 wherein the substrate has 2, 3, 4, 5, 6, 7, or 8 nucleotide phosphates.

8. The polymerase enzyme substrate of claim 1 wherein the dye component comprises two or more fluorescent dye moieties.

9. The polymerase enzyme substrate of claim 1 wherein the substrate has 2, 3, or 4 fluorescent dye moieties.

10. The polymerase enzyme substrate of claim 2 wherein the covalent attachment is through a cysteine or lysine residue on the protein.

11. The polymerase enzyme substrate of claim 1 having two or more nucleotide components attached to the protein.

12. The polymerase enzyme substrate of claim 1 having two or more dye components attached to the protein.

13. The polymerase enzyme substrate of claim 1 wherein the first position and the second position are spaced apart by a distance whereby when at least one nucleoside phosphate of the nucleoside component is in the active site of a polymerase enzyme, the at least one fluorescent dye moiety of the dye component is shielded by the protein from coming into contact with the polymerase enzyme.

14. The polymerase enzyme substrate of claim 1 wherein the protein has two or more nucleotide components and two or more dye components, wherein when any nucleotide phosphate in a nucleotide component is in the active site of the polymerase enzyme, all fluorescent dye moieties in the dye components are shielded by the protein from coming into contact with the polymerase enzyme.

15. The polymerase enzyme substrate of claim 1 wherein the protein comprises a first protein and a second protein, and the first protein and second protein are associated or connected, wherein the first protein has one or more nucleotide components attached to it, and the second protein has one or more dye components attached to it.

16. The polymerase enzyme of claim 15 wherein the first protein and second protein are associated.

17. The polymerase enzyme substrate of claim 16 wherein the first protein and second protein comprise barnase and barstar.

18. The polymerase enzyme substrate of claim 15 wherein the first protein and second protein are connected by a covalent linkage.

19. The polymerase enzyme substrate of claim 18 wherein the first protein and second protein are connected through one or more linkers.

20. The polymerase enzyme substrate of claim 1 wherein the protein comprises a Ubiquitin, TOP7, Tamavidin, Papain, Maltose Binding Protein, Snap tag protein, or beta lactamase protein.

21. The polymerase enzyme substrate of claim 1 wherein the polymerase enzyme is a modified phi29-type DNA polymerase enzyme.

22. The polymerase enzyme substrate of claim 1 wherein the nucleotide component is attached to the protein through a linker.

23. The polymerase enzyme substrate of claim 1 wherein the dye component is attached to the protein through a linker.

24. A method for nucleic acid sequencing comprising:
providing an array of individually observable enzyme-nucleic acid template complexes on a chip;
exposing the chip to the reagents for polymerase mediated nucleic acid synthesis of a growing nucleic acid strand, the reagents comprising a plurality of differently labeled polymerase enzyme substrates including at least one polymerase nucleic acid substrate of claim 1; and
optically monitoring the incorporation of the nucleoside monophosphate portions of the differently labeled polymerase enzyme substrates into the growing nucleic acid strand over time, thereby determining the sequence of at least a portion of the nucleic acid template.

25. A system for sequencing nucleic acids comprising:
a chip comprising a plurality of polymerase enzyme complexes bound thereto, each polymerase enzyme complex individually optically resolvable, each polymerase enzyme complex comprising a polymerase enzyme, a template nucleic acid, and optionally a primer hybridized to the template nucleic acid,
sequencing reagents in contact with the surface comprising reagents for carrying out nucleic acid synthesis including 1 or more polymerase enzyme substrates of claim 1; and
an illumination system for illuminating the polymerase enzyme complexes; and
an optical detection system for detecting fluorescence from the fluorescent dye moieties while they are polymerase enzyme substrates are interacting with the polymerase enzyme complexes; and
a computer for analyzing the signals detected by the detection system to determine the sequential addition of nucleotides to a nucleic acid strand complementary to a strand of the template nucleic acid.

* * * * *